US006984734B2

(12) United States Patent
Sessler et al.

(10) Patent No.: US 6,984,734 B2
(45) Date of Patent: Jan. 10, 2006

(54) CYCLO[N]PYRROLES AND METHODS THERETO

(75) Inventors: Jonathan L. Sessler, Austin, TX (US); Daniel Seidel, Cambridge, MA (US); Frederic R. Bolze, Strasbourg (FR); Thomas Koehler, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 293 days.

(21) Appl. No.: 10/373,949

(22) Filed: Feb. 26, 2003

(65) Prior Publication Data

US 2003/0229131 A1 Dec. 11, 2003

Related U.S. Application Data

(60) Provisional application No. 60/359,752, filed on Feb. 26, 2002.

(51) Int. Cl.
*C07D 245/00* (2006.01)
*G02F 1/035* (2006.01)
*G11B 7/24* (2006.01)
*B32B 3/26* (2006.01)

(52) U.S. Cl. .................... 540/460; 540/451; 540/455; 540/468; 540/470; 540/476; 385/2; 430/270.15; 430/270.16; 428/304.4

(58) Field of Classification Search ................ 540/460, 540/451, 455, 468, 470, 476; 385/2; 430/270.15, 430/270.16; 428/304.4
See application file for complete search history.

(56) References Cited

U.S. PATENT DOCUMENTS

| 3,923,460 | A | * | 12/1975 | Parrott et al. ............... 436/149 |
|---|---|---|---|---|
| 4,507,466 | A | | 3/1985 | Tomalia et al. |
| 4,935,498 | A | | 6/1990 | Sessler et al. |
| 5,024,923 | A | * | 6/1991 | Suzuki et al. ............... 430/372 |
| 5,041,078 | A | | 8/1991 | Matthews et al. |
| 5,041,516 | A | | 8/1991 | Fréchet et al. |
| 5,091,108 | A | * | 2/1992 | Harder et al. .......... 252/188.28 |
| 5,120,411 | A | | 6/1992 | Sessler et al. |
| 5,134,048 | A | | 7/1992 | Terrell et al. |
| 5,159,065 | A | | 10/1992 | Sessler et al. |
| 5,162,509 | A | | 11/1992 | Sessler et al. |
| 5,179,120 | A | | 1/1993 | Vogel et al. |
| 5,231,523 | A | | 7/1993 | Nakaya et al. |
| 5,252,720 | A | | 10/1993 | Sessler et al. |
| 5,256,399 | A | | 10/1993 | Sessler et al. |
| 5,272,142 | A | | 12/1993 | Sessler et al. |
| 5,292,414 | A | | 3/1994 | Sessler et al. |
| 5,302,714 | A | | 4/1994 | Sessler et al. |
| 5,357,357 | A | | 10/1994 | Imazeki et al. |
| 5,369,101 | A | | 11/1994 | Sessler et al. |
| 5,409,783 | A | | 4/1995 | Tang et al. |

(Continued)

FOREIGN PATENT DOCUMENTS

| WO | WO 96/21665 | 7/1996 |
|---|---|---|
| WO | WO 97/37995 | 10/1997 |
| WO | WO 03/018548 | 6/2003 |

OTHER PUBLICATIONS

Waluk et al. The Perimeter Model and Magnetic Circular Dichroism of Porphyrin Analogues. J. Org. Chem 1991, 56, pp. 2729–2735.*

Banwell, et al., "Convergent syntheses of the pyrrolic marine natural products lamellarin–O, lamellarin–Q, lukianol–A and some more highly oxygenated congeners", *Chem. Commun.*, (1997), pp. 207–208, The Royal Society of Chemistry.

Barton, et al., "A Useful Synthesis of Pyrroles from Nitroolefins", *Tetrahedron*, vol. 46, No. 21, (1990), pp. 7587–7598, Elsevier Science Ltd.

Berlin, et al., "Expeditious Synthesis of Dihydrobenzo–[2, 1–b : 3,4–b ']–,[1,2–b : 5,4–b'], and [1,2–b : 4,5–b']–dipyrroles", *J. Chem. Soc., Chem. Commun.*, (1987), pp. 1176–1177, The Royal Society of Chemistry.

Berlin, et al., "Methyl labeling as a tool for investigating the regiochemistry of the electrochemical oxidative polymerization of 1H,8H–pyrrolo[3,2–g]indole", *Makromol. Chem.*, vol. 191, (1990), pp. 1497–1511, Huthig & Wepf Verlag, Basel.

Burrell, et al., "Uranylpentaphyrin: An Actinide Complex of an Expanded Porphrin", *J. Am. Chem. Soc.*, vol. 113, (1991), pp. 4690–4692, American Chemical Society.

Furuta, et al., "Phosphate Anion Binding: Enhanced Transport of Nucleotide Monophosphates Using a Sapphyrin Carrier", *J. Am. Chem. Soc.*, vol. 113, (1991), pp. 6677–6678, American Chemical Society.

Furuta, et al., "Protonated rubyrin and C–Tips: co–carriers for the transport of guanosine 5'–monophosphate at neutral pH", *Supramolecular Chemistry*, vol. 3, (1993), pp. 5–8, Gordon and Breach Science.

Gebauer, "Synthese neuartiger Thiaporphyrinoide", Diplomarbeit, University of Cologne, Federal Republic of Germany, (1993), (see IDS for explanation).

(Continued)

*Primary Examiner*—James O. Wilson
*Assistant Examiner*—Matthew L. Fedowitz
(74) *Attorney, Agent, or Firm*—Haynes and Boone, LLP

(57) ABSTRACT

The present invention provides an oxidative coupling procedure that allows efficient synthesis of novel cyclo[n] pyrrole macrocycles. Therefore, the present invention provides cyclo[n]pyrroles where n is 6, 7, 8, 9, 10, 11, or 12, and derivatives, multimers, isomers, and ion and neutral molecule complexes thereof as new compositions of matter. A protonated form of cyclo[n]pyrrole displays a gap of up to 700 nm between strong Soret and Q-like absorption bands in the electronic spectrum, demonstrating no significant ground state absorption in the visible portion of the electronic spectrum. Uses of cyclo[n]pyrroles as separation media, nonlinear optical materials, information storage media and infrared filters are provided.

10 Claims, 7 Drawing Sheets

U.S. PATENT DOCUMENTS

| | | | | |
|---|---|---|---|---|
| 5,410,045 | A | * 4/1995 | Sessler et al. | 540/472 |
| 5,432,171 | A | 7/1995 | Sessler et al. | |
| 5,439,570 | A | 8/1995 | Sessler et al. | |
| 5,451,576 | A | 9/1995 | Sessler et al. | |
| 5,457,183 | A | 10/1995 | Sessler et al. | |
| 5,457,195 | A | 10/1995 | Sessler et al. | |
| 5,475,104 | A | 12/1995 | Sessler et al. | |
| 5,523,871 | A | 6/1996 | Shibata et al. | |
| 5,530,123 | A | 6/1996 | Sessler et al. | |
| 5,543,514 | A | 8/1996 | Sessler et al. | |
| 5,559,207 | A | 9/1996 | Sessler et al. | |
| 5,569,759 | A | 10/1996 | Sessler et al. | |
| 5,587,463 | A | 12/1996 | Sessler et al. | |
| 5,587,478 | A | 12/1996 | Sessler et al. | |
| 5,589,069 | A | * 12/1996 | Wenzhi | 210/635 |
| 5,594,136 | A | 1/1997 | Sessler et al. | |
| 5,599,923 | A | 2/1997 | Sessler et al. | |
| 5,622,945 | A | 4/1997 | Sessler et al. | |
| 5,658,707 | A | 8/1997 | Takuma et al. | |
| 5,714,166 | A | 2/1998 | Tomalia et al. | |
| 5,714,328 | A | 2/1998 | Magda et al. | |
| 5,718,838 | A | 2/1998 | Okazaki | |
| 5,733,903 | A | 3/1998 | Sessler et al. | |
| 5,744,302 | A | 4/1998 | Sessler et al. | |
| 5,756,724 | A | 5/1998 | Vogel et al. | |
| 5,775,339 | A | 7/1998 | Woodburn et al. | |
| 5,776,925 | A | 7/1998 | Young et al. | |
| 5,798,491 | A | 8/1998 | Magda et al. | |
| 5,808,059 | A | 9/1998 | Sessler et al. | |
| 5,871,882 | A | 2/1999 | Schmidhalter et al. | |
| 5,945,209 | A | 8/1999 | Okazaki et al. | |
| 5,994,535 | A | 11/1999 | Sessler et al. | |
| 6,022,526 | A | 2/2000 | Woodburn et al. | |
| 6,069,140 | A | * 5/2000 | Sessler et al. | 514/185 |
| 6,099,750 | A | 8/2000 | Simmerer et al. | |
| 6,159,562 | A | 12/2000 | Kanbe et al. | |
| 6,255,424 | B1 | 7/2001 | Knauss | |
| 6,262,257 | B1 | 7/2001 | Gale et al. | |
| 6,265,034 | B1 | 7/2001 | Kagawa et al. | |
| 6,303,238 | B1 | 10/2001 | Thompson et al. | |
| 6,319,581 | B1 | 11/2001 | Tamura | |
| 6,324,091 | B1 | 11/2001 | Gryko et al. | |
| 6,339,290 | B1 | 1/2002 | Nakaya | |
| 2002/0026047 | A1 | 2/2002 | Gale et al. | |
| 2002/0115566 | A1 | 8/2002 | Sessler et al. | |

OTHER PUBLICATIONS

Gregg, et al., "2, 3, 7, 8, 12, 13, 17, 18–Octakis(β–hydroxyethyl)porphyrin (Octaethanolporphyrin) and Its Liquid Crystalline Derivatives: Synthesis and Characterization", *J. Am. Chem. Soc.*, vol. 11, (1989), pp. 3024–3029, American Chemical Society.

Hodge, et al., "The Halogenation of Methyl Pyrrole–2–carboxylate and of Some Related Pyrroles", *J. Chem. Soc.*, (1965), pp. 459–470, The Royal Society of Chemistry.

Jasat, et al., "Expanded Porphyrins and Their Heterologs", *Chemical Reviews*, vol. 97, No. 6, (1997), pp. 2267–2340, American Chemical Society.

Johnson, et al., "Synthesis and Characterization of a New [4.0.4.0] Porphyrin–like Antiaromatic Macrocycle", *Journal of Porphyrins and Phthalocyanines*, vol. 1, (1997), pp. 87–92, John Wiley & Sons, Ltd.

Král, et al., "Molecular Recognition at an Organic–Aqueous Interface: Heterocalixarenes as Anion Binding Agents in Liquid Polymeric Membrane Ion–Selective Electrodes", *J. Am. Chem. Soc.*, vol. 121, (1999), pp. 8771–8775, American Chemical Society.

Krömer, et al. "Synthesis of the First Fully α–Conjugated Macrocyclic Oligothiophenes: Cyclo[n]thiophenes with Tunable Cavities in the Nanometer Regime", *Angew. Chem. Int. Ed.*, vol. 39, No. 19, (2000), pp. 3481–3486, Wiley–VCH Verlag GmbH.

Lash, et al., "Conjugated Macrocycles Related to the Porphyrins. Part 16. Synthesis of Hexa– and Heptaalkyl–Substituted Inverted or N–Confused Porphyrins by the "3 + 1" Methodology", *J. Org. Chem.*, vol. 64, (1999), pp. 7973–7982, American Chemical Society.

Leroy, et al, "First Access to 3,4–Difluoro–1$H$–pyrrole", *Tetrahedron Letters*, vol. 35, No. 46, (1994), pp. 8605–8608, Elsevier Science Ltd.

Lin, et al., "Potentiometric Responses of Expanded Porphyrin Incorporated Liquid Membrane Electrodes toward a Series of Inorganic and Organic Anions", *Analytical Sciences*, vol. 14, (1998), pp. 99–108, The Japan Society for Analytical Chemistry.

Magda, et al., "Redox Cycling by Motexafin Gadolinium Enhances Cellular Response to Ionizing Radiation by Forming Reactive Oxygen Species", *Int. J. Radiation Oncology Biol. Phys.*, vol. 51, No. 4, (2001), pp. 1025–1036; Elsevier Science Inc.

Meyer, et al., "Synthesis and Characterization of New Non–aromatic Texaphyrin–type Expanded Porphyrins", *Journal of Porphyrins and Phthalocyanines*, vol. 3, (1999), pp. 148–158, John Wiley & Sons, Ltd.

Mody, et al., "Texaphyrins: Synthesis and Development of a Novel Class of Therapeutic Agents", *Progress in Inorganic Chemistry*, vol. 49. (2001), pp. 551–598, John–Wiley & Sons, Inc.

Morosini, et al., "5, 10, 20, 25, 35, 40–Hexanornonapyrrin: The Largest Structurally Characterized Oligopyrrole Prepared to Date", *J. Org. Chem.*, vol. 62, (1997), pp. 8848–8853, American Chemical Society.

Odashima, et al., "Chemical sensing based on membrane potential change induced by host–guest complexation at a membrane surface", *Supramolecular Chemistry*, vol. 4, (1994), pp. 101–113, Gordon and Breach Science.

Richter, et al, "Oxidation with dilute aqueous ferric chloride solutions greatly improves yields in the '4+1' synthesis of sapphyrins", *Tetrahedron Letters*, vol. 40, (1999), pp. 6735–6738, Elsevier Science Ltd.

Sessler, et al., "Sapphyrins: Versatile Anion Binding Agents", *Acc. Chem. Res.*, vol. 34, (2001), pp. 989–997, American Chemical Society.

Sessler, et al., "Hexaphyrin(1.0.1.0.0.0): An Expanded Porphyrin Ligand for the Actinide Cations Uranyl ($UO_2^{2+}$) and Neptunyl ($NpO_2^+$)", *Angew. Chem. Int. Ed.*, vol. 40, No. 3, (2001), pp. 591–594, Wiley–VCH Verlag GmbH.

Sessler, et al., "Sapphyrin–Lasalocid conjugate: a novel carrier for aromatic amino acid transport", *Chem. Commun.*, (1996), pp. 1119–1120, The Royal Society of Chemistry.

Sessler, et al., "Synthesis and characterization of an oxasapphyrin–uranyl complex", *Chem. Commun.*, (1998), pp. 1835–1836, The Royal Society of Chemistry.

Sessler, et al., "Actinide expanded porphyrin complexes", *Coordination Chemistry Reviews*, vol. 216–217, (2001), pp. 411–434, Elsevier Science SA.

Sessler, et al., "Anion carriers: New tools for crossing membranes", *ChemTech,* vol. 29, (1999), pp. 16–24, American Chemical Society.

Sessler, et al., "Phosphate anion chelation and base–pairing. Design of receptors and carriers for nucleotides and nucleotide analogues", *Supramolecular Chemistry,* vol. 1, (1993), pp. 209–220, Gordon and Breach Science.

Sessler, et al. "An Efficient, High–Yield Preparation of Substituted 2,2'–Bipyrroles", *Synlett,* (1994), pp. 211–212, Georg Thieme Verlag.

Sessler, et al. "The First 'Crowned' Expanded Porphyrin", *Tetrahedron Letters,* vol. 36, No. 8, (1995), p. 1175–1176, Elsevier Science Ltd.

Sessler, et al. "Expanded Porphyrins", *The Porphyrin Handbook,* vol. 2, (2000), p. 55–124, Academic Press.

Shin, et al., "*meso*–Aryl–Substituted Expanded Porphyrins", *J. Am. Chem. Soc.,* vol. 123, (2001), pp. 7190–7191, American Chemical Society.

Sun, et al., "Characterization of the Third–Order Nonlinearity of [(CH$_3$–TXP)Cd]Cl", *SPIE,* vol. 3798, (1999), pp. 107–116, SPIE—The International Society for Optical Engineering.

Sun, et al., "Investigation of relationship between chemical structures and optical limiting properties of pentaazadentate porphyrin–like metal complexes", *SPIE,* vol. 3472, (1998), pp. 127–134, SPIE—The International Society for Optical Engineering.

Sun, et al., "Third–order susceptibilities of a symmetric pentaazadentate porphyrin–like metal complexes", *Applied Physics Letters,* vol. 74, No. 22, (1999), pp. 3254–3256, American Institute of Physics.

Sun, et al., "Third–order nonlinear optical properties of an expanded porphyrin cadmium complex",*Applied Physics Letters,* vol. 77, No. 12, (2000), pp. 1759–1761, American Institute of Physics.

Tohda, et al., "Liquid membrane electrodes for nucleotides based on sapphyrin, cytosine–pendant triamine and neutral cytosine derivative as sensory elements", *Sensors and actuators B,* vol. 13–14, (1993), pp. 669–672, Elsevier Science SA.

Umezawa, et al., "Expanded porphyrin incorporated solvent polymeric membrane electrodes: protonation and interaction with an analyte anion at organic/water interface as studied by optical second harmonic generatin and Fourier transform infrared attenuated total reflectance spectrometry", *Analytica Chimica Acta,* vol. 426, (2001), pp. 19–32, Elsevier Science BV.

Vogel, et al., "New Porphycene Ligands: Octaethyl– and Etioporphycene (OEPc and EtioPc)–Tetra– and Pentacoordinated Zinc Complexes of OEPc",*Angew. Chem. Int. Ed.,* vol. 32, No. 11, (1993), pp. 1600–1604, VCH Verlagsgesellschaft mbH.

Weghorn, et al., "Bis[($\mu$–chloro)copper(II)] Amethyrin: A Bimetallic Copper(II) Complex of an Expanded Porphyrin", *Inorg. Chem.,* vol. 35, (1996), pp. 1089–1090, American Chemical Society.

Seidel, et al., "Cycl[8]pyrrole: A Simple–to–Make Expanded Prophyrin with No Meso Bridges"; (2002), pp. 1480–1483; Wiley–VCH Verlag GmbH, 69451 Weinheim, Germany; Angew. Chem. 114, Nr.8.; published online Apr. 16, 2002.

PCT search report dated Jul. 4, 2003 for related application PCT/US03/06114.

* cited by examiner

CYCLO[N]PYRROLES AND METHODS THERETO

The present application claims the benefit of U.S. Ser. No. 60/359,752 filed Feb. 26, 2002, incorporated by reference herein.

The government owns certain rights in the present invention pursuant to grant number CHE 0107732 from The National Science Foundation and DOE grant number DE-FG 03-01ER-115186 from The Department of Energy.

FIELD OF INVENTION

The present invention relates generally to the fields of expanded porphyrins, infrared filters, non-linear optical materials, separation technology, and biomedical applications such as dialysis and drug delivery. More particularly, it concerns novel macrocycles termed cyclo[n]pyrroles and uses thereof.

BACKGROUND OF THE INVENTION

Porphyrin, a tetrapyrrolic macrocycle, is the active component of many naturally occurring pigments and has been known and studied for centuries; its biological importance can hardly be overestimated. In spite of this ubiquity, it was only in 1966 that the first expanded porphyrin analogue, sapphyrin, was reported and it has only been in recent years that the area of expanded porphyrin research has begun to attract attention as its own rapidly evolving field. One of the unexpected surprises to emerge from this work is the finding that large expanded porphyrins, those containing 6 to 8 or more pyrroles, are often not flat but rather adopt "figure eight" and other twisted conformations in spite of being highly conjugated. Because of this, it remains a challenge at present to produce large aromatic expanded porphyrins that display the classic disk-like structure of simple porphyrins.

One approach to obtaining large, flat expanded porphyrins is to invert one or more of the pyrrolic rings such that a compound lacking the classic "all-NH-in" structure of porphyrins is produced. To date, however, the preparation of higher order fused oligopyrrolic systems, including α-α' unsubstituted quaterpyrroles, has proved elusive. For a summary of expanded porphyrins and their heterologs, see Jasat A. and D. Dolphin in Chemical Reviews, 1997, Vol 97:6, 2267–2340. Cyclo[n]thiophenes (with n=12, 16, 18) have been reportedly synthesized. In spite of their 4n π-electron conjugation pathways, these systems did not display much in the way of obvious ring current effects (J. Krömer, et al., Angew. Chem. 2000, 112, 3481; Angew. Chem. Int. Ed. Engl. 2000, 39, 3481). The synthesis strategy used is limited to rings having at least 12 members, and all nitrogen-containing macrocycles are not possible using the cyclo[n]thiophene synthesis method.

The present invention also relates to complexation and recognition of anions. Anions play essential roles in biological processes; indeed, it is believed that they participate in 70% of all enzymatic reactions. A number of research groups have followed Nature's lead and have designed and synthesized receptors that use hydrogen bonds alone, or in concert with electrostatic interactions, to coordinate to anions. Nonetheless, there remains at present a critical need for additional anion complexing agents that are either easy to make or inherently selective in their substrate binding properties. Current technology for dialysis in medical applications relies on membranes, such as microfiltering cellophane, to filter anions such as chloride anion or phosphate-containing anions from the blood stream. Aluminum hydroxide or calcium carbonate cocktails must be consumed by the dialysis patient in order to bind the anionic species. A major drawback of this technology is that aluminum builds up in cellular membranes to toxic levels over time causing ailments including dementia and death. Calcium carbonate offers a less toxic substitute, however, it is less efficient and is associated with hypercalcemia.

Water-soluble anion binding agents are desired as drug delivery agents. For example, many anti-viral drugs only show activity when phosphorylated. However, many phosphorylated drug derivatives are too polar to pass through cell wall membranes. A water-soluble anion binding agent may be able to encapsulate the negative charge and so allow the drug to pass through cell walls. The synthesis of new molecular devices designed to sense and report the presence of a particular substrate is an area of analytical chemistry that is attracting attention. The detection of anionic species is a particular challenge, as anions are difficult to bind and are generally larger than cations leading to a smaller charge-to-radius ratio. Sensors that allow for the detection of biologically important anions such as chloride, phosphate, sulphate, and fluoride via colorimetric or spectroscopic means without interference from endogenous chromophores would be particularly useful in the area of medical analysis. The present invention relates to the development of such sensors.

The present invention also relates to cation binding agents useful as sensors for particular cations or as sequestering agents. Particular cation-complexes may be useful in medicine as imaging agents or in the treatment of disease.

Currently, the ability to translate, amplify, and direct digital traffic depends in part on nonlinear optical (NLO) materials. Thus, materials with nonlinear optical properties are valued as optical switches in fiberoptic communications systems. The most popular NLO materials have been brittle ceramics, such as LiNbO3. Organic materials that could be poured or molded into a shape, such as polymers, would offer advantages such as exceptional optical qualities, low cost, and ease of fabrication into device structures. Such materials could include molecular fragments displaying NLO activity, or highly colored chromophores, dissolved in or covalently attached to a polymeric host material or incorporated into liquid crystals. A material suitable for widespread industrial use has yet to be synthesized, however.

The present invention also relates to optical filters, particularly, infrared filters. New materials are needed that possess absorption in the infrared range while displaying transparent properties in the visible range.

The present inventors addressed the problem of producing large aromatic expanded porphyrins that display the classic disk-like structure of simple porphyrins and provide herein novel molecules that possess such disk-like structures as well as properties that address unmet needs in areas cited above.

SUMMARY OF THE INVENTION

The present invention results from the inventors' discovery of an efficient one-step synthesis of cyclo[n]pyrrole macrocycles using an oxidant and readily accessible α,α'-unsubstituted bipyrroles as the precursor. Several such macrocycles have been synthesized as provided herein. "Cyclo[n]pyrrole," as used herein, means a bridged or unbridged macrocycle having "n" pyrrole rings covalently linked in the α positions, and having no meso-carbon atoms. In particular, a composition comprising a cyclo[n]pyrrole having no meso carbon atoms where n is 6, 7, 8, 9, 10, 11, or 12 is an embodiment of the invention. Further, a composition comprising a bridged cyclo[n]pyrrole having no meso carbon atoms where n is 6, 8, 10, or 12 is an embodiment of the invention.

An embodiment of the invention is a compound comprising a cyclo[n]pyrrole macrocycle having structure I:

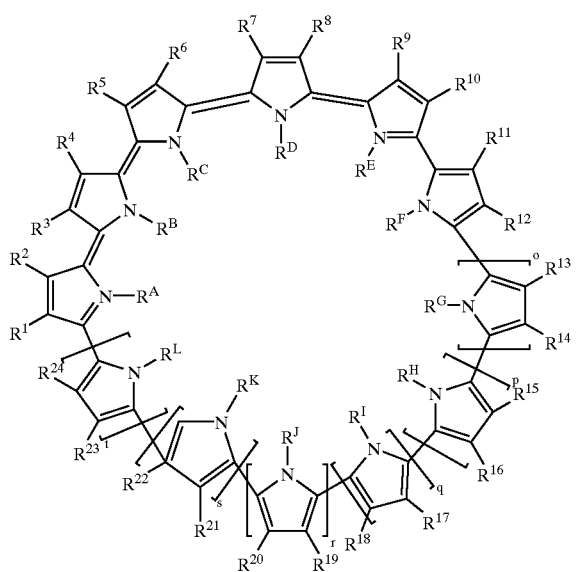

I wherein n is 6, 7, 8, 9, 10, 11, or 12. When n is 6; o=p=q=r=s=t=0, numbered R substituents are independently as listed in paragraph i) below, and $R^A$–$R^F$ are independently substituents as listed in paragraph ii) below. When n is 7; o=1, p=q=r=s=t=0, numbered R substituents are independently as listed in paragraph i) below, and $R^A$–$R^G$ are independently substituents as listed in paragraph ii) below. When n is 8; o=p=1, q=r=s=t=0, numbered R substituents are independently as listed in paragraph i) below, and $R^A$–$R^H$ are independently substituents as listed in paragraph ii) below. When n is 9; o=p=q=1, r=s=t=0, numbered R substituents are independently as listed in paragraph i) below, and $R^A$–$R^I$ are independently substituents as listed in paragraph ii) below. When n is 10; o=p=q=r=1, s=t=0, numbered R substituents are independently as listed in paragraph i) below, and $R^A$–$R^J$ are independently substituents as listed in paragraph ii) below. When n is 11; o=p=q=r=s=1, t=0, numbered R substituents are independently as listed in paragraph i) below, and $R^A$–$R^K$ are independently substituents as listed in paragraph ii) below. When n is 12; o=p=q=r=s=t=1, numbered R substituents are independently as listed in paragraph i) below, and $R^A$–$R^L$ are independently substituents as listed in paragraph ii) below:

i) hydrogen, alkyl, alkenyl, alkynyl, aryl, alkylaryl, formyl, acyl, hydroxyalkyl, hydroxyalkoxy, hydroxyalkenyl, hydroxyalkynyl, saccharide, carboxy, carboxyalkyl, carboxyamide, carboxyamidealkyl, alkyl sulfoxide, alkyl sulfone, alkyl sulfide, tetrahydropyran, tetrahydrothiapyran, thioalkyl, haloalkyl, haloalkenyl, haloalkynyl, alkyl ester, a site-directing molecule, a catalytic group, a reporter group, a binding agent, or a couple that is coupled to a site-directing molecule, to a catalytic group, to a reporter group, or to a binding agent;

ii) a pair of electrons, hydrogen, alkyl, aminoalkyl, alkylsulfone, carboxy alkyl, carboxyamidealkyl, phospho alkyl, alkyl sulfoxide, alkyl sulfone, alkyl sulfide, haloalkyl, aryl, N-oxide, dialkylamino, carbamate, or arylsulfonyl.

Alternatively, at least two substituents are coupled to form a linked structure, and when coupled to form a linked structure, nonlinked substituents are as defined supra in paragraph i) or ii). In a linked embodiment, the compound has at least one R substituent coupled to another R substituent within the same compound or an R substituent from a second compound to form a linked structure. When coupled to form a linked structure, nonlinked substituents are as defined.

Cyclo[n]pyrrole macrocycles may exist in a variety of oxidation states as described further under the detailed description infra.

A further aspect of the invention is a compound comprising a bridged cyclo[n]pyrrole macrocycle having structure II:

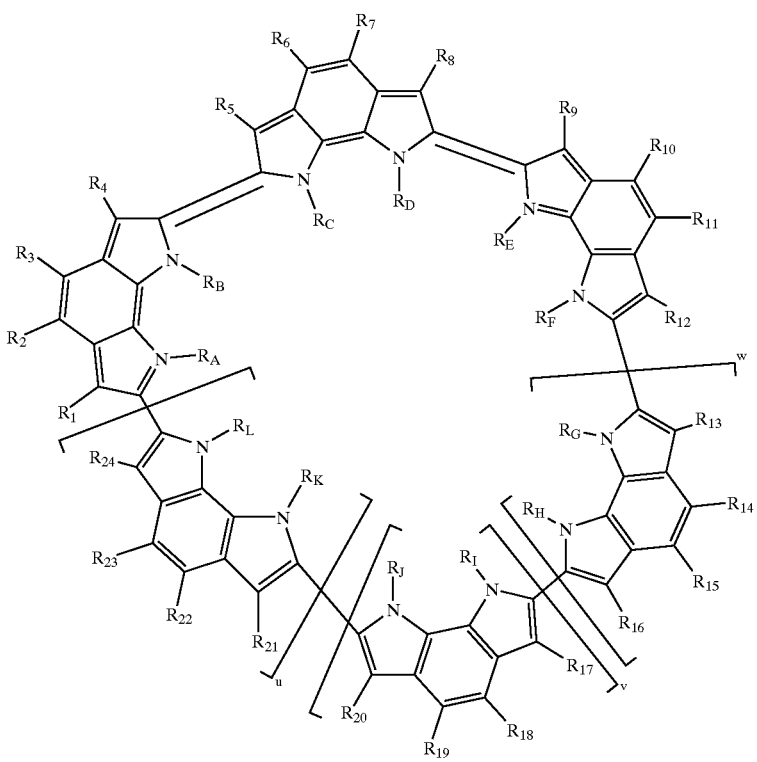

II wherein n is 6, 8, 10, or 12. When n is 6; w=v=u=0, numbered R substituents are independently as listed in paragraph i) supra, and $R_A$–$R_F$ are independently substituents as listed in paragraph ii) supra. When n is 10; w=v=1, u=0, numbered R substituents are independently as listed in paragraph i) supra, and $R_A$–$R_J$ are independently substituents as listed in paragraph ii) supra. When n is 12; w=v=u=1, numbered R substituents are independently as listed in paragraph i) supra, and $R_A$–$R_L$ are independently substituents as listed in paragraph ii) supra.

Alternatively, at least two substituents are coupled to form a linked structure, and when coupled to form a linked structure, nonlinked substituents are as defined supra in paragraph i) or ii). In a linked embodiment, the compound has at least one R substituent coupled to another R substituent within the same compound or an R substituent from a second compound to form a linked structure. When coupled to form a linked structure, nonlinked substituents are as defined.

Macrocycles of the present invention have unexpected properties that make them particularly useful. X-ray diffraction analysis of a cyclo[8]pyrrole dihydrogen sulfate salt demonstrated a very flat, essentially planar macrocyclic system with the sulfate centrally bound within the cavity, demonstrating anion binding. Cyclo[n]pyrroles bind anions in solution (Example 4) and in the solid state (Example 1) in such a manner that separation of the anions from a mixture of anions occurs. The macrocycles are expected to bind neutral molecular species to provide for separation of such molecules as well. Further, the affinity a macrocycle has for a particular species can be "tuned" by strategic choice of electron-donating or electron-withdrawing peripheral substituents for synthesis of the macrocycle. It is also expected that the affinity of cyclo[n]pyrroles can be tuned by varying n. Applications of these properties for removal of biological ions or neutral molecule species for medical uses, or removal of undesirable ions or neutral molecule species from environmental sources provide only a few of the practical and important uses for the present molecules.

A cyclo[n]pyrrole macrocycle noncovalently-complexed to a molecular or ionic species is an embodiment of the present invention. "Noncovalently-complexed to a molecular or ionic species," as used herein, means that bound molecules are held to the core of a macrocycle by noncovalent binding to one or more pyrrolic N—H groups thus forming a supramolecular ensemble. "Noncovalent binding" includes intermolecular interactions such as hydrogen bonds, dipole-dipole interactions, dipole-induced dipole interactions, ion-dipole interactions, ion pairing, van der Waals interactions, London dispersion forces, π—π stacking interactions, edge-to-face π-interactions, cation-π interactions, charge transfer interactions, or entropic, hydrophobic or solvophobic effects. In a preferred embodiment of the invention, the ionic species is an anionic species. "Supramolecular" as used herein describes the chemistry of complexes, that is molecular ensembles containing more than one atomic, ionic, or molecular component. Thus complexes of the macrocycles of the present invention and an ion or neutral molecule are considered to be supramolecular complexes or ensembles.

A cyclo[n]pyrrole macrocycle attached to a solid support is a particularly useful embodiment of the present invention. In particular, a chromatography column comprising a solid support bound to a cyclo[n]pyrrole is an aspect of the present invention. As in chromatography with calix[n]pyrroles, the basis of the chromatographic purifications effected by cyclo[n]pyrrole-derived chromatography columns are noncovalent interactions, primarily those involving hydrogen bonding. An advantage of the larger macrocycles is that they are expected to show enhanced binding properties with large- or poly-anions and have the property of binding more than one anion simultaneously.

A chiral cyclo[n]pyrrole is a further embodiment of the present invention. A chiral cyclo[n]pyrrole is expected to have different binding properties for each of a pair of enantiomeric species, thus allowing preferential binding of a particular enantiomer.

A further composition of matter of the present invention is a cyclo[n]pyrrole made by any synthetic method provided herein.

A method for separating a first molecule, a first anion, or first cation from a mixture of a first molecule, a first anion or a first cation and other species, comprising obtaining a cyclo[n]pyrrole-derivatized solid support; contacting the solid support with the mixture of molecules, anions or cations wherein binding occurs between the first molecule, the first anion, or the first cation and the cyclo[n]pyrrole-derivatized solid support; and removing unbound molecules to separate the first molecule, the first anion or the first cation from the mixture. Another method of separating includes batch processing where a macrocycle of the present invention attached to a solid support is added to a mixture containing the ion or molecule to be separated, and separating the macrocycle-molecule, macrocycle-ion, solid support-macrocycle-ion or solid support-macrocycle-molecule complex.

A method of removing an anion from an environment containing the anion comprising contacting the environment with a cyclo[n]pyrrole wherein the cyclo[n]pyrrole binds the anion thereby removing the anion from the environment is an aspect of the present invention.

A further aspect of the invention is a method for extracting an ion pair having a cation associated with an anion from an environment containing said ion pair, the method comprising contacting the environment with an anion coextractant and a cation coextractant, wherein the anion coextractant is a cyclo[n]pyrrole and wherein the cyclo[n]pyrrole binds the anion and the cation coextractant binds the cation thereby allowing for removal of the ion pair from the environment. In certain embodiments, the ion pair is an environmental pollutant or an amino acid zwitterion.

A further embodiment of the present invention is an electropolymerizable cyclo[n]pyrrole useful for constituting modified electrodes for the detection of ionic or molecular species.

A further embodiment of the present invention is an anion-, cation-, or neutral molecule-selective electrode comprising a conductive body, a polymer, and a cyclo[n]pyrrole. The cyclo[n]pyrrole may be electropolymerized and form the conductive body.

A method of electrochemical detection of an anion, a cation, or a neutral molecule comprising assembling an anion-, cation-, or neutral molecule-selective electrode and contacting the electrode with a solution of the anion, the cation, or the neutral molecule, and detecting the presence or absence of the anion, the cation, or the neutral molecule is an embodiment of the present invention.

A method of binding a cation comprising contacting the cation with a cyclo[n]pyrrole having a cation-binding functionality is also an aspect of the invention.

A method of removal of pertechnetate from pertechnetate-containing nuclear waste comprising contacting the waste with a cyclo[n]pyrrole to form a cyclo[n]pyrrole-pertechnetate complex; and removing the complex from the waste is also an aspect of this invention.

Use of a cyclo[n]pyrrole in the preparation of a pharmaceutical composition for use in in vivo or ex vivo diagnosis or treatment of body tissues is another embodiment of the invention. Use in diagnosis or treatments that involve the binding, transport, and/or removal of ions or neutral molecular species for conditions such as gout, for kidney dialysis, for removal of viruses, for introduction of antiviral drugs, or the like are also an aspect of this invention. A method, therefore, includes administering to a patient in need thereof a therapeutically effective amount of a cyclo[n]pyrrole to detect or treat a diseased condition.

A method of imaging a subject, the method comprising administering a detectable cyclo[n]pyrrole to the subject; and observing the subject wherein the detectable cyclo[n]pyrrole is fluorescent and the observing is by fluorescence, or the detectable cyclo[n]pyrrole is complexed with a paramagnetic metal cation and observing is by magnetic resonance imaging, or the detectable cyclo[n]pyrrole is complexed with an emitter and observing is by x-ray imaging, or gamma-ray detection or PET is an embodiment of the invention.

The bis chloride salt of cyclo[6]pyrrole shows absorption maxima at 397, 708 and 792 nm while the free base species exhibits absorption maxima at 372 and 841 nm. In one embodiment, the protonated form is provided for carrying out photodynamic therapy due to the extremely intense band at 792 nm ($\epsilon$=427,500 mol$^{-1}\bullet$L$^{-1}$).

The absorption maxima of the his chloride form of cyclo[7]pyrrole (429, 830 (shoulder), 943 nm) and the free base (385, 1016 nm) demonstrate a use particularly in optical imaging or photodynamic therapy.

The free base form of cyclo[8]pyrrole possesses absorption maxima at 349, 455, and 857 nm, and the protonated form possesses absorption maxima at 431 and 1112 nm. Both forms of the macrocycle are contemplated for use in optical imaging or photodynamic therapy. However, energetic considerations suggest that the free base form of cyclo[n]pyrrole is more suitable for photodynamic therapy.

A method for treating a subject having diseased tissue responsive to photodynamic therapy, the method comprising administering a photosensitive cyclo[n]pyrrole to the subject; and photoirradiating the diseased tissue, is a further aspect of the invention. Such photoirradiation is of sufficient intensity and energy to elicit a diagnostic or therapeutic response.

Protonated forms of the cyclo[8]pyrrole macrocycle of the present invention possess an intense, red-shifted Q-type band at 1112 nm ($\epsilon$=132,200 mol$^{-1}\bullet$L$^{-1}$) and essentially no absorbance in the visible range (Example 5), demonstrating use in optical storage, infrared filters, infrared shields, as non-linear optical materials, or in signaling devices.

Use of cyclo[n]pyrrole as a nonlinear optical material, as an infrared filter or shield, as a laser hardening dye, or as an information storage medium is an embodiment of the present invention.

A method of filtering near infrared light from a light source including near infrared light, the method comprising placing an infrared filter that comprises a cyclo[n]pyrrole in the path of the light source is an aspect of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

DETAILED DESCRIPTION OF THE PREFERRED EMBODIMENTS

Figure 1:
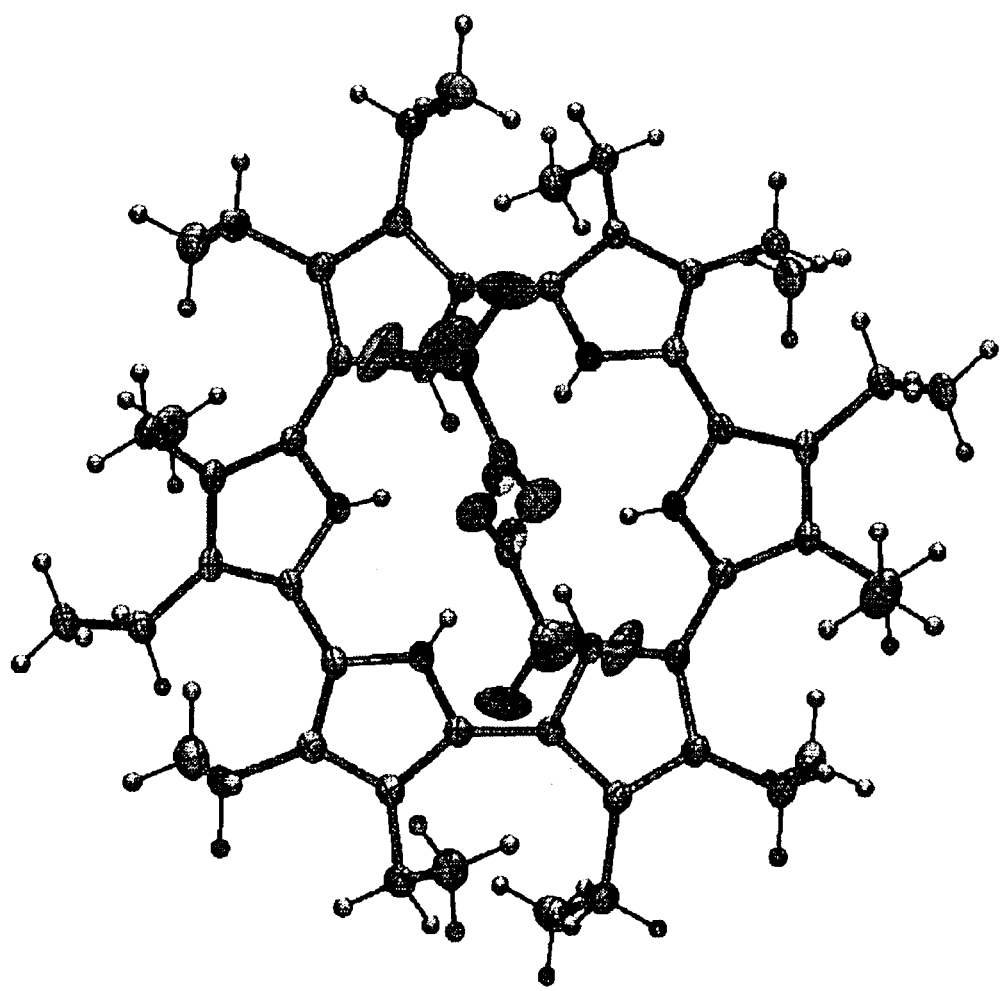
FIG. 1 illustrates an ORTEP-POV-Ray rendered view of the bis TFA salt of cyclo[6]pyrrole. The thermal ellipsoids are scaled to the 50% probability level. NH $\cdots$ O bonding interactions range from 2.05 to 2.78 Å.

The present invention provides an oxidative coupling procedure that allows efficient synthesis of novel cyclo[n]pyrrole macrocycles as well as a new synthesis method for existing macrocycles. The present invention provides cyclo[n]pyrroles where n is 6, 7, 8, 9, 10, 11, or 12, or bridged cyclo[n]pyrroles where n is 6, 8, 10, or 12, and derivatives, multimers, isomers, radical cations, radical anions, and ion and neutral molecule complexes thereof as new compositions of matter. The term "cyclo[n]pyrrole," as used herein, means both unbridged and bridged cyclo[n]pyrroles macrocycles.

These macrocyclic systems display features that are consistent with Hückel-type [4n+2] aromaticity. By changing the type of acid in the cyclization procedure, different yields of various cyclo[n]pyrroles could be obtained, such as cyclo[6]pyrrole [0.0.0.0.0.0], cyclo[8]pyrrole [0.0.0.0.0.0.0.0] and cyclo[12]pyrrole [0.0.0.0.0.0.0.0.0.0.0.0].

Protonated forms of cyclo[7]- and cyclo[8]pyrrole display a gap of 600 and 700 nm, respectively, between strong Soret and Q-like absorption bands in the electronic spectrum, having no significant ground state absorption in the visible portion of the electronic spectrum. This property demonstrates the utility of cyclo[n]pyrroles as near infrared filters, as nonlinear optical materials or as hardening dyes for use in protecting against optical damage in military applications. Further, the molecules of the present invention display properties useful as liquid crystalline dyes or DVD-type electronic media storage.

The molecules of the present invention bind anions, cations, and neutral molecules, and are useful as binding agents, as well as useful in photodynamic therapy as photosensitizers for treatment of cancer or cardiovascular disease, and as fluoresent indicators, for example. The red-shifted nature of the absorption and emission bands of the molecules of the present invention makes the invention superior to existing molecules for these uses.

The cyclo[n]pyrroles of the present invention contain no meso bridging carbon atoms. While certain prior art expanded porphyrin macrocycles contain bipyrrollic or terpyrollic units such as sapphyrins, amethyrins, rosarins, orangarins, or rubyrins, for example, no existing expanded porphyrin lacks all meso carbons. Lack of such carbons renders the macrocycle very stable.

Cyclo[n]pyrroles of the present invention differ from calix[n]pyrroles since calix[n]pyrroles have "n" pyrrole rings linked in the a positions via $sp^3$ hybridized meso-carbon atoms that are not bound to hydrogen (protium), deuterium or tritium atoms. A cyclo[n]pyrrole is different from a porphyrinogen since a porphyrinogen has one or more $sp^3$ hybridized meso-carbon atoms bound to a hydrogen (protium), deuterium or tritium atom. A cyclo[n]pyrrole is different from a porphomethene since a porphomethene contains three $sp^3$ hybridized meso-carbons and one $sp^2$ hybridized meso-carbon. A cyclo[n]pyrrole is different from a phlorin since a phlorin contains one $sp^3$ hybridized meso-carbon and three $sp^2$ hybridized meso-carbons. A cyclo[n]pyrrole is different from a porphyrin since a porphyrin contains four $sp^2$ hybridized meso-carbons. A cyclo[n]pyrrole is different from an expanded porphyrin since an expanded porphyrin contains at least one $sp^2$ hybridized meso-carbon.

Specific anions bound by macrocycles of the present invention include, for example, sulfates and phosphates. Further anions expected to be bound by cyclo[n]pyrroles are halide anions, carboxylates, oxalates, terephthalates, phospholipids, nucleotides, oligonucleotides, DNA, RNA, anionic polyoxometalates, or oxoanions such as pertechnetate, for example. Size and charge of the anion are not expected to be limiting factors in the type of anion that may be bound, although they are expected to determine selectivity for a given cyclo[n]pyrrole.

The term "molecular species" as used herein, means a neutral molecule, and represents a variety of classes of molecules since the macrocycles of the present invention provide different sizes of cavities and varieties of donor and acceptor sites. Specific neutral molecules include, but are not limited to, alcohols, polyalcohols, ketones, polyketones, phenols, polyhydroxylated aliphatic and aromatic compounds, amino compounds, amino acids, urea, guanidine, saccharides, biologically important polymers like proteins derivatives, and the like. Additionally, neutral molecules include, but are not limited to, ion pairs such as NaCl, CsI, or any grouping of ions which is neutral overall, or zwitterionic species such as amino acids and the like.

Specific cations include, but are not limited to, Group 1 metals, Group 2 metals, transition metals, post-transition metals, lanthanides, actinides, ammonium, alkylammonium, arylammonium, hydroxonium and guanidinium.

Carbon atoms in pyrrole rings are referred to as α (alpha) or β (beta); α carbons are adjacent to the NH group and β-carbons are adjacent to the α-carbons. In an alternative designation, the nitrogen atom is labelled 1 and the other atoms are numbered sequentially starting from an adjacent carbon atom. Thus, the α-carbons are also referred to as atoms 2 and 5 and the β-carbons as atoms 3 and 4.

Oxidation States. Cyclo[n]pyrroles may exist in a variety of different oxidation states. For example, cyclo[8]pyrrole may exist in any one of five oxidation states shown infra. Each of the different oxidation states may display different properties in terms of the herein stated applications. Each oxidation state may display different protonation states. For example, while A cannot be protonated, B can be either neutral, or mono- or diprotonated, C can be neutral, or mono-, di-, tri-, or tetraprotonated, D can be neutral, or from mono- up to hexaprotonated, E can be neutral, or from mono- up to octaprotonated.

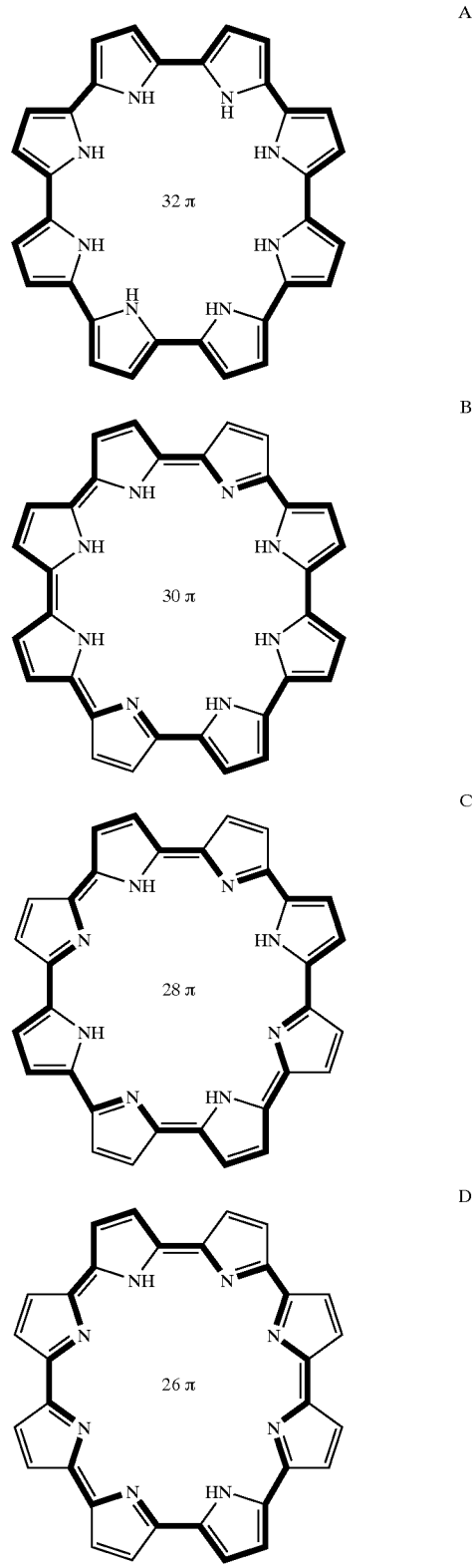

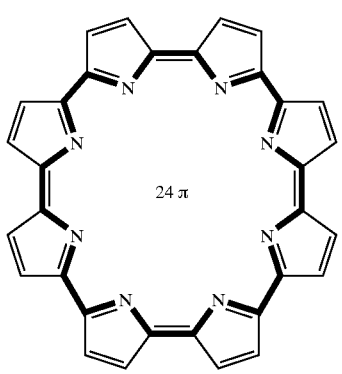

E

24 π

Analogous oxidation states can be drawn for other cyclo[n]pyrroles. The nature of the substituents and/or metallation of the cyclo[n]pyrroles may fine-tune the ease of oxidation/reduction of these species.

Oxidation states for cyclo[n]pyrrole macrocycles are as follows: when n is 6, a charge on the core macrocycle having no peripheral (i.e., beta carbon) substituents is an integer ranging from −6 to +6; when n is 7, a charge on the core macrocycle having no peripheral (i.e., beta carbon) substituents is an integer ranging from −7 to +6; when n is 8, such a charge on the core macrocycle is an integer ranging from −8 to +8; when n is 9, such a charge is an integer ranging from −9 to +8; when n is 10, such a charge is an integer ranging from −10 to +10; when n is 11, such a charge is an integer ranging from −11 to +10; and when n is 12, such a charge is an integer ranging from −12 to +12. One of skill in the art would realize in light of the present disclosure that the charge on a cyclo[n]pyrrole macrocycle is the charge on the core as stated above as modified by any charged substituent, such as a polyamine which would add positive charges or such as an oligonucleotide which would add negative charges, for example.

Oxidation states for bridged cyclo[n]pyrrole macrocycles are as follows: when n is 6, a charge on the core macrocycle having no peripheral (i.e., beta carbon) substituents is an integer ranging from −6 to +6; when n is 8, a charge on the core macrocycle having no peripheral (i.e., beta carbon) substituents is an integer ranging from −8 to +8; when n is 10, such a charge on the core macrocycle is an integer ranging from −10 to +10; and when n is 12, such a charge is an integer ranging from −12 to +12. Positively or negatively charged substituents will affect the overall charge of the macrocycle.

Substituents for Macrocycles of the Present Invention. Representative examples of alkanes useful as alkyl group substituents of the present invention include straight-chain, branched or cyclic isomers of propane, butane, pentane, hexane, heptane, octane, nonane, and decane, with methane, ethane, propane, and cyclohexane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonene, and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne, and decyne, with ethyne and propyne being preferred. Alkynyl groups having up to about thirty, or up to about fifty carbon atoms, and having up to about five or up to about three triple bonds are contemplated in the present invention.

The aryl may be a compound whose molecules have the ring structure characteristic of benzene, naphthalene, phenanthrene, anthracene, and the like, i.e., either the 6-carbon ring of benzene or the condensed 6-carbon rings of the other aromatic derivatives, or a compound whose molecules have the ring structure characteristic of pyridine i.e., a 5-carbon-1-heteroatom ring, or pyrrole i.e., 4-carbon-1-heteroatom ring such as, but not limited to, pyrrole, furan, or thiophene or the condensed 5-or 6-atom rings of the other aromatic derivatives. For example, an aryl group may be phenyl or naphthyl, and the terms used herein include both unsubstituted aryls and aryls substituted with one or more nitro, carboxy, sulfonic acid, hydroxy, oxyalkyl or halide substituent. Purine or pyrimidine molecules are included as "aryl" molecules. In this case, the substituent on the phenyl or naphthyl may be added in a synthetic step after the condensation step which forms the macrocycle.

Among the halide substituents, chloride, bromide, fluoride and iodide are contemplated in the practice of this invention. Representative examples of haloalkyls used in this invention include halides of methane, ethane, propane, butane, pentane, hexane, heptane, octane, nonane and decane, with halides, preferably chlorides or bromides, of methane, ethane and propane being preferred.

Representative examples of haloalkenyls used in this invention include halides of methene, ethene, propene, butene, pentene, hexene, heptene, octene, nonene and decene, with halides, preferably chlorides or bromides, of methene, ethene and propene being preferred. Representative examples of haloalkynyls used in this invention include halides of methyne, ethyne, propyne, butyne, pentyne, hexyne, heptyne, octyne, nonyne and decyne, with halides, preferably chlorides or bromides, of methyne, ethyne and propyne being preferred.

"Hydroxyalkyl" means alcohols of alkyl groups. Preferred are hydroxyalkyl groups having one to twenty, more preferably one to ten, hydroxyls. "Hydroxyalkyl" is meant to include glycols and polyglycols; diols of alkyls, with diols of C1–10 alkyls being preferred, and diols of C1–3 alkyls being more preferred; and polyethylene glycol, polypropylene glycol and polybutylene glycol as well as polyalkylene glycols containing combinations of ethylene, propylene and butylene.

Representative examples of alkoxys include the alkyl groups as herein described having ether linkages. "Alkoxy" is meant to include polyethers with one or more functional groups. The number of repeating alkoxys within a substituent may be up to 200, preferably is from 1–20, and more preferably, is 1–10, and most preferably is 1–5. A preferred alkoxy is $O(CH_2CH_2O)_xCH_3$ where x=1–100, preferably 1–10, and more preferably, 1–5.

"Crown ether" means a cyclic polyether with repeating alkoxy groups. They are named according to the number of atoms and the number of oxygens in the cycle. S-crown-T is a cyclic polyether containing S atoms and T oxygen atoms. Preferred are crown ethers containing one to twenty oxygen atoms, more preferably one to ten. Representative examples include, but are not limited to, 12-crown-4, 15-crown-5, benzo-15-crown-5, 18-crown-6, benzo-18-crown-6, 21-crown-7, 24-crown-8, dibenzo-18-crown-6, as well as aza crowns and thia crowns having one or more oxygen atoms replaced by a nitrogen or sulfur, and functionalized derivatives thereof.

"Hydroxyalkenyl" means alcohols of alkene groups. Preferred are hydroxyalkenyl groups having one to twenty, more preferably one to ten, hydroxyls.

"Hydroxyalkynyl" means alcohols of alkyne groups. Preferred are hydroxyalkenyl groups having one to twenty, more preferably one to ten, hydroxyls.

"Hydroxyalkoxy" means alkyl groups having ether or ester linkages, hydroxyl groups, substituted hydroxyl groups, carboxylic acid groups, substituted carboxy groups or the like.

Representative examples of thioalkyls include thiols of ethane, thiols of straight-chain, branched or cyclic isomers of propane, butane, pentane, hexane, heptane, octane, nonane and decane, with thiols of ethane (ethanethiol, $C_2H_5SH$) or propane (propanethiol, $C_3H_7SH$) being preferred. Sulfate-substituted alkyls include alkyls as described above substituted by one or more sulfate groups, a representative example of which is diethyl sulfate (($C_2H_5)_2SO_4$).

"Alkylsulfoxide" means alkyl groups having S=O groups. Preferred are alkylsulfoxide groups having one to twenty, more preferably one to ten, sulfoxides. Alkylsulfoxide is meant to include cyclic alkyl groups containing sulfoxide moieties.

"Alkylsulfone" means alkyl groups having $S(=O)_2$ groups. Preferred are alkylsulfone groups having one to twenty, more preferably one to ten, sulfones. Alkylsulfone is meant to include cyclic alkyl groups containing sulfone moieties.

"Alkylsulfide" means alkyl groups having S groups. Preferred are alkylsulfide groups having one to twenty, more preferably one to ten, sulfides. Alkylsulfide is meant to include cyclic alkyl groups containing sulfide moieties such as tetrahydrothiopyran derivatives.

Representative examples of phosphates include phosphate groups, polyphosphate groups, DNA, RNA, oligonucleotides and nucleotides. Representative examples of phosphate-substituted alkyls include alkyls as described above substituted by one or more phosphate or polyphosphate groups. Representative examples of phosphonate-substituted alkyls include alkyls as described above substituted by one or more phosphonate groups.

Representative examples of carboxy groups include carboxylic acids of the alkyls described above as well as aryl carboxylic acids such as benzoic acid and derivatives thereof. Representative examples of carboxyamides include peptides, proteins, primary carboxyamides ($CONH_2$), secondary (CONHR') and tertiary (CONR'R") carboxyamides where each of R' and R" is a functional group as described herein.

Representative examples of useful amines include a primary, secondary or tertiary amine of an alkyl or aryl as described herein.

"Carboxyamidealkyl" means alkyl groups with secondary or tertiary amide linkages or the like. "Carboxyalkyl" means alkyl groups having hydroxyl groups, carboxy or amide substituted ethers, ester linkages, tertiary amide linkages removed from the ether or the like.

The term "saccharide" includes oxidized, reduced or substituted saccharide; hexoses such as D- or L-glucose, D- or L-mannose or D- or L-galactose; pentoses such as D- or L-ribose or D- or L-arabinose; ketoses such as D- or L-ribulose or D- or L-fructose; disaccharides such as sucrose, lactose, or maltose; derivatives such as acetals, amines, and phosphorylated sugars; oligosaccharides or polysaccharides, such as aliginic acid as well as open chain forms of various sugars, and the like. Examples of amine-derivatized sugars are galactosamine, glucosamine, sialic acid and D- and L-glucamine derivatives such as 1-amino-1-deoxysorbitol.

By "reporter group" is meant a substituent that is fluorescent, chromophoric, electropolymerizable, redox-active, or optically active. Examples of a fluorescent reporter group include, but are not limited to, ruthenium(II) bipyridyl complexes, acetylnaphthalene, 9-aminoacridine, 9-phenylanthracene, benzimidazole, N-methylbenzo[b] carbazole, 2-phenylbenzoxazole, 1,1'-binaphthyl, fluorene, fluorescein dianion, indeno[2,1-a]indene, 2,5-diphenylfuran, perylene, 2-aminopurine, p-quatephenyl, 4,4'-diphenylstilbene, sapphyrins, texaphyrins, and dipyrrolylquinoxalines. Examples of a chromophoric reporter groups include isosulfan blue, fluoroscein, 2',7'-dichlorofluoroscein, rhodamine, carboxyrhodamine, dialkylaminocoumarin, erythrosin, pyrene, 9-(diethylamino)-5-octadecanoylimino-5H-benzo[a] phenoxazine, 5-octadecanoyloxy-2-(4-nitrophenylazo) phenol, 9-(diethylamino)-5-(2-naphtoylimino)-5H-benzo[a] phenoxazine, 4',5'-dibromoflurescein octadecyl ester, 2-(4-nitrophenylazo)chromotropic acid disodium salt, 2-(phenylazo)chromotropic acid disodium salt, 4,5-dihydroxynaphtalene-2,7-disulfonic acid disodium salt, 5,7-dihydroxyflavone, 5,7-dinitro-8-hydroxy-2-naphthalenesulphonic acid, 6,6'-[(3,3'-dimethyl[1,1'-biphenyl]4,4'-diyl)bis(azo)]bis[4-amino-5-hydroxy-1,3-naphthalenedisulfonic acid] tetrasodium salt, 4,5,6,7,-tetrachloro-3',6'-dihydroxy-2',4',5',7'-tetraiodospiro [isobenzofuran-1(3H),9'-[9H]xanthen]-3-one dipotassium salt, 3,7-bis(dimethylamino)phenothiazin-5-ium chloride, 3,6-bis(dimethylamino)acridine hydrochloride zinc chloride double salt (Acridine Orange), sapphyrins and texaphyrins. By "electropolymerizable" is meant a moiety that will polymerize when subjected to a particular voltammetric potential or a continuous scanning potential. Examples of an electropolymerizable group include, but are not limited to, α-free pyrroles, α-free thiophenes, anilines or vinyl groups. By "redox-active" is meant a moiety which can undergo an oxidation or a reduction process. Examples of a redox-active group include, but are not limited to, ferrocene, cobaltocenium, ruthenium(II) bipyridyl complexes, transition metals, fullerenes, porphyrins, expanded porphyrins and pyrroles.

In one embodiment of the present invention, a cyclo[n] pyrrole is further coupled to a site-directing molecule. "Site-directing" means having specificity for targeted sites. "Specificity for targeted sites" means that upon contacting the cyclo[n]pyrrole-conjugate with the targeted site, for example, under physiological conditions of ionic strength, temperature, pH and the like, specific binding will occur. The interaction may occur due to specific electrostatic, hydrophobic, or other interaction of certain residues of the conjugate with specific residues of the target to form a stable complex under conditions effective to promote the interaction.

Exemplary site-directing molecules contemplated in the present invention include but are not limited to: polydeoxyribonucleotides; polyribonucleotides; oligodeoxyribonucleotides; oligoribonucleotides; polyamides, including peptides having affinity for a biological receptor, and proteins such as antibodies; steroids and steroid derivatives; hormones such as estradiol, or histamine; hormone mimics such as morphine; and further macrocycles such as texaphyrins, sapphyrins, rubyrins, or calixpyrroles.

Representative examples of useful steroids include a steroid hormone of the following five categories: progestins (e.g. progesterone), glucocorticoids (e.g., cortisol), mineralocorticoids (e.g., aldosterone), androgens (e.g., testosterone) and estrogens (e.g., estradiol).

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen-, and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any naturally occurring or synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

The term "binding agent" means that upon contacting the binding agent with a guest species for binding under appropriate conditions of ionic strength, temperature, pH and the like, specific binding will occur. The interaction may alter the three-dimensional conformation and the function or activity of either or both the bound species and the receptor involved in the interaction. Preferred binding agents include a calix[n]pyrrole, a calix[m]pyridino[n]pyrrole, a calix[m] pyridine, a calixarene, a cation-binding functionality, a crown ether, a chelating group, a porphyrin, or an expanded porphyrin such as sapphyrin, rosarin, rubyrin, texaphyrin, amethyrin or turcasarin, or oligopyrroles.

Texaphyrin compounds, methods for making and methods for using them are described in U.S. Pat. Nos. 4,935,498; 5,162,509, 5,252,720, 5,272,142, 5,256,399, 5,292,414, 5,432,171, 5,439,570, 5,475,104, 5,451,576, 5,457,183, 5,369,101, 5,569,759, 5,559,207, 5,587,463, 5,594,136, 5,599,923 5,714,328, 5,776,925, 5,798,491 and 5,775,399, each patent is incorporated by reference herein.

Rubyrins are disclosed in U.S. Pat. No. 5,410,045, and turcasarins are disclosed in PCT publication WO 96/21665; the patent and PCT publication are incorporated by reference herein.

Sapphyrins are disclosed in U.S. Pat. Nos. 5,041,078; 5,159,065; 5,120,411; 5,302,714; 5,457,195; 5,530,123; 5,543,514; and 5,587,478; each patent is incorporated by reference herein.

Calixpyrroles are disclosed in U.S. Pat. No. 6,262,257, incorporated by reference herein.

A "catalytic group," as used herein, means a chemical functional group that may act as a general acid, Brønsted acid, Lewis acid, general base, Brønsted base, Lewis base, nucleophile, or any other means by which an activation barrier to reaction is lowered or the ground state energy of a substrate is increased. Exemplary catalytic groups contemplated include, but are not limited to, imidazole; guanidine; zinc coordinated to a nitrogen containing macrocycle, EDTA complexes, DTPA compleses, substituted saccharides such as a D-glucosamine, D-mannosamine, D-galactosamine, D-glucamine, and the like; amino acids such as L-histidine and L-arginine; derivatives of amino acids such as histamine; polymers of amino acids such as poly-L-lysine, (LysAla)$_n$, (LysLeuAla)$_n$ where n is from 1–30 or preferably 1–10 or more preferably 2–7 and the like. The catalytic group may be attached either directly to the cyclo[n]pyrrole or via a linker or couple of variable length.

A couple may be described as a linker, i.e. the covalent product formed by reaction of a reactive group designed to attach covalently another molecule at a distance from the cyclo[n]pyrrole macrocycle. Exemplary linkers or couples are amides, amine, disulfide, thioether, ether, ester, or phosphate covalent bonds.

In most preferred embodiments, conjugates and appended groups are covalently bonded to the cyclo[n]pyrrole via a carbon-carbon, carbon-nitrogen, carbon-sulfur, or a carbon-oxygen bond, more preferably a carbon-carbon, carbon-oxygen or a carbon-nitrogen bond.

Preferred embodiments of the present invention include a cyclo[n]pyrrole where n is 8 or 12 or where at least one substituent attached to a β-carbon is other than hydrogen, or at least one substituent attached to a β-carbon is carboxy, carboxyalkyl, ester or carboxyamide.

While cited cyclo[n]pyrroles are presently preferred for use in the present invention, the invention is not limited thereto and any cyclo[n]pyrrole may be used.

Synthetic Methods for Macrocycles of the Present Invention. In developing the synthesis scheme used herein in Example 1, the present inventors focused on a simple one-pot strategy that involved the direct coupling of bipyrrolic fragments. Accordingly, several readily available substituted and unsubstituted bipyrroles were subject to a wide range of potential coupling conditions, including ones involving condensation of the bipyrrole with $SCl_2$ and subsequent sulfur extrusion of the putative thia-bridged macrocyclic intermediates, a Cr(VI) based oxidative coupling method, and strategies based on the use of DDQ and chloranil. The most successful coupling occurred using $FeCl_3$ as the oxidant. Ferric chloride has been used frequently in the synthesis of polypyrroles, but has not, to the best of the present inventors' knowledge, ever been used to produce expanded porphyrin-type coupling products. It has, however, been employed to aromatize macrocycles. In Example 1, a highly efficient one-step synthesis of cyclo[8] pyrroles based on the use of $FeCl_3$ as the oxidant in a solution of 1M sulfuric acid is provided. Using conditions as set forth in Example 1, the yields of cyclo[8]pyrroles, isolated in the form of their dihydrogen sulfate salts, are above 70% for certain macrocycles. Such yields are noteworthy in the area of expanded porphyrin chemistry and rival the best yields seen in the synthesis of β-substituted octaalkylporphyrins. Changing the acid in the cyclization method to 1M hydrochloric acid instead of sulfuric acid yields an amount of up to 15% cyclo[6]pyrrole and 5% cyclo[7]pyrrole.

An aspect of the invention is the direct coupling of bipyrrolic fragments with an oxidant. In addition to ferric chloride, other oxidants having sufficient oxidation-reduction potential to effect the oxidative coupling of pyrroles are contemplated as effective in the coupling reaction. Oxidants include inorganic oxidants (e.g. $Cu(OSO_2CF_3)$, $K_3Fe(CN)_6$, $Na_2Cr_2O_7 \cdot x\ H_2O$, $K_2Cr_2O_7 \cdot x\ H_2O$, $CrO_3$, $MnO_2$, $Pb(Oac)_4$, $KMnO_3$, $KClO_3$, $NaClO_3$, $KClO_4$, $NaClO_4$, $KIO_4$, $NaIO_4$, $SeO_2$, $I_2$, $Br_2$), hypervalent iodo-compounds (e.g. $PhICl_2$), peroxides (e.g. tert-butyl peroxide), or quinones (e.g. chloranil, DDQ), for example.

A further aspect of synthesizing the cyclo[n]pyrroles of the invention is the acid employed to dissolve the oxidant. In addition to sulfuric acid or hydrochloric acid, further acids for use in the invention are $HNO_3$, $HClO_4$, $H_3PO_4$, $H_2P_2O_7$, $F_3CSO_3H$, HCOOH, $CH_3COOH$, $F_3CCOOH$, and $HBF_4$, or a mixture thereof. Another aspect of the invention is the speed of addition of the bipyrrole to the biphasic mixture as well as the stirring speed of the reaction mixture. Higher adding speed of bipyrrole and higher stirring rates promote the formation of larger macrocycles, such as cyclo[12]pyrrole.

Cyclo[nt]pyrrole derivatives, multimers, and conjugates. Example 2 provides for the synthesis of derivatives, multimers or conjugates of cyclo[n]pyrroles. One skilled in the art of organic synthesis, in light of the present disclosure, could extend and refine the referenced basic synthetic chemistry to produce cyclo[n]pyrroles having various substituents. For example, polyether-linked polyhydroxylated groups, saccharide substitutions in which the saccharide is appended via an acetal-like glycosidic linkage, an oligosaccharide or a polysaccharide may be similarly linked to a cyclo[n]pyrrole. A carboxylated cyclo[n]pyrrole, in which the acid groups are linked to the cyclo[n]pyrrole core via aryl ethers or functionalized alkyl substituents could be converted to various amido products wherein the amide linkages serve to append further substituents. Saccharide moieties may be appended via amide bonds. With use of a carboxy derivative, there exist possibilities of substitution through various functional groups. Formation of an amide bond, for example, could lead to attachment of natural nucleotides as well as the "unnatural" nucleotide analogues. Using nucleotide-functionalized cyclo[n]pyrroles, it may be possible to do through-membrane transport of nucleotide analog drugs such as AZT, acyclovir, and the like. Using the case of cyclo[8]pyrrole by way of illustration, one skilled in the art in light of the present invention would appreciate that in addition to one carboxyl derivative, one may add two, three, four, five, six, seven, eight, or up to sixteen carboxylic acid groups at the β-positions of the cyclo[n]pyrrole. These carboxylic acid groups may be directly attached to the cyclo[n]pyrrole macrocycle or linked to it via various linkers such as methylene ($CH_2$) or ethylene ($CH_2CH_2$) bridges. Arrays of cyclo[n]pyrroles spanning membranes and acting as anion channels analogous to cation channels are contemplated by the present inventors. By using poly-amine-containing compounds, dimers, trimers and tetramers of cyclo[n]pyrrole could be used as carriers for transporting polyanionic species through aliphatic membranes. As shown in Example 2, cyclo[8]pyrrole shows an affinity for phosphate anions. With this in mind, arrays of cyclo[n]pyrroles could be used to encircle RNA and DNA molecules, thus providing anti-viral activity. Specificity of binding could be gained by attaching specific nucleotides to the cyclo[n]pyrrole oligomer. Attachment of known nucleotide cleaving agents such as Fe-EDTA could facilitate the site directed cleavage of RNA. With the addition of a cation-binding functionality, amino acid recognition and transport are possible. A solid silica-supported cyclo[n]pyrrole can be used for separation methods. The attachment of sugars, and mono- and polysaccharides to the cyclo[n]pyrrole could allow for recognition of compounds such as glucose-6-phosphate.

By attachment of a redox-active reporter group; cyclo[n]pyrrole macrocycles may function as potentiometric or amperometric sensors for cations, anions, or neutral molecules.

By attachment of a fluorophoric reporter group; cyclo[n]pyrrole macrocycles may function as fluorescent sensors for cations, anions, or neutral molecules.

By attachment of a chromophoric reporter group; cyclo[n]pyrrole macrocycles may function as chromophoric sensors for cations, anions, or neutral molecules.

Metal Cation Coordination. The present inventors expect that the cyclo[n]pyrroles will coordinate one or more metal cations, especially those of the actinide and lanthanide series of metals. Such metal coordination complexes are well known for expanded porphyrins, such as texaphyrins and amethyrins, for example.

An uncoordinated cyclo[n]pyrrole is mixed in an organic solvent with a metal salt and stirred at ambient temperature. Warming the reaction mixture, heating to reflux, adding a Brønsted base, and adding an oxidant, are techniques that may be advantageously employed. The metal salt may be, for example, gadolinium acetate tetrahydrate for forming the Gd(III) complex, europium acetate for forming the Eu(III) complex, samarium acetate for forming the Sm(III) complex, lutetium nitrate hydrate or lutetium acetate pentahydrate for forming the Lu(III) complex, or lanthanum nitrate hexahydrate for forming the La(III) complex, for example. The metal cation may be a singly charged metal cation such as Cu(I), Np(V)$O_2$, Pu(V)$O_2$, Ag(I), Au(I), or Tl(I). The metal cation may be a double charged metal cation such as Ca(II), Mn(II), Co(II), Ni(II), Zn(II), Cd(II), Hg(II), Fe(II), Sm(II), U(VI)$O_2$ or Pu(VI)$O_2$. The metal cation may be a trivalent metal cation such as Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), Au(III), Am(III), Cf(III), or U(III). The metal cation may be a tetravalent metal cation such as Th(IV) and U(IV). The metal cation may be a radioisotope, including but not limited to Th(IV), In-111(III), Y-90(III), U(III), U(IV), U(VI), Am(III), Np(V)$O_2$, Pu(V)$O_2$, or Pu(VI)$O_2$.

The present inventors expect that more than two metal cations may be simultaneously bound within a cyclo[n]pyrrole cavity. Cyclo[n]pyrroles having strongly bound metal cations are particularly useful in remediation, chemical catalysis, and in medical applications, whereas complexes having weakly bound metal cations are particularly useful as extractants.

The metal complexes may be associated with, depending on the metal, anywhere from 0–8 apical ligands about the encapsulated metal center or centers. The ligands are typically some combination of acetate, chloride, nitrate, hydroxide, water, or methanol and when bound, may be tightly complexed or readily dissociable.

Considerable effort has been devoted to the development of new potential MRI contrast agents. Most of this work has centered around preparing new complexes of Gd(III) since this cation, with 7 unpaired f-electrons, has a higher magnetic moment than other paramagnetic cations such as Fe(III) and Mn(II). Thus, complexes of Gd(III) would be expected to be superior relaxation agents than those derived from Mn(II) or Fe(III). In addition, both iron and, to a lesser extent, manganese are sequestered and stored very efficiently in humans (and many other organisms) by a variety of specialized metal-binding systems. Moreover both iron and manganese are capable of existing in a range of oxidation states and are known to catalyze a variety of deleterious Fenton-type free-radical reactions. Gadolinium(III), which suffers from neither of these deficiencies, thus appears to offer many advantages. As is true for Fe(III) and Mn(II), the aqueous solution of Gd(III) is too toxic to be used directly for MRI imaging at the 0.01 to 1 mM concentrations required for effective enhancement. Gd(III) forms only weak and/or hydrolytically unstable complexes with porphyrins. On the other hand, texaphyrin gadolinium complexes are stable for in vivo use and have proved to be effective contrast agents in imaging. However, texaphyrins pose considerable difficulty in synthesis, requiring up to fourteen reaction steps.

A cyclo[n]pyrrole complexed to a paramagnetic metal provides a new paramagnetic contrast reagent for use in imaging by magnetic resonance imaging. The paramagnetic metal cation may be Mn(II), Mn(III), Fe(III), or trivalent lanthanide metal cations other than La(III), Lu(III), and Pm(III). More preferably, the paramagnetic metal is Mn(II), Mn(III), Dy(III), or Gd(III); and most preferably, Dy(III) or Gd(III). The paramagnetic metal is preferably Gd(III).

A cyclo[n]pyrrole complexed to a diamagnetic metal is particularly preferred for generating singlet oxygen in photodynamic therapy protocols. The diamagnetic metal cation may be Lu(III), La(III), In(III), Y(III), Zn(II) or Cd(II), preferably the metal cation is Lu(III). A powerful technique is the use of cyclo[n]pyrrole in magnetic resonance imaging followed by photodynamic therapy in the treatment of diseased tissue, particularly atheroma, and benign and malignant tumors, for example.

Currently, 25–30% of the world's supply of electrical power is produced using nuclear source, and this is the dominant source of power for most of Europe. The applications of nuclear energy for the production of electricity both for general civilian use as well as in satellite and space exploration applications are plagued with waste management risks that must be addressed. Many of these center around the control, sensing, remediation, and storage of radioactive cations of the actinide series (abbreviated An), either in pure form or, more commonly, as complex mixtures generated during fission activities. These latter often involve a range of species, such as the trivalent lanthanides, that are chemically similar to the actinides. This has made the problem of actinide purification one of the most challenging known.

All isotopes of the actinide elements are radioactive. The half-lives of the most stable isotopes decrease across the series, with the heaviest members of the series being so unstable they can only be created and isolated a few atoms at a time. By contrast, 50 years of nuclear weapons production has generated more than 100 metric tons of purified plutonium in the United States and a similar amount in Russia. The production of plutonium from power reactors amounts to perhaps as much as 7000 metric tons worldwide, most of which is dilute and contained in spent reactor fuel. This large quantity is increasing daily.

As the result of 50+ years of research, it is now known that the actinides are easily hydrolyzed acidic metal ions that form strong complexes with common chelating agents. They prefer interactions with hard acid donor atoms like O and F, but demonstrate some covalency in their interactions with softer donor atoms such as Cl$^-$, N, and S, a key factor in their separation science. The actinides between U and Am have a moderately diverse redox chemistry, with four principal oxidation states (III, IV, V, VI and a heptavalent state for Np and possibly Pu). The penta- and hexavalent oxidation states exist as linear dioxocations, or "actinyl" cations, in most solutions and many solid media. This diverse redox chemistry is utilized in their chemical separation from reactor fuels. The transplutonium actinides have fewer oxidation states and generally behave quite similarly to the trivalent lanthanides (abbreviated Ln).

Because actinide production in reactors is accompanied by fission, the ability to isolate the transuranic actinides from the matrix that includes both fission products and uranium, remains a separation problem central to An production. Accordingly, efficient separation processes continue to be sought. The use of a BiPO$_4$ precipitation process, better than the original ether extraction/lanthanum fluoride precipitation first used to isolate plutonium, proved suitable for the rapid production of pure Pu demanded by the Manhattan project. This process suffered from the drawback of allowing valuable purified uranium to enter the process waste stream. It also only achieved 97–98% recovery of Pu.

The development of solvent extraction processes, first the REDOX process (based on extraction by methyl(isobutyl) ketone) and subsequently the PUREX process (relying on tributylphosphate as a selective extractant for uranium and plutonium) overcame these limitations to a considerable extent. They both rely on extraction of the Pu and subsequent reduction to the trivalent state, leaving the excess uranium in the extractant phase for subsequent recovery and recycle. Though the industry standard at present, the PUREX process remains far from perfect. It also does not address the isolation of other An cations.

UO2(VI)2+ Coordination. Starting from a free base cyclo[6]pyrrole, adding triethylamine and uranyl(VI)acetate, and heating to reflux several hours, the inventors were able to isolate a uranyl complex of cyclo[6]pyrrole in 25% yield (crystal structure FIG. 1). Therefore, cyclo[n]pyrroles are provided for coordinating actinide metals and use in radioactive waste remediation.

The successful coordination of Uranium(VI) into cyclo[6]pyrrole (see FIG. 1) is the first step to incorporate other radioactive actinyl cations for remediation and actinide/lanthanide separation as it is true for an hexapyrrolic macrocycle containing two bridging meso carbon atoms, isoamethyrin (hexaphyrin(1.0.1.0.0.0)), J. L. Sessler, et al. *Angew. Chem.* 2001, 113, 611–614; *Angew. Chem. Int. Ed., Engl.* 2001, 40, 591–594), for coordinating actinyl cations such as UO$_2^{2+}$ and NpO$_2^+$. The strong, nonlabile complexes could be useful in direct, coordination based remediation strategies. In general, cyclo[n]pyrroles could coordinate the radioactive cations in question and remove them from a waste stream when used in either a flow, mixing, or bulk contact manner. Cyclo[n]pyrroles of the present invention also have utility as potential actinide cation sensors since a change in color in the visible or near IR portions of the electronic spectrum is expected to accompany cation complexation. Weaker complexes, formed from the actinyl cations or from trivalent actinide cations are expected to prove useful in extraction-based purification strategies. Such strategies rely on contacting an extractant with an aqueous mixture of actinides and impurities from which they must be removed, typically trivalent lanthanide cations, and extracting one or more of the cations in question, either the targeted actinide cation or one or more of the impurities, preferentially into an organic phase. The cyclo[n]pyrroles, because they are easy to prepare and readily functionalized in ways that can improve their partition properties when applied as extractants are expected to prove advantageous as extractants for actinide cation purifications. Other attributes of the cyclo[n]pyrroles that make them potentially advantageous for applications are the fact that they are comprised entirely of environmentally benign carbon, nitrogen, and hydrogen atoms and that they may be readily protonated as a means of effecting metal release subsequent to extraction. The use of cyclo[n]pyrroles in radioactive cation remediation, sensing, and extraction applications are preferred embodiments of the present application.

Additionally, binding a cation comprising contacting the cation with a cyclo[n]pyrrole having a cation-binding functionality is an embodiment of this invention. A cation-binding functionality may be substituents on the periphery of the macrocycle.

Cyclo[n]pyrroles as separation media. A method of use of the present invention comprises separating a first molecule, a first anion or a first cation from a mixture of a first molecule, first anion or first cation, and other species, using a form of solid support-immobilized cyclo[n]pyrrole by contacting the solid support with the mixture to separate a first molecule, first anion or first cation from a mixture of first molecule, first anion or first cation and other species. Examples of solid supports include, but are not limited to, silica gel, aminopropyl silica gel, carboxylalkylated silica gels, chloromethylated silica gel, chloroalkylated silica gel, other functionalized silica gels, alumina, polyacrylamide polymer beads, polystyrene polmer beads, sepharose, sephadex, agarose, clays, zeolites, texaphyrins, sapphyrins, or calixpyrroles coupled to cyclo[n]pyrroles. Examples of forms of solid supports include, but are not limited to chromatography columns, thin-layer chromatographic supports, electrophoresis gels, or capillary electrophoresis tubes. Examples of ions or neutral molecules to be separated are neutral aromatic or aliphatic species (polymeric, oligomeric and monomeric), a polyhalobiphenyl (including polychlororbiphenyl), or anionic species (polymeric, oligomeric and monomeric) such as nucleotides, oligonucleotides, pertechnetate, polyoxometalates or inorganic phosphate.

The inventors' discovery that cyclo[n]pyrroles recognize and bind phosphate anions led the inventors to reason that such macrocycles would be ideal for use in techniques to separate and purify oligonucleotides, or as tools in the removal of phosphorylated environmental contaminants from ground water, soil, foodstuffs, and the like. They may therefore be employed to analyze and separate pesticides such as, but not limited to, carbofuran, carbendazim, bromacil, bentazon, carboxin and norflurazon. Cyclo[n]pyrrole-substituted silica gels and columns may be employed in the rapid detection and analysis of organophosphorus chemical warfare agents, allowing them to be disposed of where necessary.

A method of making a solid-supported cyclo[n]pyrrole macrocycle comprising attaching the macrocycle having a functionalized group to a solid support, the solid support reactive with the functionalized group, or to a tether-functionalized solid support, the tether reactive with the functionalized group is a further embodiment of this invention. An example of a solid support is an aminopropyl silica gel linked to a cyclo[n]pyrrole via a β-carbon. A cyclo[n]pyrrole modified solid support in the form of a chromatography column or capillary electrophoresis tube or a contacting process involving the macrocycle modified solid support in a batch process is an embodiment of this invention.

A method of forming a complex of a cyclo[n]pyrrole and an anion or a neutral molecule, comprising contacting the cyclo[n]pyrrole with the anion or neutral molecule under conditions effective to allow the formation of the complex is another embodiment of this invention.

Another embodiment of this invention is a method of transporting a molecular or ionic species through a membrane comprising incorporating a cyclo[n]pyrrole into the membrane; and contacting the membrane with the molecular or ionic species in the presence of a gradient of the molecular or ionic species, or a counter gradient of a further species wherein the molecular or ionic species is transported through the membrane by the cyclo[n]pyrrole. The further species may be a back-transported species. Thus, the present invention may be used to facilitate the transport of ionic or neutral substrates in both a synport or antiport sense. The transporting may result in the purification of the molecular or ionic species.

Removal of pertechnetate from pertechnetate-containing nuclear waste comprising contacting the waste with a cyclo[n]pyrrole to form a cyclo[n]pyrrole-pertechnetate complex; and removing the complex from the waste is an embodiment of this invention.

A method of removal of an environmental pollutant from an environmental source, comprising contacting the environmental source with a cyclo[n]pyrrole to form a cyclo[n]pyrrole-pollutant complex, and removing the complex from the environmental source is a further embodiment of this invention. Environmental pollutants such as, but not limited to nitrates, phosphates, sulfates, polychlorobiphenyls, and fluoride are damaging to the environment.

Cyclo[n]pyrroles as Sensors. Sensors that operate in organic or aqueous solution as soluble molecular entities are another embodiment of the present invention. The binding of anionic or neutral substrates or the complexation of cations will affect the optical properties of the cyclo[n]pyrroles allowing for the presence of the analyte in question, be it an anionic, neutral, or cationic entity, to be detected via absorption or emission spectroscopy or via so-called naked eye detectable changes in solution color. The cyclo[n]pyrrole used in such applications need not be monomeric and can display changes in optical properties as the result of changes in solubility or aggregation state. Cyclo[n]pyrroles being easy to make offer advantages over other expanded porphyrin and polypyrrole materials hitherto developed as sensors. The red shifted nature of their absorbances, allowing for detection by optical means with little or no interference from bodily tissues or endogenous pigments, including those found in blood, make the cyclo[n]pyrroles particularly attractive as sensors for use in biological mileus, including applications involving in vivo and in vitro analysis. A sensor comprising a solid support bound to a macrocycle of the present invention is a further embodiment of the present invention. A sensor made by either electropolymerizing the macrocycle onto the surface of the solid support or encapsulating the macrocycle into a membrane attached to the surface of the solid support is envisioned to act as an electrochemical sensor for ionic or molecular species.

In vivo applications. Water-soluble cyclo[n]pyrroles may be particularly advantageous for use in a number of ways, such as in cellular recognition, targeting, and in the transport of biologically important molecules. Generally, water-soluble cyclo[n]pyrroles are preferred for biomedical applications. "Water soluble" means soluble in aqueous fluids to about 1 mM or better.

Anionic phosphorylated entities are ubiquitous in biology. They play a critical role in a variety of fundamental processes ranging from gene replication to energy transduction. In addition, certain phosphate-bearing nucleotide analogues, such as, e.g., 9-(β-D-xylofuranosyl)guanine-5'-monophosphate (xylo-GMP), are known to display antiviral activity in vitro. However, xylo-GMP, like a considerable number of phosphorylated nucleotide analogues which exhibit anti-viral activity in cell-free extracts, is inactive in vivo due to its inability to cross lipophilic cell membranes.

The anti-herpetic agent, acyclovir (9-[(2-hydroxyethoxy)methyl]-9H-guanine), is active in vivo. Acyclovir can enter the cell only in its uncharged nucleoside-like form. Once in the cytoplasm, it is phosphorylated, first by a viral encoded enzyme, thymidine kinase, and then by relatively non-specific cellular enzymes to produce an active ionic triphosphate nucleotide-like species. There, it functions both as an inhibitor of the viral DNA polymerase and as a chain terminator for newly synthesized herpes simplex DNA.

The biological limitations of many other potential antiviral agents, including xylo-G, arise from the fact they are not phosphorylated once inside the cell and are therefore largely or completely inactive. If, however, the active monophosphorylated forms of these putative drugs could be transported into cells, it would be possible to fight viral infections with a large battery of otherwise inactive materials. If such specific into-cell transport were to be achieved, it would therefore greatly augment the treatment of such debilitating diseases as, for example, AIDS, herpes, hepatitis and measles. Given the fact that AIDS is currently a major world health problem of frightening proportions, and that something so nominally benign as measles still claims over 100,000 lives per year world-wide, treatment of these diseases would be particularly timely and worthwhile.

The present macrocycles provide a means of transporting active mono- and poly-phosphorylated forms of these and other agents into cells. This would allow a wide range of otherwise inactive compounds, such as antivirals, to be employed therapeutically, and would also create new possibilities for gene therapy.

Cyclo[n]pyrrole-based systems may be made effective as neutral regime carriers, say, e.g., for GMP by constructing a polytopic receptor system in which a nucleobase recognition unit, in this case, a cytosine-like group, is appended directly to a phosphate-chelating cyclo[n]pyrrole macrocycle. Nucleobase recognition units are demonstrated herein for use in the specific binding and transport of complementary nucleobases and nucleobase-containing compounds.

Cyclo[n]pyrrole conjugates and multitopic cyclo[n]pyrrole-based receptors are contemplated to address the following objectives: (i) the complexation of two very different kinds of substrates (charged anionic and neutral nucleobase); (ii) the specific recognition of multifunctional targets, such as nucleotides, whose targeting can be improved by attaching a second, ancillary recognition unit, such as a nucleic acid base, to an anion-binding cyclo[n]pyrrole core; and (iii) as precursors for the generation of oligomeric cyclo[n]pyrrole species bearing numerous combinations of multitopic receptors. The present inventors envisage expanding this theme to the preparation of oligomeric, multitopic receptors capable of recognizing multiple phosphate anions and nucleobase portions of nucleotide derivatives arranged in specific sequences. Ditopic receptor systems are ideal vehicles for the intracellular transport of oligonucleotides and their derivatives, including anti-viral agents. The multitopic receptors, likewise, are contemplated to be of use in binding to oligonucleotides and specific sections of DNA or RNA and in transporting such nucleic acid segments into cells. Contemplated ancillary recognition groups include, but are not limited to nucleic acid derivatives, crown ethers, aza- and thiacrown ethers, ammonium cations, guanidinium cations, bipyridine groups, phenanthroline groups, urea groups, amide groups, sulfamide groups, saccharides, and oligonucleotides.

Pharmaceutical preparations. For in vivo and ex vivo uses, cyclo[n]pyrroles are provided as pharmaceutical preparations. A pharmaceutical preparation of a cyclo[n]pyrrole may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a cyclo[n]pyrrole of the present invention and a pharmaceutically acceptable carrier are then easily administered in a variety of dosage forms. Administration may be intravenous, intraperitoneal, parenteral, intramuscular, subcutaneous, oral, or topical, with intravenous administration being preferred. A cyclo[n]pyrrole to be used in the medically-related methods of the invention will be administered in a pharmaceutically effective amount, employing a method of administration, pharmaceutical formulation, and, where indicated, with light, radiation, or a chemotherapeutic agent, for example, as is known in the art in light of the present disclosure. One of skill in the art in light of the present disclosure would also realize flexibility in the herein described regimens and would be able to test, without undue experimentation, for optimal timing and dosage for administration of a cyclo[n]pyrrole for a particular circumstance. A specific dose will vary depending on the particular cyclo[n]pyrrole chosen, the dosing regimen to be followed, and the particular co-therapeutic agent with which it is administered, employing dosages within the range of about 0.05 μmol/kg/treatment up to about 100 mg/kg/treatment.

Solutions of the cyclo[n]pyrroles in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Topical creams, emulsions, solutions, and the like are contemplated for applications to surface areas of the body. Topical application may also be by iontophoresis.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, permeation enhancers, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Cyclo[n]pyrroles may be incorporated into liposomes for use in the present invention. Liposomes may be prepared by any number of techniques that include freeze-thaw, sonication, chelate dialysis, homogenization, solvent infusion, microemulsification, spontaneous formation, solvent vaporization, reverse phase, French pressure cell technique, or controlled detergent dialysis, for example. Preparation may be carried out in a solution, such as a phosphate buffer solution, containing cyclo[n]pyrrole-lipophilic molecule conjugates so that the conjugate is incorporated into the liposome membrane. Alternatively, the conjugate may be added in already formed liposomes. Liposomes employed in the present invention may be of any one of a variety of sizes, preferably the less than about 100 nm in outside diameter, more preferably less than about 50 nm.

Micelles may be prepared by suspension of a cyclo[n]pyrrole-lipophilic molecule and lipid compound(s) in an organic solvent, evaporation of the solvent, resuspension in an aqueous medium, sonication and then centrifugation. Alternatively, the cyclo[n]pyrrole-lipophilic molecule may be added to preformed micelles. Techniques and lipids for preparing liposomes and micelles are discussed in U.S. Pat. No. 5,466,438, incorporated herein by reference.

Use of cyclo[n]pyrroles in ex vivo and in in vivo treatment of body tissues. Use of macrocycles of the present invention includes the dialysis of bodily fluids. Examples of dialyzable substrates include, but are not limited to, phosphate-containing molecules or halide waste. Examples of conditions for treatment include gout, diabetes, or drug overdoses.

Using kidney dialysis to illustrate an ex vivo treatment, bodily fluid would be contacted with a cyclo[n]pyrrole. Phosphate bound by the macroycle is removed from the blood.

Compositions comprising the macrocycles of the invention incorporated into a polymer matrix, incorporated into a membrane, or incorporated into a liposome are further aspects of the invention. A polymer is composed from the covalent assembly of small precursor subunits, generally referred to as monomers, and can be comprised of a large range of such monomeric subunits which need not be identical. Typical monomeric subunits include amines, acid chlorides, isocyanates, thiols, glycols, amino acids, nucleotides, and alkenes and typical bonding motifs found in polymers include amides, esters, ureas (urethane), carbamate, carbonate, carbon-carbon linkages, disulfides, and phosphodiesters. The term polymeric matrix is also well recognized in the art and is used to refer to both the structure of the polymer and its interior environment. Polymers are useful in the context of the present invention in that they may be used both as supports to which cyclo[n]pyrroles may be attached (i.e., solid supported cyclo[n]pyrroles) or as environments into which cyclo[n]pyrroles may be contained (matrix incorporated cyclo[n]pyrroles), through either physical mixing or chemical reaction (i.e., direct covalent incorporation).

Membranes are hydrophobic phases that can serve, for example, to seal off, separate, or enclose an aqueous environment from one or more other aqueous environments. Membranes are widely dispersed in the biological world and a diverse range of hydrophobic materials may be used to construct artificial membranes, including biomimetic entities such as phosphatidyl choline or cholesterol, complex organic materials such as diaryl ethers, or simple organic solvents such as dichloromethane. Artificial membranes may be free standing, supported on polymers of either synthetic or biological origin, or formed as lipid bilayers on surfaces, across pores, or as liposomes in aqueous media. They may also consist of bulk hydrophobic phases. Membranes and closely related species, micelles wherein hydrophobic microenvironments are generated with an aqueous medium, may also be formed from surfactants. Cyclo[n]pyrroles contained in or otherwise associated with membranes, micelles, and bulk organic phases constitute an embodiment of this invention.

Anions that may be bound, removed, or sensed by cyclo[n]pyrroles of the present invention include, but are not limited to, fluoride, chloride, phosphate, pertechnetate, glyphosate, nitrate, nitrite, arsenate, arsenite, cyanide, ferricyanide, ferrocyanide, cyano coordination compounds with gold or silver, for example, perchlorate, permanganate, perrhenate, perruthenate, iodate, periodate, bromate, selenate, selenite, alkyl or aryl phosphate, nucleotide mono-, di- or tri-phosphate, inositol phosphate, biological phosphates such as glucose 1- or 6-phosphate, acetate, alkylcarboxy, arylcarboxy, zwitterion, hydroxy acid anion, pyrophosphate, sulfate, alkyl sulfate, aryl sulfate, thiosulfate, sulfide, alkyl sulfide, aryl sulfide, sulfite, phosphonate, alkyl phosphonate, aryl phosphonate, enolate, alkoxide, thiolate, phenolate, sulfonate, alkyl sulfonate, aryl sulfonate, or the like.

An advantage of the cyclo[n]pyrroles is that they are stable due to the absence of meso carbons. This abets their use in applications as set forth herein. Under acidic conditions and extreme high temperatures, a meso linkage may degrade. Pyrrolic macrocycles containing meso carbons are also susceptible to oxidative degradation both in the dark and, particularly, in the presence of light.

An advantage of the present invention is that the substitution pattern of the cyclo[n]pyrroles may be readily modified by one of skill in the art using the methods detailed in this disclosure. This allows the hydrophobicity and hydrophilicity of the cyclo[n]pyrroles to be optimized for a given application. For instance, in extraction applications, where retaining the cyclo[n]pyrrole in an organic phase or membrane environment is necessary, a hydrophobic cyclo[n]pyrrole with a log P (partition ratio) of >2, preferably >4, would be selected.

Cyclo[n]pyrroles are useful in co-extraction methods. For example, a method for extracting an ion pair from an environment containing the ion pair where the environment is contacted with at least two coextractants, wherein the coextractants are at least a cyclo[n]pyrrole and a cation extractant is an aspect of the present invention. The cyclo[n]pyrrole binds the anion and the cation extractant binds the cation thereby allowing for removal of the ion pair from the environment. In particular, use of cyclo[n]pyrroles to facilitate uptake of a cation into an organic phase from an aqueous phase is contemplated by the present inventors. Co-extraction may also be carried out with a cation exchanger rather than a cation extractant. Where a cation exchanger is employed, the cation to be removed is replaced with the cation of the cation exchanger.

The cation extractant in co-extraction may be a crown ether, a crown ether containing one or more heteroatoms, a cryptand, a cycloarene, a cyclodextrin, polyethyleneglycol, or an ion exchange resin, for example. The cation extractant may be a cation exchanger, i.e, a highly lipophilic cation, such as an ammonium cation or substituted ammonium cation, pyridinium, guanidinium, specifically added for the purpose of replacing the original cation present in the ion pair. It can also be a neutral species such as a polyethylene glycol, polyether, crown ether, cycloarene, cyclodextrin, dendrimer, or cyclophane, or combinations thereof The cation of the inital ion pair or that formed by exchange may be monovalent or divalent. Specific cations include, but are not limited to, Group 1 metals, Group 2 metals, transition metals, post-transition metals, lanthanides, actinides such as americium, ammonium, alkylammonium, arylammonium, hydroxonium and guanidinium. In particular, coextraction of cesium, americium, or sodium is contemplated. The anion of the ion pair may include, but is not limited to, a halide anion particularly fluoride, chloride, bromide, or iodide, the anionic portion of an amino acid zwitterion, formate, acetate, carboxylate, phosphate, alkyl phosphates, aryl phosphates, pyrophosphates, organic phosphates, creatinine phosphate, organic phosphonates, nitrate, nitrite, arsenate, cyanide, glyphosate, sulfate, oxalate, terephthalate, phospholipid, nucleotide, nucleotide analogue, oligonucleotide, ATP, DNA, RNA, anionic polyoxometalate, or oxoanion such as pertechnetate, perchlorate, tungstenate, or borate, for example.

For coextraction methods of the invention, "associated with" means that the cation and anion are bound to each other strongly or weakly via electrostatic interactions, hydrophobic, van de Waals, or other non-covalent forces as well as species that are covalently linked to one another, such as in zwitterions. A contact ion pair, a solvent separated ion pair, and a zwitterion, for example, are considered as "an ion pair having a cation associated with an anion." In certain embodiments, the ion pair is an environmental pollutant or an amino acid zwitterion. The cation coextractant is a crown ether, a crown ether containing one or more heteroatoms, cyclodextrin, calixarene, cyclophane, ammonium cation, substituted ammonium cation, guanidinium, polyethylene glycol, polypropyleneglycol, polyammonium or polyalkylammonium such as protonated or alkylated spermine or spermidine, a cryptand, bicyclic or polycyclic ammonium, or a dendrimer, for example, in one embodiment of the invention, and in another, the cation coextractant is a cation exchanger. Mixtures of cation coextractants, mixtures of cation exchangers, or mixtures of a cation coextractant and a cation exchanger are contemplated as cation coextractants. Preferably, the cation coextractant is a crown ether, a cryptand, a calixarene, a calixarene-crown ether cryptand, or a calixarene-crown ether conjugate. Further, a covalent conjugate formed by the reaction of one or more cation coextractants are also considered as a cation coextractant for the present invention. A dendrimer is a star-like or tree-like polymer that radiates from a central core such as described in U.S. Pat. No. 4,507,466, U.S. Pat. No. 5,041,516 U.S. Pat. No. 6,255,424, or U.S. Pat. No. 5,714,166, incorporated by reference herein.

Cyclo[n]pyrroles are further useful for reducing or preventing corrosion of a substrate susceptible to corrosion in the presence of chloride, nitrate, fluoride, cyanide, sulfate or other corrosion-promoting anions. The method comprises contacting the substrate with a cyclo[n]pyrrole wherein the cyclo[n]pyrrole binds the corrosion-promoting anion thereby reducing or preventing corrosion of the substrate. The substrate is any material susceptible to corrosion such as metal-containing materials. The substrate could also be filters, gaskets, o-rings, valves or other components derived from rubber, plastic, glass or other industrial materials that undergo corrosion, etching, or other forms of degradation in the presence of anions. This protection from corrosion may be effected directly by, for instance, coating the material in question with a cyclo[n]pyrrole. Or, it may be done by removing the anion in question from a solution, solvent, mixture, or bulk chemical entity in which the component or material being protected comes into contact. Cyclo[n]pyrrole-based removal strategies could prove particularly advantageous when applied to the removal of chloride anion from organic solvents and commodity chemicals, such as gasoline or jet fuels, since these products contain chloride anion, which is implicated in corrosion.

Cyclo[n]pyrroles are further useful for producing a naked cation or "bare" cation in a solution containing the cation paired with an anion. The method comprises contacting a cyclo[n]pyrrole with the solution, wherein the cyclo[n]pyrrole binds the anion thereby providing the naked cation. Such a "bare" or naked cation may be useful for catalytic activity promoted by the paired cation. Examples of catalytic activity include the promotion of polymer formation, hydrogenation, olefin metathesis, metal-based coupling reactions, oxidations, reductions, and other metal-promoted transformations.

A method of removal of an environmental pollutant from an environmental source is also a use for cyclo[n]pyrroles. The method comprises contacting the environmental source with a cyclo[n]pyrrole to form a cyclo[n]pyrrole-pollutant complex, and removing the complex from the environmental source. In particular, removal of radioactive pertechnetate, nitrate, nitrite, arsenate, or phosphorylated environmental contaminants from storage tanks, holding pits associated with agricultural and mining operations, ground water, soil, foodstuffs, and the like, is contemplated. Organophosphorus chemical warfare agents, such as sarin, may be removed from the environment using cyclo[n]pyrroles.

Further, anion concentrations may be controlled using cyclo[n]pyrroles. For example, controlling fluoride concentration is useful in deprotecting silyl protecting groups used in making synthetic RNA fragments, where the Lewis basicity of fluoride anion promotes unwanted backbone hydrolysis.

Cyclo[n]pyrroles may further be used in desalination methods.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cyclo[n]pyrroles, Quaterpyrroles, Sexipyrroles and Synthesis thereof

The present example provides cyclo[n]pyrrole macrocycles where n is 6–12. In particular, cyclo[8]pyrrole macrocycles 2a, 2b, 2c, 2d (Scheme 1) and cyclo[12]pyrrole macrocycles are provided herein using a highly efficient one-step synthesis that involved the direct coupling of bipyrrolic fragments. A change of the acid in the cyclization procedure yields cyclo[6] and cyclo[7]pyrrole.

Procedure for the oxidative coupling of bipyrroles. All solvents and chemicals were obtained commercially and used as received. Bipyrrolic precursors were prepared as described previously (E. Vogel et al., *Angew. Chem.* 1993, 105, 1670 and in *Angew. Chem. Int. Ed. Engl.* 1993, 32, 1600; J. L. Sessler, and M. C. Hoehner, *Synlett* 1994, 211; M. R. Johnson, et al., *J. Porphyrins Phthalocyanines* 1997, 1, 87; and U.S. Pat. No. 5,756,724, May 26, 1998 and U.S. Pat. No. 5,179,120, Jan. 12, 1993, each patent is incorporated by reference herein in its entirety).

A 1 L round bottom flask was charged with a stir bar, 500 mL of dichloromethane, and a solution of 2.7 g of FeCl$_3$·6H$_2$O (10 mmol) in 100 mL of 1 M sulfuric acid. The resulting biphasic mixture was stirred at 300 RPM, while the bipyrrole 3a, 3b, 3c, or 3d (Scheme 1, 1 mmol), dissolved in 50 mL of dichloromethane, was added slowly via syringe pump over a period of 9 hours, with the needle submerged into the organic phase. For slow continuous additions, a Sage syringe pump (model M365) was employed. After completion of the addition, the reaction mixture was stirred for 5 more hours. Subsequently, the phases were separated and the organic phase was dried over anhydrous sodium sulfate. Following filtration, the solvent was removed in vacuo to yield the crude product. The crude products were purified via column chromatography on silica gel using dichloromethane containing methanol (2–5%) as the eluent. The yellow band was collected and the solvent removed in vacuo. The solid residue was recrystallized from dichloromethane/methanol to yield 2a–d as dark microcrystalline powders.

To obtain a mixture of cyclo[6], [7] and [8]pyrrole the same coupling procedure as described above was performed with the exception that 1M sulfuric acid was exchanged by 1M hydrochloric acid, and the bipyrrole was added to the biphasic reaction mixture over a period of 14 hours instead of 9 hours. The phases were not dried over sodium sulfate but the solvent immediately removed in vacuo. The crude dark green product was purified via column chromatography on silica gel using dichloromethane containing 0.5% methanol as the eluent to yield a hazelnut brown band of cyclo[6]pyrrole. Increasing the polarity of the solvent system to 2% methanol yielded a yellow brown band of cyclo[8] pyrrole. Further increasing the polarity to 7.5% methanol in dicbloromethane afforded a grass green band consisting of cyclo[7]pyrrole. The solvent was removed in vacuo, the residues recrystallized from dichloromethane/hexanes to yield the corresponding bis chloride salts of the cyclo[6,7,8]pyrroles as dark microcrystalline powders.

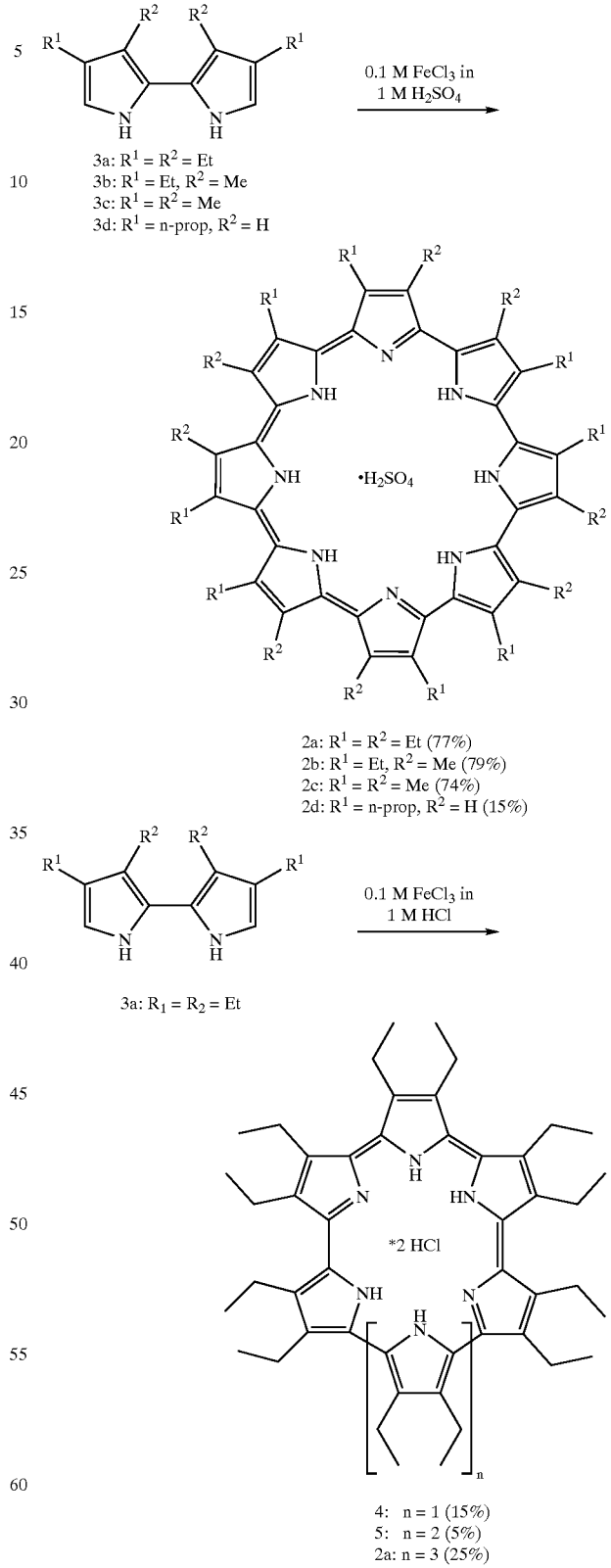

Proton and $^{13}$C-NMR spectra were measured at 25° C. on a Varian Unity Plus spectrometer at 300 MHz, or on a Varian Unity Innova at 500 MHz. UV-vis spectra were recorded at the present inventors' instruction at Wright Patterson Air Force Base using a modified Carey 500 spectrophotometer, and in the case of the cyclo[6]- and cyclo[7]pyrroles, on a BECKMAN DU 640B spectrophotometer. High resolution CI mass spectra were obtained on a VG ZAB2-E mass spectrometer.

2,3,6,7,10,11,14,15,18,19,22,23,26,27,30,31-Hexadecaethyl[30]octaphyrin(0.0.0.0.0.0.0.0) (2a) 77% yield; $^1$H-NMR (500 MHz, CDCl$_3$) δ [ppm] 0.64 (s, 8H, NH), 1.63 (t, $J_{HH}$=7.5 Hz, 48H, CH$_2$CH$_3$), 4.17 (bs, 32H, CH$_2$CH$_3$); $^{13}$C-NMR (125 MHz, CDCl$_3$) δ [ppm] 16.13, 21.92, 126.26, 128.43; HRMS (CI): m/z 1065.6710 (MH$^+$), calcd for C$_{64}$H$_{89}$N$_8$O$_4$S$_1$ 1065.6727.

2,7,10,15,18,23,26,31-Octaethyl-3,6,11,14,19,22,27,30-octamethyl-[30]octaphyrin-(0.0.0.0.0.0.0.0) (2b) 79% yield; $^1$H-NMR (300 MHz, CDCl$_3$) δ [ppm] –0.64 (s, 8H, NH), 2.07 (t, $J_{HH}$=7.5 Hz, 24H, CH$_2$CH$_3$), 3.76 (s, 24H, CH$_3$), 4.17 (q, $J_{HH}$=7.5 Hz, 16H, CH$_2$CH$_3$); $^{13}$C-NMR (75 MHz, CDCl$_3$) δ [ppm] 15.90, 15.99, 22.17, 123.87, 125.34, 126.44, 129.27; HRMS (CI): m/z 952.5399 (M$^+$), calcd for C$_{56}$H$_{72}$N$_8$O$_4$S$_1$ 952.5397; UV-vis (CH$_2$Cl$_2$) λ$_{max}$ [nm] (ε in mol$^{-1}$·L$^{-1}$) 431 (79800), 1112 (132200).

2,3,6,7,10,11,14,15,18,19,22,23,26,27,30,31-Hexadecamethyl[30]octaphyrin(0.0.0.0.0.0.0.0) (2c) 74% yield. $^1$H-NMR (300 MHz, CDCl$_3$) δ [ppm] –0.84 (s, 8H, NH), 3.58 (s, 48H, CH$_3$); $^{13}$C-NMR (75 MHz, CDCl$_3$) δ [ppm] 15.63, 123.89, 125.87; HRMS (CI): m/z 841.4214 (MH$^+$), calcd for C$_{48}$H$_{57}$N$_8$O$_4$S$_1$ 841.4224.

2,7,10,15,18,23,26,31-Octapropyl-[30]octaphyrin (0.0.0.0.0.0.0.0) (2d) 15% yield; $^1$H-NMR (300 MHz, CDCl$_3$) δ [ppm] –1.63 (s, 8H, NH), 1.31 (t, $J_{HH}$=7.3 Hz, 24H, CH$_2$CH$_2$H$_3$), 2.50–2.63 (m, 16H, CH$_2$CH$_2$CH$_3$), 4.78 (t, $J_{HH}$=7.9 Hz, 16H, CH$_2$CH$_2$CH$_3$), 9.89 (d, $J_{HH}$=2 Hz, 8H); $^{13}$C-NMR (75 MHz, CDCl$_3$) δ [ppm] 14.74, 25.42, 33.34, 114.53, 124.80, 128.10, 133.48; HRMS (CI): m/z 953.5461 (MH$^+$), calcd for C$_{56}$H$_{73}$N$_8$O$_4$S$_1$ 953.5476.

2,3,6,7,10,11,14,15,18,19,22,23-Dodecaethyl[26] hexaphyrin(0.0.0.0.0.0) (4) 15% yield; $^1$H-NMR (500 MHz, CDCl$_3$) δ [ppm] –1.46 (s, 6H, NH), 1.81 (t, $J_{HH}$=7.5 Hz, 36H, CH$_2$CH$_3$), 4.12 (q, $J_{HH}$=7.5 Hz, 24H, CH$_2$CH$_3$); $^{13}$C-NMR (125 MHz, CDCl$_3$) δ [ppm] 19.12, 22.98, 127.94, 135.69; HRMS (CI): m/z 726.5351 (MH$^+$), calcd for C$_{48}$H$_{66}$N$_6$ 726.5349. UV-vis (CH$_2$Cl$_2$) λ$_{max}$ [nm] (ε in mol$^{-1}$·L$^{-1}$) 397 (265800), 708, 792 (427500)

2,3,6,7,10,11,14,15,18,19,22,23,26,27-Tetradecaethyl [28]heptaphyrin(0.0.0.0.0.0.0) (5) 5% yield; $^1$H-NMR (500 MHz, CDCl$_3$) δ [ppm] –2.12 (s, 8H, NH), 1.80 (t, $J_{HH}$=7.5 Hz, 42H, CH$_2$CH$_3$), 4.26 (q, $J_{HH}$=7.5 Hz, 28H, CH$_2$CH$_3$); $^{13}$C-NMR (125 MHz, CDCl$_3$) δ [ppm] 16.78, 21.63, 126.17, 131.37; HRMS (CI): m/z 883.6003 (MCl$^+$), calcd for C$_{64}$H$_{89}$N$_8$O$_4$S$_1$ 883.6007. UV-vis (CH$_2$Cl$_2$) λ$_{max}$ [nm] (ε in mol$^{-1}$·L$^{-1}$) 429 (181400), 943 (279700).

While the FeCl$_3$-induced oxidative coupling of bipyrroles produced cyclo[8]pyrroles under a range of conditions, the best yields were obtained under carefully optimized biphasic conditions (bipyrrole in CH$_2$Cl$_2$; FeCl$_3$ in 1 M H$_2$SO$_4$). In this optimized procedure, the rate of addition is carefully controlled so as to ensure a very low concentration of bipyrrole in the organic phase at all times. Also, the stirring speed is kept low, so as to minimize the extent to which the two phases are allowed to mix.

Using these conditions, the yields of cyclo[8]pyrroles, isolated in the form of their dihydrogen sulfate salts, are remarkably good since the yields are above 70% in the case of 2a–c as indicated in Scheme 1. Such yields are noteworthy in the area of expanded porphyrin chemistry and rival the best yields seen in the synthesis of β-substituted octaalkylporphyrins. On the other hand, the yields observed for 2d are significantly lower (15%). While a variety of factors could account for this finding, the present inventors believe that the lack of full β-substitution allowed for competing β–β' or β–α-coupling reactions. The yield for cyclo[8] pyrrole formation decreases at higher stirring speeds or faster addition rates in the above cited synthesis method.

In a homogeneous synthesis procedure that involves the use of a single phase, the coupling was performed in ethanol. Interestingly, slow addition of bipyrrole to a solution of FeCl$_3$ in acidified ethanol gave rise to cyclo[8]pyrroles in yields very similar to when FeCl$_3$ in acidified ethanol was added slowly to a solution of bipyrrole in ethanol.

The NMR-spectra of the cyclo[8]pyrrole dihydrogen sulfate salts 2a–d are characterized by their unusually high symmetry. Based on the positions of the signals observed in the respective $^1$H-NMR spectra, 2a–d are judged to be aromatic. Specifically, for the spectrum of 2a recorded in CDCl$_3$ at room temperature, the signal corresponding to the NH protons resonates at 0.64 ppm, clearly upfield from "normal" pyrrolic NH protons. The only two remaining signals, a triplet at 1.63 ppm and an unresolved quartet at 4.17 ppm, are assigned to the single chemically distinct (i.e., magnetically degenerate) ethyl group. While unresolved at room temperature, the quartet at 4.17 ppm corresponding to the CH$_2$CH$_3$ protons displays a chemical shift that is typical for a methylene group attached directly to the periphery of an aromatic expanded porphyrin-type macrocycle (J. L. Sessler et al., *Angew. Chem* 2001, 113, 611; *Angew. Chem., Int. Ed.* 2001, 40, 591). At low temperature (223 K, CDCl$_3$), the CH$_2$CH$_3$ signal is nearly resolved as a distinct quartet, while the NH resonance shifts to –0.2 ppm.

The $^1$H-NMR spectra of cyclo[8]pyrroles 2b–d are similar to that of 2a. However, in addition to the expected differences in the alkyl region, including the observation of a β-CH signal at 9.9 ppm in the case of 2d, a noticeable trend in the position of the NH resonances is observed. Specifically, at room temperature in CDCl$_3$, the NH signal for 2b is seen to resonate at –0.64 ppm, while the corresponding signals for 2c and 2d are observed at –0.84 and –1.63 ppm, respectively. These differences are interpreted in terms of the latter, less sterically hindered systems being better able to adopt conformations that lie closer to true planarity.

Also underscoring the high symmetry of 2a–d, and hence their inferred near-planarity, are their respective $^{13}$C-NMR spectra. Here, the prototypic spectrum is that of 2c, which displays only three distinct signals. Such a limited number of signals is quite unusual for a molecule with 48 carbon atoms and a molecular weight of 841. Excluding perturbations due to the sulfate counteranion, this leaves 2c with an effective $D_{8h}$ symmetry in solution.

Figure 7:
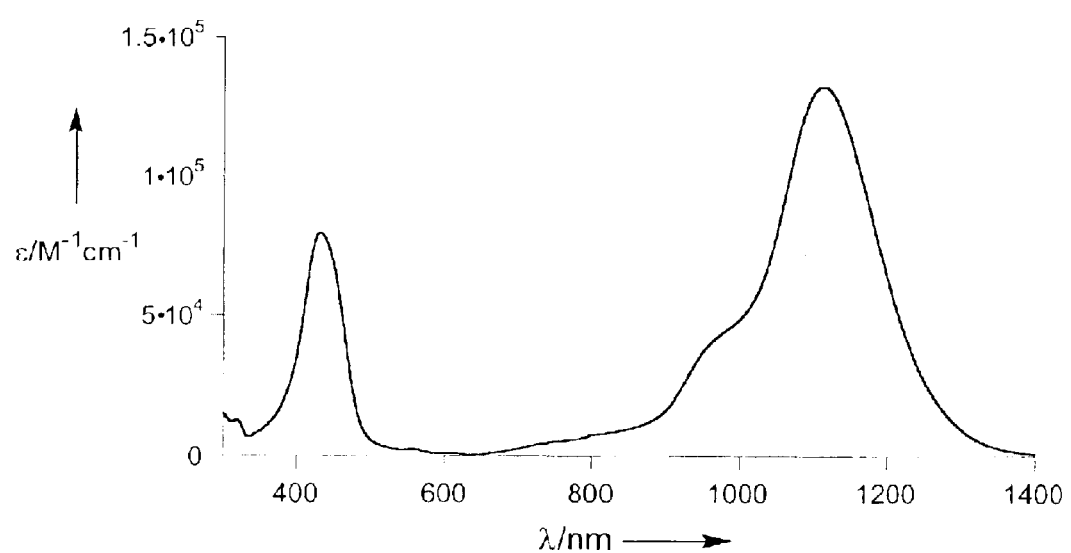
FIG. 7 illustrates the UV-vis spectrum of 2b recorded in dichloromethane. The absorption maxima ($\epsilon$ in mol$^{-1}\bullet$L$^{-1}$) are at 431 (79800) and 1112 (132200) nm for the Soret and Q-like bands, respectively.

Consistent with the proposal that cyclo[8]pyrroles 2 are flat or nearly flat were the results of a single crystal X-ray diffraction analysis of 2b (FIG. 7). Crystallographic summary for 2b: Dark plates were grown by vapor diffusion of CH$_2$Cl$_2$ and methanol, triclinic, P-1 (No. 2), Z=2 in a cell of dimensions: a=11.4267(1), b=21.9142(2), c=24.5622(3) Å, α=76330(1), β=76.946(1), γ=81.367(1)°, V=5791.40(10) Å$^3$, ρ$_{calc}$=1.28 g-cm$^{-3}$, F(000)=2396, μ=0.207 mm$^{-1}$. A total of 40398 reflections were measured, 25843 unique (R$_{int}$= 0.045), on a Nonius Kappa CCD using graphite monochromatized Mo Kα radiation (λ=0.71073 Å) at –120° C. The structure was refined on F$^2$ to an R$_W$=0.184, with a conventional R=0.0957 (13724 reflections with F$_O$>4[σ(F$_O$)]), and a goodness of fit=2.13 for 1311 refined parameters.

There are two crystallographically independent macrocycle sulfate complexes. The presence of these two sulfate complexes establishes that cyclo[8]pyrroles can bind anions, particularly in the solid state. The observation of two crystallographically distinct complexes implies the existence of multiple binding modes which is a hallmark of a versatile receptor.

The bis TFA salt of Cyclo[6]pyrrole 4 (FIG. 1) crystals grew as very dark plates and prisms by vapor diffusion of hexanes into a methylene chloride solution of the macrocycle in the presence of trifluoroacetic acid in a triclinic crystal system, P-1, Z=1 in a cell of dimensions: a=10.9346 (4), b=11.0747(4), c=11.5478(4) Å, α=64.377(2), β=74.543 (2), γ=89.209(2)°, V=1206.97(7) Å$^3$, ρ$_{calc}$=1.31 g-cm$^{-3}$, F(000)=506, μ=0.099 mm$^{-1}$. A total of 9461 reflections were measured, 5381 unique (R$_{int}$=0.0264), on a Nonius Kappa CCD using graphite monochromatized Mo Kα radiation (λ=0.71073 Å) at −120° C. The structure was refined on w=1/[((σ(F$_O$))$^2$+(0.0437*P)$^2$+(0.5418*P)] and P=(|F$_O$|$^2$+ 2|F$_c$|$^2$)/3 0.121, to an R$_w$=0.1210 with a conventional R=0.0506 (5381 reflections with F$_O$>4[σ(F$_O$)]), and a goodness of fit=1.004 for 320 refined parameters.

The structure depicts two TFA molecules above and under the ring plane, the NH···O distances (six hydrogen bonding interactions) range from 2.05 to 2.78 Å. The macrocycle is as flat as the larger system, cyclo[8]pyrrole 2b.

Figure 3:
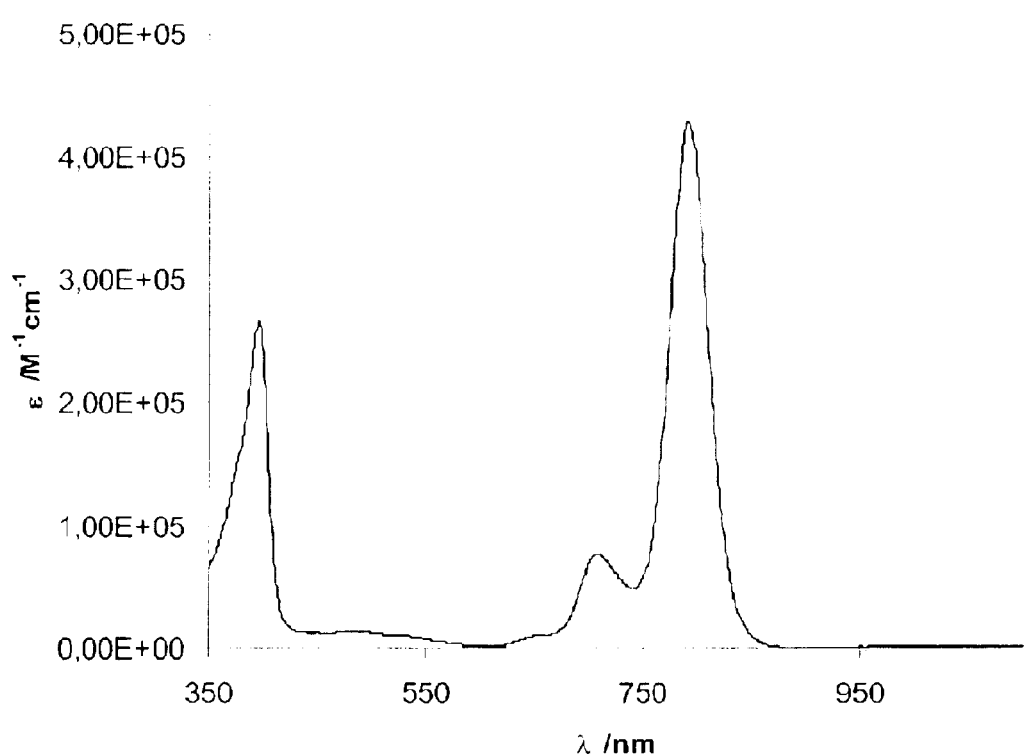
FIG. 3 illustrates the UV-vis spectrum of the bis hydrochloride salt of cyclo[6]pyrrole recorded in dichloromethane.
Figure 4:
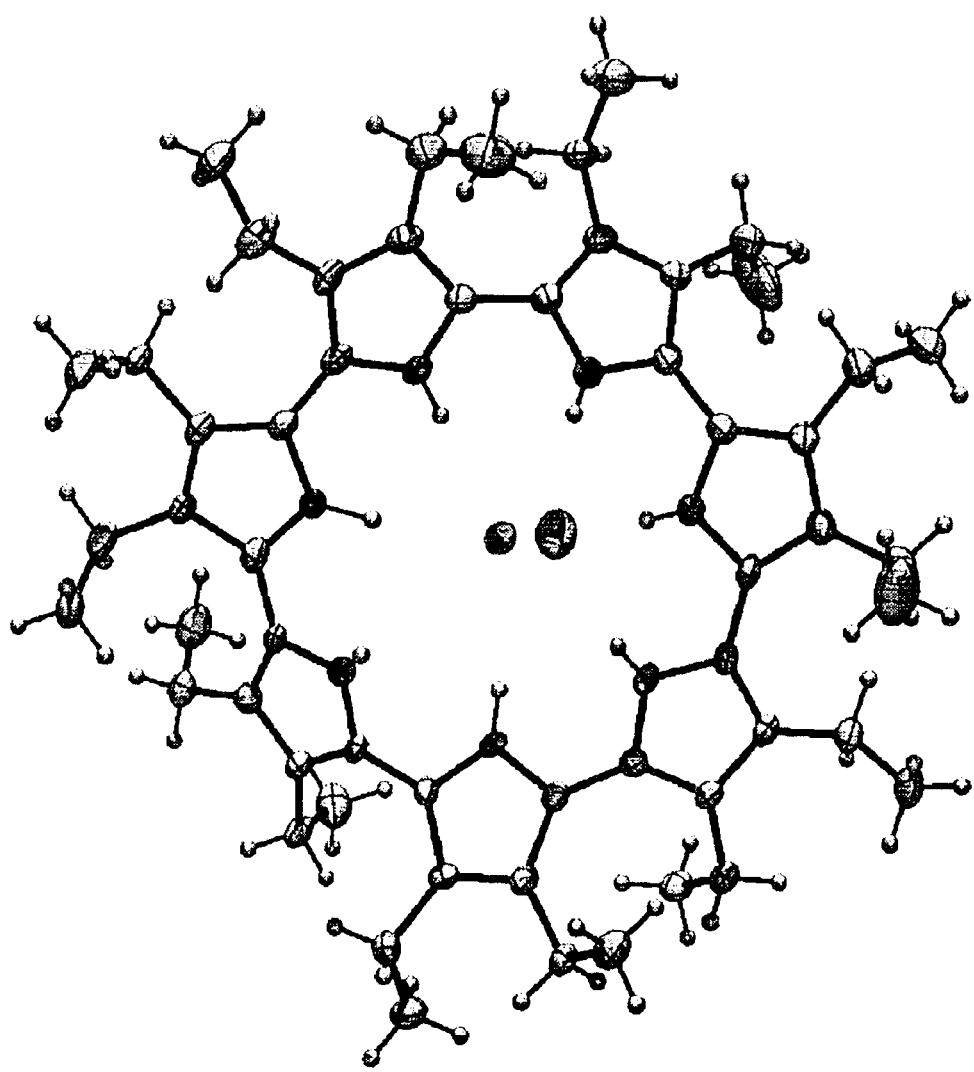
FIG. 4 illustrates an ORTEP-POV-Ray rendered view of the bis hydrochloride salt of cyclo[7]pyrrole. The thermal ellipsoids are scaled to the 50% probability level. NH $\cdots$ Cl bonding interactions range from 2.31 to 3.19 Å.

Consistent with the proposal that cyclo[7]pyrroles 5 are flat or nearly flat were the results of a single crystal X-ray diffraction analysis of 5 (FIG. 3). Crystallographic summary for 5: Crystals grew as dark green needles by vapor diffusion of hexanes into a benzene solution of the macrocycle, triclinic, P-1 (No. 2), Z=2 in a cell of dimensions: a=10.7430 (4), b=11.5435(5), c=26.1232(1) Å, α=99.666(2), β=98.104 (2), γ=104.904(2)°, V=3027.9(2) Å$^3$, ρ$_{calc}$=1.20 g-cm$^{-3}$, F(000)=1180, μ=0.156 mm$^{-1}$. A total of 16734 reflections were measured, 10386 unique (R$_{int}$=0.0871), on a Nonius Kappa CCD using graphite monochromatized Mo Kα radiation (λ=0.71073 Å) at −120° C. The structure was refined on F$^2$ to an R$_w$=0.1499, with a conventional R=0.0787 (10386 reflections with F$_O$>4[σ (F$_O$)]), and a goodness of fit=1.004 for 732 refined parameters. The structure contains two well behaved molecules of benzene and a water molecule on which the hydrogen atoms were idealized to 0.80 Å by sliding the H atom along the O—H bond vector.

The results of the X-ray diffraction analysis of 5 are consistent with the proposal that cyclo[7]pyrrole is nearly flat like cyclo[8]pyrrole. The structure reveals a macrocyclic system with two chloride anions above and beyond the plane. Seven hydrogen bonding interactions are inferred in the solid state from the NH···Cl distances which range from 2.30 and 3.19 Å.

Synthesis of Unsubstituted Cyclo[8]pyrrole. Unsubstituted bipyrrole does not give rise to isolable quantities of unsubstituted cyclo[8]pyrrole 2 when subjected to FeCl$_3$-based oxidation under the conditions described supra.

It is possible that formation of quaterpyrrolic or other intermediates lack sufficient solubility to carry on the reaction. However, in light of the present disclosure, one of ordinary skill in the art would appreciate that isolating these quaterpyrrolic fragments and subjecting them to oxidative coupling under conditions of high dilution using either of the two-phase or homogeneous synthesis procedures presented supra would provide for the synthesis of 2.

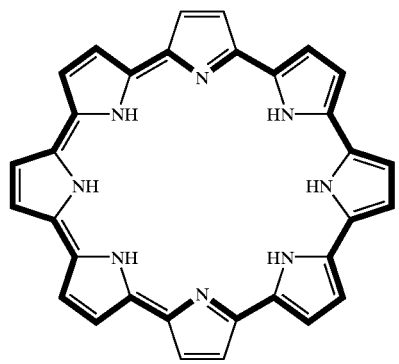

2

Compound 2 can also be prepared from a substituted cyclo[8]pyrrole by subjecting it to reactions procedures that would remove all beta-pyrrolic substituents. Cyclo[8] pyrroles bearing a range of substituents may be prepared using the methods disclosed in this application and most of these can be removed by the judicious choice of degradation reactions. In particular, carboxylic acids or halo substituents are readily removed. For example, 2,7,10,15,18,23,26,31-octacarboxy-[30]octaphyrin(0.0.0.0.0.0.0.0), prepared as described infra, will undergo decarboxylation, thereby generating 2, when subject to heating in the absence of air. Likewise, subjecting 2,3,6,7,10,11,14,15,18,19,22,23,26,27, 30,31-hexadecabromo[30]octaphyrin(0.0.0.0.0.0.0.0), prepared as described infra, to metal halogen exchange followed by aqueous work up, will yield 2, as would a range of other halogenated cyclo[8]pyrroles.

Synthesis of Cyclo[12]pyrrole. The yield of a blue product increases with faster addition rates of the bipyrrole and with faster stirring speeds in the above cited synthesis method. This blue product is considered to be a cyclo[12] pyrrole on the basis of a MALDI mass spectrometric analysis. This product precipitates shortly after elution from the column and is poorly soluble in common organic solvents. In light of this disclosure, one of skill in the art would appreciate that the use of bipyrrolic precursors that are very soluble in organic solvents will allow these species to be isolated in greater yields. Such highly soluble bipyrroles may be generated using the methods detailed in, for example, E. Vogel et al. (*Angew. Chem.* 1993, 105, 1670 and in *Angew. Chem. Int. Ed. Engl.* 1993, 32, 1600), J. L. Sessler and M. C. Hoehner (*Synlett* 1994, 211), M. R. Johnson, et al. (*J. Porphyrins Phthalocyanines* 1997, 1, 87), Barton, D. H. R. et al. (*Tetrahedron* 1990, 46, 7587–7598), and in U.S. Pat. No. 5,756,724, May 26, 1998 and U.S. Pat. No. 5,179,120, Jan. 12, 1993, previously incorporated by reference herein, while starting with pyrroles bearing long alkyl, ether, polyether, ester, or other solubilizing groups in one or both of the beta pyrrolic positions.

Isolation in the form of salts of acids derived from very soluble anions provides another way of improving the solubility of cyclo[12]pyrroles and increasing yields. Preferred solubilizing anions include, but are not limited to, tetraphenylborate, hexafluorophosphate, tetrafluoroborate, triflate (OSO$_2$CF$_3^-$), tetrakis(3,5-bis(trifluoromethyl) phenyl)borate (BArF$_4^-$), or perfluorotetraphenylborate (F$_{20}$BPh$_4^-$), and monocarborane CB$_{11}$H$_{12}^-$ cages.

Synthesis of Cyclo[n]pyrrole where n is 7, 9, 10, or 11. The present inventors, while not wanting to be bound by theory, expect that synthesis occurs from linear oligopyrrolic fragments, such as a linear octapyrrolic unit, two quaterpyrrolic units, four bipyrrolic units, or ultimately eight pyrrolic units for forming a cyclo[8]pyrrole. Similarly, three terpyrrolic units may be used under similar reaction conditions to form a cyclo[9]pyrrole. Two or three bipyrrolic units and a terpyrrollic unit would form a cyclo[7]pyrrole or cyclo[9] pyrrole whereas two terpyrrolic units could be used to generate a cyclo[6]pyrrole, respectively. A cyclo[10 or 11]pyrrole may be synthesized from a number of combinations of bipyrroles and terpyrroles.

Synthesis of Beta-Substituted Quaterpyrroles. The poor solubility of quaterpyrrolic fragments generated from bipyrrolic precursors bearing few or no substitutents in their beta pyrrolic positions, would allow for their isolation under the oxidative coupling conditions of the present example. One of skill in the art seeking to obtain such quaterpyrrolic fragments would appreciate that short reaction times would be used and the use of poorly solubilizing solvents beneficial.

Mono-alpha unsubstituted bipyrroles provide an alternative source of quaterpyrroles. These species described in Meyer, S. et al. (*J. Porphyrins Phthalocyanines* 1999, 3, 148–158) provide alpha-alpha' substituted quaterpyrroles when subject to the oxidative coupling procedures detailed in this example. Judicious choice of alpha and alpha' substituents would allow for the subsequent production of alpha-alpha' unsubstituted quaterpyrroles identical to those obtained by the direct isolation procedure described immediately above. In the case where the alpha or alpha' substituents are carboxylic acid esters such as in Scheme 2, the chemistry used to effect the transformation into the alpha-alpha' unsubstituted derivatives is known and would involve saponification followed by thermal decarboxylation.

5-Ethoxycarbonyl-3,3',4,4'-tetraethyl-2,2'-bipyrrole (6). A 500 mL round bottom flask was charged with bipyrroledi-ester (5 g, 12.9 mmol), 200 mL of ethanol and a solution of NaOH (568 mg, 14.2 mmol) in 40 mL of water. The resulting mixture was heated at reflux for 12 hours. The solvents were then removed under reduced pressure and the resulting solid residue dried before being dissolved in a minimal amount of TFA (ca. 25 mL). The resulting solution was stirred for 30 minutes, prior to addition of dichloromethane (100 mL) and water (100 mL). The resulting phases were separated and the aqueous phase extracted further with dichloromethane (2×100 mL). The combined organic phases were washed with 1M NaOH (2×100 mL) prior to being dried over anhydrous sodium sulfate. Solvent removal and chromatography on silica gel using $CH_2Cl_2$/hexanes (1:1) as eluent yielded the desired product 6 in 70.4% yield. For 6: $^1$H-NMR (300 MHz, $CDCl_3$) δ [ppm] 1.04–1.11 (comp, 6H, $CH_2CH_3$), 1.18–1.27 (comp, 6H, $CH_2CH_3$), 1.33 (t, $J_{HH}$=7.2 Hz, 3H, $CH_2CH_3$), 2.41–2.56 (comp, 6H, $CH_2CH_3$), 2.78 (q, $J_{HH}$=7.4 Hz, 2H, $CH_2CH_3$), 4.26 (q, $J_{HH}$=7.2 Hz, 2H, $CH_2CH_3$), 6.59 (d, $J_{HH}$=2.0 Hz, 1H, pyrrole-α-CH), 7.93 (s, 1H, NH), 8.77 (s, 1H, NH); $^{13}$C-NMR (75 MHz, $CDCl_3$) δ [ppm] 14.33, 14.37, 15.72, 15.78, 16.32, 17.56, 17.88, 18.35, 18.45, 59.73, 114.82, 117.69, 119.55, 123.64, 124.99, 125.53, 125.82, 133.41, 161.35.

3,4,3',4',3''',4''',3''',4'''-Octaethyl-1H,1'''H-[2,2';5',2'';5'', 2''']-quaterpyrrole-5,5'''-dicarboxylic acid diethyl ester (7). The mono-α-free bipyrrole 6 (100 mg, 0.31 mmol) is dissolved in a minimal amount of hexanes (ca. 5 mL). A solution of potassium ferricyanide (500 mg) in 20 mL of sat. $NaHCO_3$ was added and the resulting biphasic mixture stirred overnight. After addition of $CH_2Cl_2$ (20 mL), phase separation and chromatographic purification (silica gel; $CH_2Cl_2$/1% methanol), quaterpyrrole 7 was obtained as a dark microcyrystalline solid (38 mg, 38%). $^1$H-NMR (500 MHz, $CDCl_3$) δ [ppm] 1.18–1.23 (comp, 18H, $CH_2CH_3$), 1.28 (t, $J_{HH}$=7.6 Hz, 6H, $CH_2CH_3$), 1.38 (t, $J_{HH}$=7.1 Hz, 6H, $CH_2CH_3$), 2.73 (q, $J_{HH}$=7.6 Hz, 4H, $CH_2CH_3$), 2.80 (q, $J_{HH}$=7.5 Hz, 4H, $CH_2CH_3$), 3.04 (q, $J_{HH}$=7.4 Hz, 4H, $CH_2CH_3$), 3.17 (q, $J_{HH}$=7.4 Hz, 4H, $CH_2CH_3$), 9.29 (s, 2H, NH); $^{13}$C-NMR (125 MHz, $CDCl_3$) δ [ppm] 14.38, 14.69, 15.73, 16.03, 16.58, 17.88, 18.23, 19.24, 19.91, 60.43, 121.55, 127.61, 133.91, 134.13, 141.87, 150.70, 154.60, 161.00, 164.70; HRMS (CI): m/z 629.4069 (HM$^+$), calcd for $C_{38}H_{53}N_4O_4$ 629.4067; UV-vis ($CH_2Cl_2$) $λ_{max}$ [nm] (ε in mol$^{-1}$·L$^{-1}$) 502 (37,900).

Scheme 2

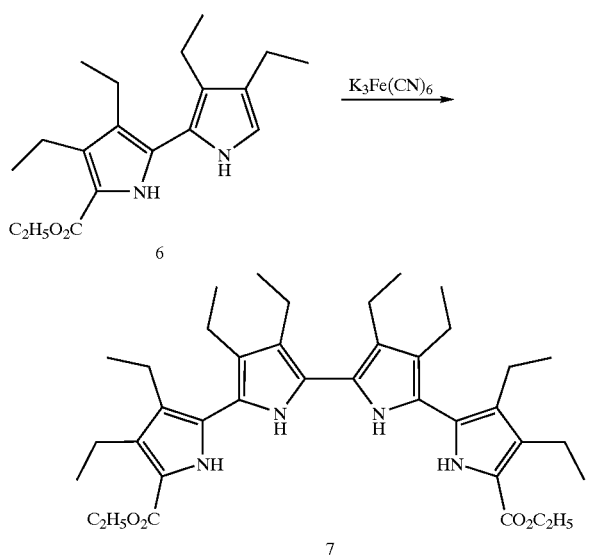

Synthesis of Beta-Substituted Sexipyrroles. Mono-alpha unsubstituted terpyrroles, described in Morosini, P. et al. (*J. Org. Chem.* 1997, 62, 8848–8853) may be used to generate sexipyrroles using the oxidative coupling procedures of this example in a process that is directly analogous to that described for quaterpyrroles above. The choice of appropriate alpha and alpha' substitutents would allow for conversion of the alpha-alpha' products initially obtained into derivatives bearing only hydrogen atoms in these positions. As above, carboxylic acids or their derivatives such as in Scheme 3 would represent preferred alpha or alpha' substituents when such conversions are desired.

Scheme 3

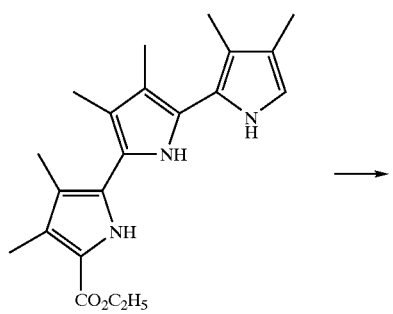

-continued

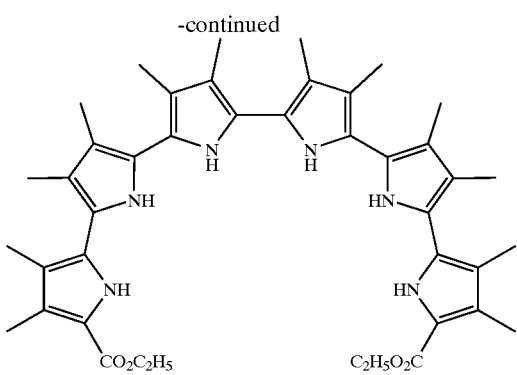

EXAMPLE 2

Derivatives, Multimers, Conjugates and Isomers of Cyclo[n]pyrroles

Cyclo[n]pyrrole derivatives, multimers, conjugates, and isomers are expected to possess useful binding properties for ion, chiral substrate, or neutral molecule separation, for salt binding, for acting as sensors for ions or neutral guests and the like. β-substituted cyclo[n]pyrroles may have substitution at one or more of the β-positions.

The structures of cyclo[n]pyrroles described herein are drawn two dimensionally. This representation obscures the fact that cyclo[n]pyrroles containing more than one asymmetrically-substituted β-position will be formed as a mixture of configurational isomers. For example, a compound containing four asymmetrically substituted β-positions can exist as four different isomers that are chemically distinct from each other and may be separated via HPLC chromatographic techniques. Therefore, as used herein, all two dimensional representations of cyclo[n]pyrroles containing more than one asymmetrically substituted β-position refer to all possible isomers unless otherwise stated.

Derivatives of cyclo[n]pyrroles, in general, may be synthesized from derivatized reactants, or from post synthetic modification. Examples of post synthetic modification reactions of macrocycles are provided by U.S. Pat. No. 5,179,120, Jan. 12, 1993, and U.S. Pat. No. 6,262,257, Jul. 17, 2001. Each patent is incorporated by reference herein.

All N-alkylated Derivatives. Given the unusually large cavity of cyclo[8]pyrroles (the N—N-distance between the two most widely separated pyrroles amounts to a spectacular 7.8 Å), the inventors were intrigued by the possibility of substituting all of the pyrrolic nitrogen atoms by alkyl/aryl groups. As outlined below this substitution proved possible.

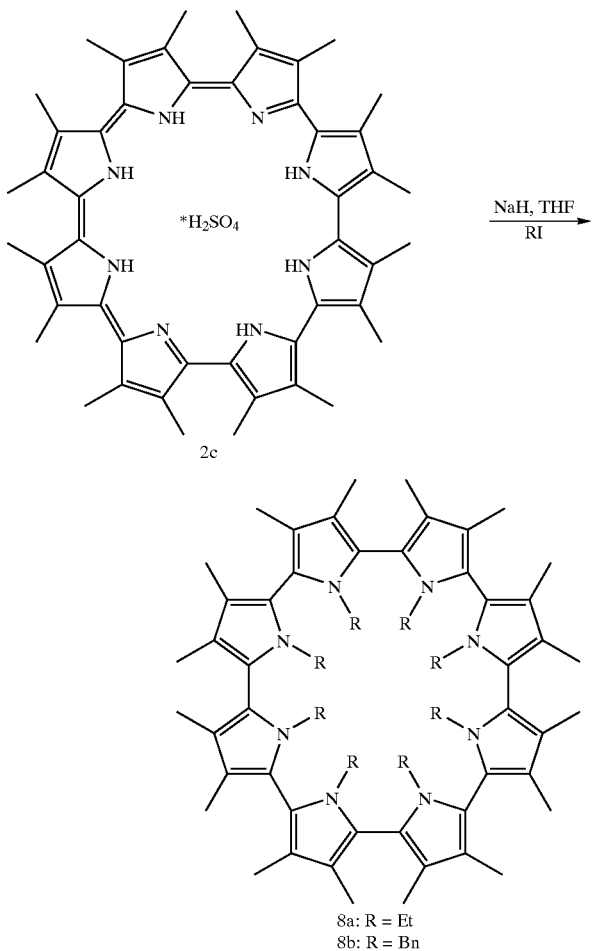

8a: R = Et
8b: R = Bn 2,3,6,7,10,11,14,15,18,19,22,23,26,27,30,31-Hexadecamethyl-33,34,35,36,37,38,39,40-octaethyl-[32]octaphyrin (0.0.0.0.0.0.0.0) (8a). Under an argon atmosphere, cyclo[8]pyrrole (42.1 mg, 50 μmol) was dissolved in 20 ml of dry THF. Sodium hydride (130 mg, 3.25 mmol) was added and stirred at room temperature for 30 minutes. Ethyl iodide (320 μL, 4 mmol) was added and the solution heated under reflux for 12 hours. After cooling to room temperature, 10 mL of aqueous 1M NaOH was added, along with 20 mL of methylene chloride. After drying the organic phases over anhydrous sodium sulfate the solvent was removed in vacuo. The residue was flushed through a short plug of silica gel, using methylene chloride as eluent. Subsequent solvent removal followed by recrystallization from methylene chloride/methanol yielded the all-N-ethylated derivative in form of a white microcrystalline powder (yield: 70%). $^1$H-NMR (300 MHz, CDCl$_3$) δ [ppm] 0.61 (t, $J_{HH}$=6.9 Hz, 24H, CH$_2$CH$_3$), 2.02 (s, 48H, CH$_3$), 3.22 (q, $J_{HH}$=6.9 Hz, 16H, CH$_2$CH$_3$); $^{13}$C-NMR (75 MHz, CDCl$_3$) δ [ppm] 10.06, 15.80, 39.49, 119.23, 122.79; HRMS (CI): m/z 969.7211 (HM$^+$), calcd for C$_{64}$H$_{89}$N$_8$ 969.7210.

2,3,6,7,10,14,15,18,19,22,23,26,27,30,31-Hexadecamethyl-33,34,35,36,37,38,39,40-octabenzyl[32]octaphyrin (0.0.0.0.0.0.0.0)(8b). The same method as described in [0189] is used. The off white product is obtained in 70% yield. $^1$H-NMR (300 MHz, CDCl$_3$) δ [ppm] 1.68 (s, 48H, CH$_3$), 5.09 (s, 16H, benzyl-CH$_2$), 6.34–6.37 (m, 16H, phenyl-H), 6.83–6.88 (m, 16H, phenyl-H), 6.94–6.99 (m, 8H, phenyl-R); $^{13}$C-NMR (75 MHz, CDCl$_3$) δ [ppm] 9.82, 48.91, 121.08, 123.96, 126.50, 126.67, 127.76, 138.17.

Ester Derivatives. To prepare ester derivatives, cyclo[8]pyrrole is deprotonated and the substituent to be added at the β-position is then reacted with the activated cyclo[8]pyrrole, or the cyclo[8]pyrrole is synthesized from a β-substituted pyrrole. The cyclo[8]pyrrole is deprotonated using a base such as n-BuLi, for example. Bromoethylacetate is then added to form a β-monosubstituted ester or a β-diester. This reaction may also be accomplished using other bases such as aryllithium or alkyllithium or in the presence of a coordinating ligand such as tetramethylethylenediamine with an aryllithium or alkyllithium base, for example. Alternatively, other electrophiles may be attached to the activated cyclo[n]pyrrole macrocycle (e.g. CO$_2$, ethylchloroformate, acrylonitrile). β-Substituted cyclo[n]pyrrole esters are useful as reagents for the synthesis of other cyclo[n]pyrrole derivatives as described herein.

Carboxy Derivatives. A β-substituted cyclo[n]pyrrole ester is de-esterified to produce cyclo[n]pyrrole β-acid by heating a solution of NaOH in EtOH/H$_2$O at reflux. The acid may be clarified by adding a strong mineral acid, such as perchloric acid to the cooled reaction solution. It may then be collected by filtration. β-substituted carboxylated cyclo[n]pyrroles are particularly useful for use in further substitution reactions and in the formation of linked dimers, oligomers, and conjugates and for attaching cyclo[n]pyrroles to solid supports.

Alkoxy Derivatives. 3,4-Dimethoxybipyrrole is a starting material for an alkoxy derivatized cyclo[n]pyrrole. A methoxy derivative is expected to show decreased anion binding affinity relative to unsubstituted cyclo[n]pyrrole due to electron donating properties of the methoxy substituents. These types of compounds may be useful as HPLC column media since low affinity constants and fast complexation-decomplexation rates generally lead to efficient separation of substrates.

Halogenated Derivatives. A first method of synthesis of halogenated cyclo[n]pyrroles, such as hexadecahalo[30]octaphyrin, for example, is based on bipyrroles 10a–10c. These bipyrroles are expected to be readily prepared from known pyrroles 9a–9c using standard methodology that involves iodination of the 5-position, Cu(0) promoted Ullmann-type coupling and subsequent saponification and decarboxylation. For standard methods, see Leroy, J., Wakselman, C., Tetrahedron Lett. 1994, 35, 8605–8608; Hodge, P., Rickards, R. W. J. Chem. Soc. 1965, 459–470; Banwell, M. G. et al. Chem. Commun. (Cambridge) 1997, 207–208; and Sessler, J. L., Hoehner, M. C. Synlett 1994, 211–212.

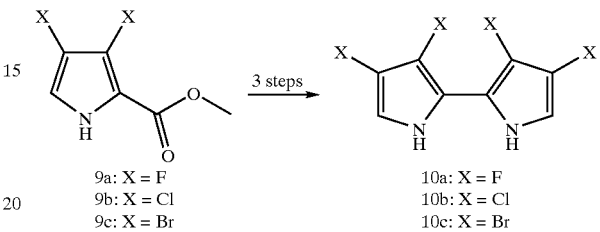

9a: X = F
9b: X = Cl
9c: X = Br

10a: X = F
10b: X = Cl
10c: X = Br

A second method for synthesis of halo-derivatized cyclo[n]pyrroles uses cyclo[8]pyrrole 2, for example, with N-bromosuccinimide, in a similar manner to the method used in U.S. Pat. No. 6,262,257, incorporated by reference herein, for calixpyrrole as detailed in this prior patent.

A halo derivative is expected to show increased anion binding affinity relative to unsubstituted cyclo[n]pyrrole due to the electron withdrawing properties of the bromine substituents. Receptors with an increased anion binding ability are useful as anion sequestering agents (e.g., in removal of sulfate, phosphate nitrate, arsenate, chromate, and pertechnetate pollutants from aqueous environments) or as synthons in reactions to produce further modified cyclo[n]pyrroles.

Hydroxy derivatives. Hydroxy derivatives may be obtained by reduction of ester derivatives or by treatment of the respective alkoxy derivatives with reagents commonly used for cleavage of an ether functionality, such as HI, HBr, or BBr$_3$, for example.

While ester, acid, alkoxy, halo, and hydroxy β-substituents have been described supra, one of skill in the art would be able to synthesize further modified β-substituted molecules in the light of the present disclosure and using standard organic chemical synthesis reactions as described herein. Synthesis of substituted cyclo[n]pyrroles is not limited to the bipyrroles described above (3a–d and 10a–c). Rather, coupling may be performed with a variety of bipyrroles such as the ones found in, for example, U.S. Pat. Nos. 5,756,724 and 5,179,120, incorporated by reference herein.

Amido-cyclo[n]pyrroles. Amido-cyclo[n]pyrroles would be particularly useful as anion binding agents and are synthesized in a similar manner to that described for calixpyrrole 28, 29, or 30 in U.S. Pat. No. 6,262,257, previously incorporated by reference herein. Additionally, amido-cyclo[n]pyrroles would serve as model compounds for cyclo[n]pyrrole-modified silica gels wherein the cyclo[n]pyrrole is linked to the modified silica gel via amide bonds. Molecules having substituents that include long hydrophobic chains are particularly designed for insertion into lipid bilayers and are expected to be useful for transport.

β-Amidocyclo[n]pyrrole dimer. A cyclo[n]pyrrole amide dimer is formed by coupling 1,3-diaminopropane, for example, to a cyclo[n]pyrrole carboxylic acid. The amide is formed as a DMF complex. This type of receptor is expected to be an effective host for poly-anionic guest species. This methodology can be extended to produce cyclo[n]pyrrole trimers, networks of cyclo[n]pyrroles, linear strings of cyclo[n]pyrroles, or dendrimer type arrays of cyclo[n]pyrroles.

β-Amidobenzo-15-crown-cyclo[n]pyrrole. 4'-Aminobenzo-15-crown-5 is coupled to cyclo[n]pyrrole β-monoacid to produce a ditopic receptor which is capable of binding a whole salt (i.e. $Na^++Cl^-$) or a zwitterionic amino acid. The cyclo[n]pyrrole provides an anion binding site and the crown ether a cation binding site, thereby providing a salt complexing agent. Cyclo[n]pyrrole β-monoacid and 4'-aminobenzo-15-crown-5 are dissolved in dry DMF and stirred under an argon atmosphere. Benzotriazol-1-yloxytris(dimethylamino)phosphonium hexafluorophosphate (BOP $PF_6$) and triethylamine in DMF were added and the reaction carried out as described in U.S. Pat. No. 6,262,257. Further cation binding agents that may be coupled to cyclo[n]pyrrole include polyethers, texaphyrins and cryptands for example. Anion binding agents such as sapphyrin or other expanded porphyrins such as rubyrin, rosarin, amethyrin and turcasarin may also be appended to produce polyanionic receptors. Additionally, neutral binding groups such as hydrogen bonding arrays may be appended to the cyclo[n]pyrrole.

Mono-β-ferroceneamidocyclo[n]pyrrole. Cyclo[n]pyrrole acid is dissolved in DMF under an argon atmosphere. Methylaminoferrocene is added followed by BOP $PF_6$ and triethylamine. The reaction is carried out as described in U.S. Pat. No. 6,262,257. The electrochemical behavior of these macrocycles includes multiple oxidation processes occurring in the cyclo[n]pyrrole ring. The ferrocene oxidation wave is distinct from the macrocycle oxidations and can be followed using standard electrochemical techniques (cyclic and square wave). The ferrocene oxidation wave is expected to be perturbed upon addition of anions to the electrochemical solution. The present inventors expect that cyclo[n]pyrroles can be incorporated into an electrochemical anion sensor and operate successfully.

Amidosaccharide-cyclo[n]pyrrole conjugate. Coupling of protected glucosamine with cyclo[n]pyrrole acid derivative will produce a water soluble cyclo[n]pyrrole conjugate in a similar manner as for 36 in U.S. Pat. No. 6,262,257, previously incorporated by reference herein.

A host of hydrophilic substituents can be coupled to a β-mono-acid derivative of cyclo[n]pyrrole; for example, polyethylene glycols, azacrown ethers, crown ethers, phosphate groups, saccharides, modified sugars bearing amino groups, amino alcohols, sulfonyl, chitosan, 2-aminoethylhydrogensulfate, 2-aminoethylphosphoric acid, and the like. Additionally, water solublizing groups, such as sulfonates, phosphates, polyalcohols, polyethers, hydroxyl groups, amino groups, carboxylic acid groups, sulfoxide groups, and other could be incorporated into the molecule via attachment to the starting bipyrrole before formation of the macrocycle.

Chiral cyclo[n]pyrroles. Methods for inducing chirality in macrocycles of the present invention include attaching optically active (chiral, asymmetric, or stereogenic) groups to the molecule via bond formation between functional groups on the cyclo[n]pyrrole and the chiral auxiliary. Chiral macrocycles are useful for recognition and separation of neutral and anionic chiral molecules, such as amino acids, for example.

A chiral auxiliary is attached to the main body of a cyclo[n]pyrrole, for example, by forming an amide bond between a carboxycyclo[n]pyrrole and a chiral, amino group-containing molecule. This can include, but is not limited to, aminoglycosides, chiral amino alcohols, aminocyclodextrins and amino acids. Many different kinds of functional groups can be coupled to form chemical bonds with a cyclo[n]pyrrole and would be known in the light of the present disclosure. One skilled in the art, in the light of the present disclosure, would appreciate that the resulting species would be amenable to attachment to a solid support.

A second method is based on transforming achiral substituents into chiral groups by chiral catalysis, such as, reaction of a non-chiral substituent, such as an alkene, to form a chiral side chain and subsequent anti-selective transformation of the side chain to a chiral moiety. These types of reactions include, but are not limited to, catalytic asymmetric hydrogenation, asymmetric epoxidation and subsequent ring opening, asymmetric diol formation, asymmetric halogenation and asymmetric amino alcohol formation.

Solid-supported cyclo[n]pyrroles. Cyclo[n]pyrrole carboxylic acid derivatives may be attached to a silica gel solid support. For example, a carboxy acid derivative of cyclo[n]pyrrole may be covalently attached to 5μ, trimethyl silyl protected, aminopropyl HPLC-grade silica gel obtained from Phase Separations (Norwalk, Conn.) in the presence of diisopropylcarbodiimide. The cyclo[n]pyrrole-modified silica gel is expected to have some immediate advantages over anion exchange columns and reverse phase columns. With respect to anion exchange chromatography of oligonucleotides, for example, the large concentrations of salt that is normally needed to effect separation is not necessary, thereby removing the mandatory desalting step after chromatography of oligonucleotides before using them in biochemical experiments. The primary advantage that the cyclo[n]pyrroles have over reverse phase columns is the higher resolution and shorter retention times. Additionally, reverse phase chromatography of oligonucleotides is done while they are in a "protected" state and must further be hydrolyzed before use.

The solid support attached to the cyclo[n]pyrrole is not limited to silica gel. Further solid supports include, but are not limited to, polystyrene, polysiloxane, polyacrylamide, Merrifield resins, glass, sepharose, sephadex, agarose, clays, zeolites, and the like, that can be functionalized to allow the formation of a cyclo[n]pyrrole bonded to a solid support.

Ion selective electrodes. Macrocycles of the present invention may be used to generate ion selective electrodes in a further use embodiment. Methods of making cyclo[n]pyrrole-ion-selective electrodes include, but are not limited to, the following examples: attaching, or immobilizing a functionalized cyclo[n]pyrrole to a functionalized polymer and further coating this polymer to an electrode that is sensitive to changes in ionic strength; immobilizing the cyclo[n]pyrrole in a plasticizer and encasing the mixture in a membrane surrounding an electrode that is sensitive to changes in ionic strength; covalently attaching the cyclo[n]pyrrole to an electrode that is sensitive to changes in ionic strength; or coating the electrode with a layer of cyclo[n]pyrrole containing electropolymerizable functional groups, including but not limited to, pyrrole, thiophene or vinyl, and polymerizing the coating on to the electrode.

EXAMPLE 3

Bridged Cyclo[n]pyrroles, and Synthesis thereof

The present example provides novel substituted bridged bipyrroles, and nonsubstituted or substituted bridged cyclo[n]pyrrole macrocycles. Unsubstituted bridged bipyrroles such as 11c are known (see: Berlin, A. et al., *J. Chem. Soc., Chem. Commun.* 1987, 1176–1177; Berlin, A. et al., *Makromol. Chem.* 1990,191, 1497–1511.)

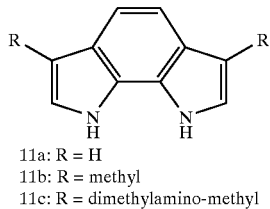

11a: R = H
11b: R = methyl
11c: R = dimethylamino-methyl

Novel substituted bridged bipyrroles provided by the present invention include 12a–12d. They may be prepared as outlined in the scheme below:

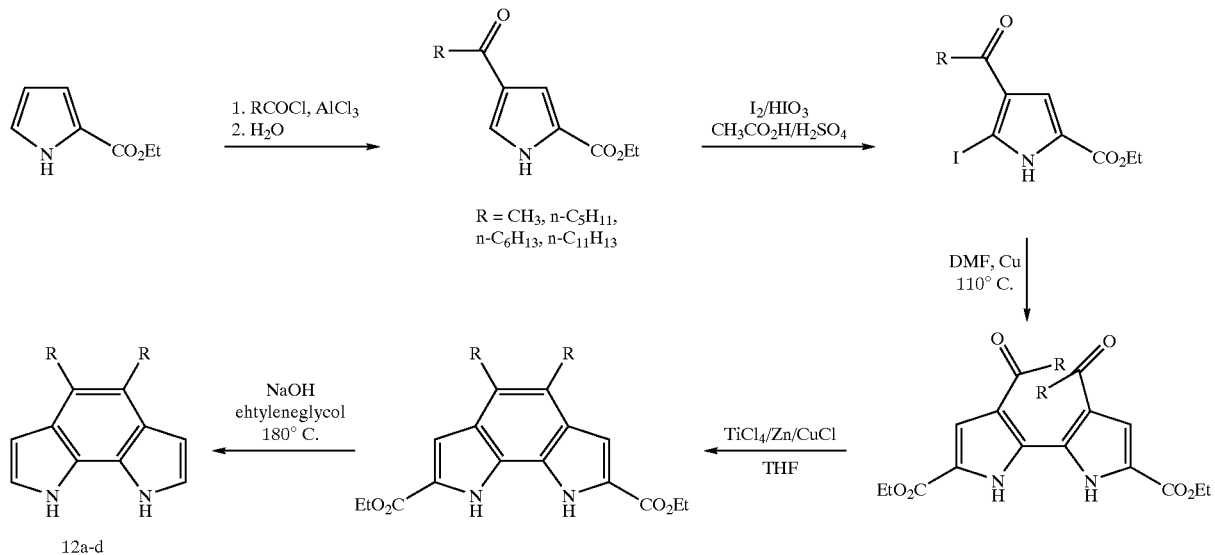

R = CH₃, n-C₅H₁₁, n-C₆H₁₃, n-C₁₁H₁₃

12a-d

Friedel Crafts acylation of pyrrole 2-carboxylate provides the corresponding 4-acyl-pyrrole-2carboxylate which are then transformed into their 5-iodo derivatives. Coupling under standard Ulmann conditions gives rise to the bipyrroles. McMurry coupling and subsequent saponification and decarboxylation provides the bridged bipyrroles 12a–b.

Ethyl 4-acetylpyrrole-2-carboxylate. In a two-neck round bottom flask with an argon inlet, 4.0 g of ethyl pyrrole 2-carboxylate (28.8 mmol) is dissolved in 100 ml of 1,2-dichloroethane. Subsequently, 8.0 g of AlCl₃ is added slowly. A solution of 4.4 ml of acetyl chloride (62 mmol) in 50 ml of 1,2-dichloroethane was then added dropwise over a period of 15 min. After stirring the reaction mixture at room temperature for one hour, it is carefully poured onto 200 g of crushed ice. After hydrolysis, the mixture is transferred into a separatory funnel and the organic phase is separated off. The aqueous phase is extracted with dichloromethane (2×200 ml), and the combined organic phases are washed with a saturated solution of aqueous sodium bicarbonate (1×100 ml) and with water (1×100 ml) before being dried over magnesium sulfate. The solvent is then removed under vacuum. Chromatographic workup (silica gel; 1% methanol in dichloromethane as eluent) yielded the product as a pale brown powder (4.0 g, 76% yield). $^1$H NMR (δ ppm, CDCl₃): 10.41 (s, br, 1H, NH); 7.51 (dd, J=3.34, 1.62 Hz, 1H, α-pyrrolic); 7.28 (dd, J=1.62, 2.31 Hz, 1H, β-pyrrolic); 4.29 (q, J=7.12 Hz, 2H, CO₂Et); 2.39 (s, 3H, Me); 1.31 (t, J=7.12 H, 3H, CO₂Et). $^{13}$C NMR (δ ppm, CDCl₃): 193.55; 161.07; 127.00; 126.54; 124.04; 114.86; 60.83; 27.13; 14.15. Exact mass calculated for C₉H₁₂NO₃ (M+H)= 182.081718, found=182.081495.

Ethyl 4-hexanoyl-2-pyrrolecarboxylate. Starting with 2.0 g of ethyl pyrrole carboxylate (14 mmol) and 4.5 ml (30 mmol) of hexanoylchloride and following a procedure analogous to the one described above, 2.71 g (80% yield) of the desired product is obtained. $^1$H NMR (δ ppm, CDCl₃): 10.70 (s, br, 1H, NH); 7.57 (dd, J=1.61, 3.35 Hz, 1H, α-pyrrolic); 7.29 (dd, J=1.61, 2.48, 1H ; β-pyrrolic); 4.32 (q, 2H, J=7.12 Hz, CO₂Et); 2.74 (t, 2H, J=7.54, α-CO CH₂); 1.68 (m, 2H, β-CO CH₂); 1.34 (t, 3H, J=7.12, CO₂Et); 1.31 (m, 4H, γ,δ-CO CH2); 0.87 (m, 3H, CH₃). $^{13}$C NMR (CDCl₃): 196.57; 161.32; 126.74; 126.65; 123.93; 114.91; 60.87; 39.60; 31.44; 24.28; 22.35; 14.17; 13.77. Exact mass calculated for C₁₃H₂₀NO₃ (M+H)=238.144319, found= 238.143749.

Ethyl 4-heptanoyl-2-pyrrolecarboxylate. Starting with 2.0 g of ethyl pyrrole carboxylate (14 mmol) and 4.2 ml (26 mmol) of heptanoylchloride and following a procedure analogous to the one described above, 2.5 g (70% yield) of the desired product is obtained. $^1$H NMR (δ ppm, CDCl₃): 10.07 (s, br, 1H, NH); 7.53 (dd, J=1.60, 3.35 Hz, 1H, α-pyrrolic); 7.27 (dd, J=1.60, 2.47; 1H; β-pyrrolic); 4.32 (q, 2H, J=7.14 Hz, CO₂Et); 2.73 (t, 2H, J=7.50, α-CO CH₂); 1.67 (m, 2H, β-CO CH₂); 1.33 (t, 3H, J=7.14, CO₂Et); 1.28 (m, 6H, γ,δ,ε CH₂); 0.85 (m, 3H, end-CH₃). $^{13}$C NMR (δ ppm, CDCl₃): 196.32; 161.26; 127.07; 126.24; 124.01; 114.86; 60.99; 39.78; 31.62; 29.05; 24.59; 22.48; 14.30; 13.99. Exact mass calculated for C₁₄H₂₂NO₃ (M+H)= 252.159969, found=252.159072.

Ethyl 4-dodecanoyl-2-pyrrolecarboxylate. Starting with 10.0 g of ethyl pyrrole carboxylate (72 mmol) and 33 ml (144 mmol) of dodecanoylchloride and following a procedure analogous to the one described above, 7.65 g (33% yield) of the desired product is obtained. $^1$H NMR (δ ppm, CDCl₃): 9.66 (s, br, 1H, NH); 7.51 (dd, J=1.61, 3.40; 1H, α-pyrrolic); 7.26 (dd, J=1.61, 2.60; 1H ; β-pyrrolic); 4.33 (q, 2H, J=7.16 Hz, CO₂Et); 2.73 (t, 2H, J=7.53; α-CO CH₂); 1.68 (m, 2H, β-CO CH₂); 1.35 (t, 3H, J=7.16; CO₂Et); 1.23

(m, 16H, alkyl-CH$_2$); 0.85 (t, 3H, J=7.02, end CH$_3$). $^{13}$C NMR (δ ppm, CDCl$_3$): 196.21; 160.96; 127.19; 125.88; 124.09; 114.68; 60.92; 39.81; 31.89; 29.60; 29.58; 29.49; 29.45; 29.41; 29.31; 24.62; 22.66; 14.34; 14.08. Exact mass calculated for C$_{19}$H$_{32}$NO$_3$ (M+H)=322.238219, found=322.238983.

Ethyl 4-acetyl-5-iodopyrrole-2-carboxylate. A 250 ml round bottom flask is charged with 2 g of iodine, a solution of 0.72 g of iodic acid in 10 mL of H$_2$O, 16 mL of acetic acid and 1 mL of sulfuric acid. A solution of 3 g (16.6 mmol) of ethyl 4-acetyl-2-carboxylate in 100 ml of carbon tetrachloride was added at once and the resulting biphasic mixture is heated at 80° C. for 3 hours. After allowing the reaction mixture to cool down to room temperature, the contents of the flask are transferred into a separatory funnel. The organic layer is separated off and subsequently washed with water, 10% aqueous sodium thiosulfate solution and water, before being dried over sodium sulfate. Solvent removal under vaccum, followed by chromatographic workup (silica gel; ether/hexanes, 1:1 as eluent) and subsequent recrystallization from dichloromethane-hexane yielded the product as a white powder (1.70 g, 33% yield). $^1$H NMR (δ ppm, CDCl$_3$): 10.07 (s, br, 1H, NH); 7.22 (d, J=2.68 Hz, 1H, β-pyrrolic); 4.37 (q, J=7.11 Hz, CO$_2$Et); 2.46 (s, 3H, Me); 1.37 (t, J=7.11, 3H, CO$_2$Et). $^{13}$C NMR (δ ppm, CDCl$_3$): 192.51; 160.12; 127.62; 127.45; 117.09; 61.38; 28.17; 14.26. Exact mass calculated for C$_9$H$_{11}$NO$_3$I (M+H)=307.978370, found=307.978781.

Ethyl 4-hexanoyl-5-iodo-2-pyrrolecarboxylate. Starting with 5.9 g of Ethyl 4-hexanoyl-2-pyrrolecarboxylate (24.9 mmol) and following a procedure analogous to the one described above, 2.9 g (33% yield) of the desired product is obtained. $^1$H NMR (δ ppm, CDCl$_3$): 9.85 (s, br, 1H, NH); 7.22 (d, J=2.61 Hz, 1H, β-pyrrolic); 4.37 (q, J=7.18 Hz, CO$_2$Et); 2.78 (t, J=7.42, 2H, CH$_2$); 1.68 (m, 2H, CH$_2$); 1.36 (t, J=7.18 Hz, 3H, CO$_2$Et); 1.32 (m, 4H, CH$_2$); 0.88 (m, 3H, end CH$_3$). $^{13}$C NMR (δ ppm, CDCl$_3$): 195.20; 159.92; 127.60; 127.47; 116.45; 75.25; 61.32; 40.20; 31.4; 23.78; 22.51; 14.37; 13.92. Exact mass calculated for C$_{13}$H$_{19}$NO$_3$I (M+H)=364.040971, found=364.040265.

Ethyl 4-heptanoyl-5-iodo-2-pyrrolecarboxylate. Starting with 1.5 g of ethyl 4-heptanoyl-2-pyrrolecarboxylate (6 mmol) and following a procedure analogous to the one described above, 0.53 g (23% yield) of the desired product is obtained. $^1$H NMR (CDCl$_3$): 9.98 (s, br, 1H, NH); 7.21 (d, J=2.61 Hz, 1H, 3pyrrole H); 4.35 (q, J=7.14 Hz, CO$_2$Et); 2.76 (t, J=7.40, 2H, CH$_2$); 1.66 (m, 2H); 1.35 (t, J=7.14 Hz, 3H, CO$_2$Et); 1.22 (m, 6H, CH$_2$); 0.84 (m, 3H, end CH$_3$). $^{13}$C NMR (CDCl$_3$): 195.10; 159.80; 127.43; 227.00; 116.3; 61.21; 40.12; 31.75; 29.47; 29.34; 9.17; 23.95; 22.53; 14.23; 13.96. Exact mass calculated for C$_{14}$H$_{21}$NO$_3$I (M+H)=378.056621, found=378.056776.

Ethyl 4-dodecanoyl-5-iodo-2-pyrrolecarboxylate. Starting with 3.21 g of ethyl 4-dodecanoyl-2-pyrrolecarboxylate (10 mmol) and following a procedure analogous to the one described above, 0.8 g (18% yield) of the desired product is obtained. $^1$H NMR (δ ppm, CDCl$_3$): 9.74 (s, br, 1H, NH); 7.21 (d, J=2.61 Hz, 1H, β-pyrrolic); 4.36 (q, J=7.10 Hz, CO$_2$Et); 2.78 (t, J=7.42, 2H, CH$_2$); 1.67 (m, 2H, CH$_2$); 1.37 (t, J7.10 Hz, 3H, CO$_2$Et); 1.24 (m, 16H, CH$_2$); 0.86 (m, 3H, CH$_3$). $^{13}$C NMR (δ ppm, CDCl$_3$): 195.20; 159.84; 127.62; 127.51; 116.41; 75.17; 61.28; 40.27; 31.89; 29.62; 29.49; 29.32; 24.11; 22.67; 14.37; 14.09. Exact mass calculated for C$_{19}$H$_{32}$NO$_3$I (M+H)=448.134871, found=448.135617.

3,3-Diacetyl-5,5-dicarboxyethyl-2,2'-bipyrrole. Ethyl 4-acetyl-5-iodopyrrole-2-carboxylate (800 mg, 2.6 mmol) is dissolved in 20 ml of dry DMF, followed by addition of 750 mg of copper powder. The resulting mixture is heated at 110° C. under argon for 48 h and subsequently filtered hot through a plug of celite. It is washed with hot chloroform until the washings are clear. The greenish solution is washed with water before being dried over sodium sulfate. Most of the solvent is removed under vacuum and the resulting yellow precipitate is filtered off, washed with cold methanol and dried, affording the desired product as a pale yellow powder (160 mg, 33% yield). $^1$H NMR (δ ppm, CDCl$_3$): 15.08 (s, br, 2H, NH); 7.51 (d, J=2.56, 2H, β-pyrrolic); 4.45 (q, J=7.12 Hz, 4H, CO$_2$Et); 2.68 (s, 6H, Me); 1.46 (t, J=7.12 Hz, 6H, CO$_2$Et); $^{13}$C NMR (δ ppm, CDCl$_3$): 196.49; 160.05; 130.12; 122.77; 122.16; 120.59; 61.10; 28.72; 14.42.

3,3-Dihexanoyl-5,5-dicarboxyethyl-2,2'-bipyrrole. Starting with 1.0 g of ethyl 4-hexanoyl-5-iodo-2-pyrrolecarboxylate (2.7 mmol) and following a procedure analogous to the one described above, 266 mg (42% yield) of the desired product is obtained. $^1$H NMR (δ ppm, CDCl$_3$): 15.19 (s, br, 2H, NH); 7.48 (d, J=2.49, 2H, β-pyrrolic); 4.41 (q, J=7.10 Hz, 4H, CO$_2$Et); 2.95 (t, J=8.71 Hz; 4H, α-CO CH$_2$); 1.77 (m, 4H, β-CO CH$_2$); 1.43 (t, J=7.10 Hz, 6H, CO$_2$Et); 1.37 (m, 8H, alkyl); 0.90 (t, J=7.00 Hz; 6H; CH$_3$ alkyl). $^{13}$C NMR (δ ppm, CDCl$_3$): 199.19; 160.21; 130.46; 122.66; 119.88; 61.04; 40.80; 31.54; 24.90; 22.49; 14.39; 13.92. Exact mass calculated for C$_{26}$H$_{37}$N$_2$O$_6$ (M+H)=473.265162, found=473.264958.

3,3-Diheptanoyl-5,5-dicarboxyethyl-2,2'-bipyrrole. Starting with 377 mg of ethyl 4-heptanoyl-5-iodo-2-pyrrolecarboxylate (1 mmol) and following a procedure analogous to the one described above, 150 mg (30% yield) of the desired product is obtained. $^1$H NMR (δ ppm, CDCl$_3$): 15.20 (s, br, 2H, NH); 7.49 (d, J=2.54, 2H, β-pyrrolic); 4.41 (q, J=7.10 Hz, 4H, CO$_2$Et); 2.96 (t, J=7.56 Hz; 4H, α-CO CH$_2$); 1.76 (m, 4H, β-CO CH$_2$); 1.43 (t, J=7.10 Hz, 6H, CO$_2$Et); 1.38 (m, 4H, alkyl); 1.31 (m; 8H; alkyl); 0.88 (t, J=7.11; 6H; CH$_3$ alkyl). $^{13}$C NMR (δ ppm, CDCl$_3$): 199.22; 160.24; 130.48; 122.67; 119.92; 61.06; 40.86; 31.63; 29.07; 25.21; 22.51; 14.40; 14.03. Exact mass calculated for C$_{28}$H$_{41}$N$_2$O$_6$ (M+H)=501.296462, found=501.296875.

3,3-Didodecanoyl-5,5-dicarboxyethyl-1,2'-bipyrrole. Starting with 650 mg of ethyl 4-dodecanoyl-5-iodo-2-pyrrolecarboxylate (1.45 mmol) and following a procedure analogous to the one described above, 160 mg (35% yield) of the desired product is obtained. $^1$H NMR (CDCl$_3$): 9.5 (s, br, 2H, NH); 7.48 (d, J=2.54, 2H, β-pyrrolic); 4.40 (q, J=7.10 Hz, 4H, CO$_2$Et); 2.96 (t, J=7.56 Hz; 4H, α-CO CH$_2$); 1.75 (m, 2H, β-CO CH$_2$); 1.43 (t, J=7.10 Hz, 6H, CO$_2$Et); 1.35 (m, 28H, alkyles); 1.31 (m; 4H; alkyles); 0.88 (t, J=7.11; 3H; CH$_3$ alkyl).

2,7-Dicarboxyethyl-4,5-dimethyl-1,8-dihydro-1,8-diazaindacene. To a suspension of 262 mg of zinc powder and 40 mg of copper (I) chloride in 10 mL THF under argon, 0.3 ml of TiCl$_4$ is added dropwise. The resulting mixture is heated at 66° C. for 2 hours. Subsequently, a solution of 64 mg of 3,3-diacetyl-5,5-dicarboxyethyl-2,2'-bipyrrole (0.17 mmol) in 10 mL of THF is added dropwise and the resulting dark mixture is refluxed for 6 hours. The reaction is then carefully quenched with 5 mL of saturated sodium bicarbonate and filtered over a plug of celite. It is washed with dichloromethane until the washings are clear. The filtrate is transferred into a separatory funnel and the organic phase is separated off, washed with water and dried over sodium sulfate. Solvent removal under vaccum, followed by chromatographic workup (silica gel; dichloromethane with 1% methanol as eluent) yielded the product as a greenish powder (10 mg). $^1$H NMR (δ ppm, CDCl$_3$): 10.7 (s, br, 2H, NH); 7.33 (d, J=1.5 Hz, 2H, β-pyrrolic); 4.52 (q, 4H, CO₂Et); 2.48 (s, 6H, Me); 1.45 (t, 6H, CO₂Et). MS: calculated for M+H: 329, found 329.

2,7-Dicarboxyethyl-4,5-dipentyl-1,8-dihydro-1,8-diaza-indacene. Starting with 600 mg of 3,3-hexanoyl-5,5-dicarboxyethyl-2,2'-bipyrrole and following a procedure analogous to the one described above, 280 mg (49% yield) of the desired product is obtained. $^1$H NMR (δ ppm, CDCl₃): 10.5 (s, br, 2H, NH); 7.30 (d, J=1.5 Hz, 2H, b-pyrrolic); 4.45 (q, 4H, CO₂Et); 2.85 (m, 4H, CH₂); 1.65 (m, 4H, CH₂); 1.55 (m, 8H, CH₂); 1.40 (t, 3H, CO₂Et); 0.89 (t, 6H, Me). Exact mass, calculated for $C_{26}H_{37}N_2O_4$ (M+H): 441.275333, found 441.274093.

2,7-Dicarboxyethyl-4,5-dihexyl-1,8-dihydro-1,8-diaza-indacene. Starting with 100 mg of 3,3-heptanoyl-5,5-dicarboxyethyl-2,2'-bipyrrole and following a procedure analogous to the one described above, 10 mg of the desired product is obtained. Exact mass, calculated for $C_{28}H_{41}N_2O_4$ (M+H): 469.306633, found 469.307609.

2,7-Dicarboxyethyl-4,5-diundecyl-1,8-dihydro-1,8-diaza-indacene. Starting with 100 mg of 3,3-dodecanoyl-5,5-dicarboxyethyl-2,2'-bipyrrole and following a procedure analogous to the one described above, 10 mg of the desired product is obtained. Exact mass, calculated for $C_{38}H_{61}N_2O_4$ (M+H): 609.463134, found 609.464964.

In contrast to the unbridged cyclo[n]pyrroles, the bridged derivatives lack interactions between β-substituents. As a consequence, they can reach perfect planarity. This will modulate the optical properties, for instance the extinction coefficients are expected to be higher. Derivatives having long alkyl chains on the periphery are expected to be particularly good candidates for liquid crystals.

Cyclization of 12b. A 1 L round bottom flask was charged with a stir bar, 500 mL of dichloromethane, and a solution of 2.7 g of FeCl₃·6H₂O (10 mmol) in 100 mL of 1 M sulfuric acid. The resulting biphasic mixture was stirred at 300 RPM, while the bipyrrole 12b (0.2 mmol), dissolved in 50 mL of dichloromethane, was added slowly via syringe pump over a period of 9 hours, with the needle submerged into the organic phase. For slow continuous additions, a Sage syringe pump (model M365) was employed. After completion of the addition, the reaction mixture was stirred for 5 more hours. Subsequently, the phases were separated, filtered over celite to remove a black precipitate and the organic phase was dried over anhydrous sodium sulfate. Following filtration, the solvent was removed in vacuo to yield the crude product. After a short time the dark compound fails to dissolve in any organic solvent.

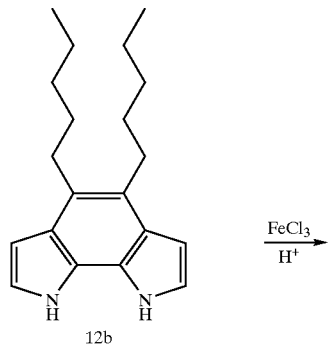

12b

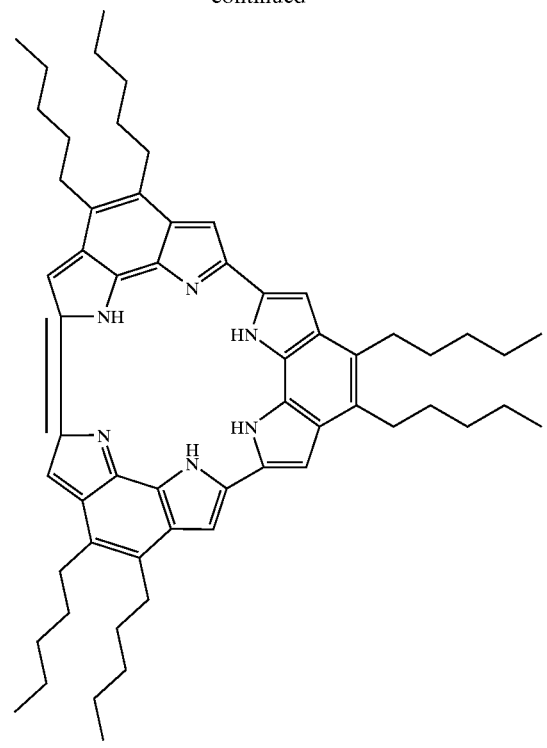

13

Bridged bipyrrole 13: ESI-MS: 883 (M+H, 100%), UV-vis (CH₂Cl₂) $\lambda_{max}$ [nm] 730, >1100.

EXAMPLE 4

Cyclo[n]pyrroles in Ion and Neutral Molecule Binding

The present example provides cyclo[n]pyrrole macrocycles where n is 6–12 for use in binding ions and hydrogen binding neutral molecules.

Figure 6:
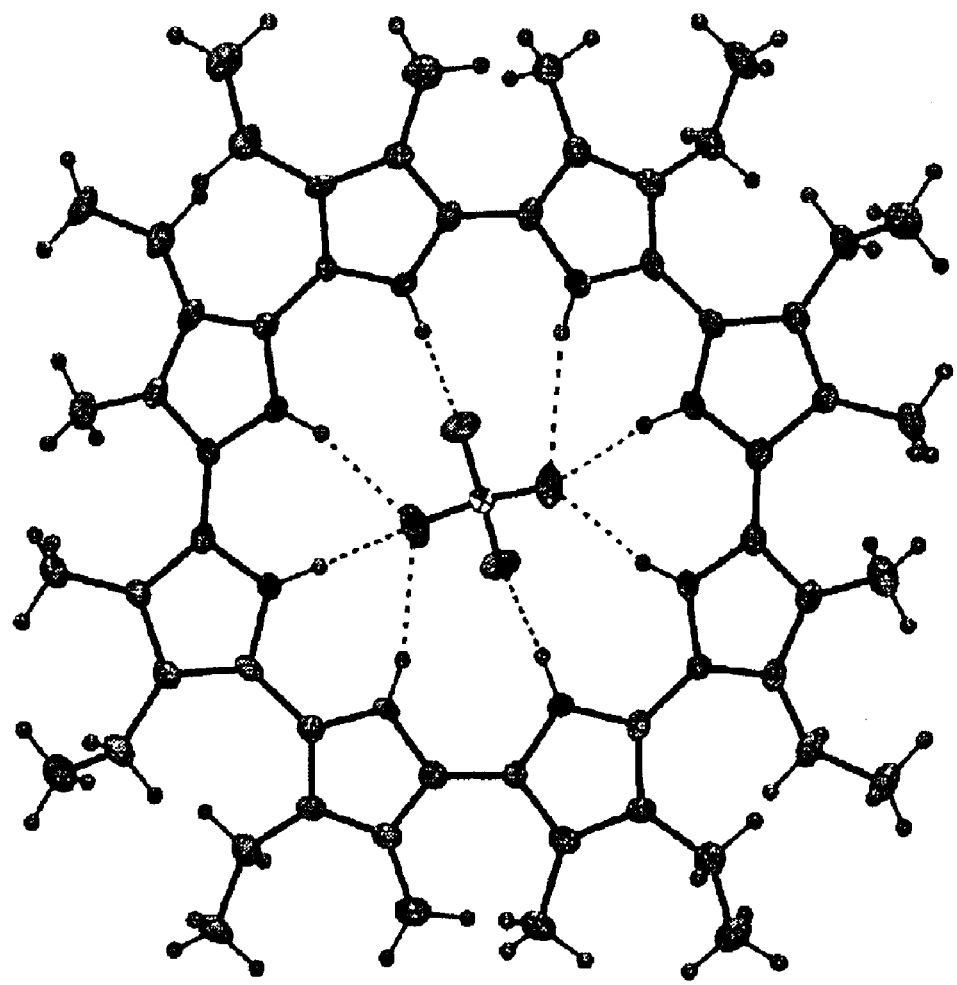
FIG. 6 illustrates ORTEP-POV-Ray views of one of the two crystallographically independent molecules seen in the solid state structure of 2b. The thermal ellipsoids are scaled to the 50% probability level. NH $\cdots$ O bonding interactions range from 1.91 to 2.49 Å.

Anion Binding. The crystal X-ray diffraction analysis and the structure of 2b shown in FIG. 6 reveal a very flat, essentially planar macrocyclic system with a sulfate centrally bound within the cavity. In the solid state eight hydrogen bonding interactions are inferred from the NH—O bond distances which range from 1.91 to 2.49 Å. The result is a structure wherein all four oxygen atoms of the sulfate counter anion interact with all eight pyrrole NH sites present in the middle of what is formally a diprotonated anion receptor. As noted in Example 1, there are two crystallographically independent macrocycle sulfate complexes. This indicates the existence of multiple binding modes and indicates that this and other cyclo[n]pyrroles can act as versatile anion receptors.

Washing a solution of 2b with 1 M aqueous NaOH produces spectral changes that are consistent with the formation of the free-base ($\lambda_{max}$ (ε in mol$^{-1}$·L$^{-1}$) 349 (36200), 455 (15700) and 857 (26900) nm). Treating this species with 1 M H₂SO₄ served to restore completely the spectral features of 2b. Likewise, treatment with 1 M H₃PO₄ led to the formation of a species corresponding to the hydrogen phosphate complex. The sulfate anion observed in the solid state structure of 2b was retained after washing a dichloromethane solution of the dihydrogen sulfate salt with water (pH 7; 3×). These data are supportive of a role of cyclo[n]pyrroles, such as 2a–d, as anion receptors.

The use of oligopyrrolic macrocycles as anion receptors has been demonstrated for a range of systems, including sapphyrins, rubyrins, rubyrins, and calixpyrroles and is taught inter alia in U.S. Pat. Nos. 5,457,195, 5,410,045, 5,530,123, 5,587,478, 5,594,136, 5,744,302, 5,622,945, 5,808,059, and 6,262,257, incorporated herein by reference. These previous systems have structures distinct from the cylco[8]pyrroles and demonstrate different anion selectivities, as judged from the solid state and solution phase studies described supra. They also possess different optical characteristics from the cyclo[n]pyrroles.

The present inventors contemplate the use of cyclo[n]pyrroles as anion receptors, carriers, and sensors. Functionalized cyclo[n]pyrroles could be attached to solid supports and used as stationary media in the chromatographic separation of anions or incorporated into polymers and used as "anion sponges" to capture anions from bulk environments. It is expected that cyclo[n]pyrroles will function best as anion receptors, carriers, sensors, and solid supports for anion separation when maintained in a protonated state. The results of the competitive washing experiments carried out with cyclo[8]pyrrole at pH 7 as described above indicate that unduly low pH will not be necessary and that under most conditions, including physiologically relevant pH ranges, cyclo[n]pyrroles will function as anion receptors.

Methods for attaching oligopyrrolic macrocycles to solid supports or incorporating them therein are taught inter alia in U.S. Pat. Nos. 5,594,136, 5,808,059, 5,744,302, 5,808,059, and 6,262,257, incorporated herein by reference. Methods for using oligopyrrolic macrocycles as carriers are taught inter alia in Furuta, H. et al., *J. Am. Chem. Soc.* 1991, 113, 6677–6678; Sessler, J. L. et al., *Supramolec. Chem.* 1993 1, 209–220; Furuta, H. et al., *Supramolec. Chem.* 1993, 3, 5–8; Sessler, J. L. et al. *Chem. Commun.* 1996, 1119–1120; Allen, W. E. and Sessler, J. L. *ChemTech* 1999, 29, 16–24; and U.S. Pat. No. 5,457,195, 5,410,045, 5,530,123, 5,587,478, 5,622,945, and 6,262,257, incorporated herein by reference. Methods for using oligopyrrolic macrocycles as optical sensors are taught inter alia in Sessler, J. L. and Davis, J. M. *Acc. Chem. Res.* 2001, 34, 989–997. Methods for using oligopyrrolic macrocycles as sensory elements in ion selective electrodes are taught inter alia in Tohda, K. et al. *Sensors and Actuators B* 1993, 13–14, 669–672; Odashima, K. et al., *Supramolec. Chem.* 1994, 4, 101–113; Lin, X. M. et al., *Analytical Sciences*, 1998, 14, 99–108; Král, V. et al., *J. Am. Chem. Soc.* 1999, 121, 8771–8775; and Umezawa, K. et al., *Anal. Chim. Acta* 2001, 426, 19–32. These previous systems have structures distinct from the cylco[8]pyrroles and demonstrate different anion selectivities, as judged from the solid state and solution phase studies described supra. They also possess different optical characteristics from the cyclo[n]pyrroles. However, macrocycles of the present invention may be advantageously used in prior art methods.

Cyclo[n]pyrroles have been shown to bind phosphate groups in solution. DNA and RNA, important biological molecules, contain many phosphate groups. A water-soluble cyclo[n]pyrrole is expected to bind to DNA and RNA. Binding could have the effect of limiting the ability to unwind in the case of DNA, thereby hindering biological functions, or in the case of RNA, could prevent translation. Additionally, oligonucleotides having sequence complementarity to a template molecule may be attached to a cyclo[n]pyrrole for site-specificity. Uses include inhibition of replication and anti-sense therapy.

Of particular importance in all the above cited applications is the ease with which cyclo[n]pyrroles, particularly cyclo[8]pyrroles, may be synthesized, the presence of a central core that provides for good sulfate and phosphate anion recognition, and absorption and emission bands in the near IR spectral region that are modulated upon anion binding. This latter feature makes the cyclo[n]pyrroles uniquely suited for anion recognition applications that involve optical-based near IR sensing. The use of cyclo[8]pyrroles as near IR optical sensors is a preferred embodiment of the present invention.

Varying the substituents on the β-position of a cyclo[n]pyrrole molecule is expected to affect the strength with which a particular anion is held. Attachment of electron-donating substituents (such as methoxy) to the β-position is expected to decrease the stability constants, however, attachment of electron-withdrawing substituents (such as bromine, chlorine, and, especially, fluorine) is expected to increase the stability constants. While varying the electron density of the core is expected to increase or decrease the binding affinities towards anions, groups having a functional moiety at a suitable distance from the macrocycle, and having sufficient flexibility to fold back over the macrocycle also are expected to affect the strength of binding. These moieties can include functional groups, such as amides, sulfamides, ammonium cations, or guanidinium cations, that provide direct stabilization for bound anions. Alternatively, they can consist of a cation coordinating groups, such as lasalocid or crown ether subunits, that increase anion binding affinities by stabilizing the overall anion-cation ion pair complex. Both approaches are known in the oligopyrrole-based anion recognition art and are described, for instance, in Sessler, J. L. and Brucker, E. A. *Tetrahedron Lett.* 1995, 36, 1175–1176; Sessler, J. L. and Andrievsky, A. *Chem. Commun.* 1996, 1119–1120 and in U.S. Pat. Nos. 5,457,195, 5,530,123, and 6,262,257, incorporated by reference herein. Advantages of the present cyclo[n]pyrrole conjugates would include different inherent anion selectivities and the generation of complexes with prominent absorption and emission features in the near IR spectral region. In light of Example 1, the requisite cyclo[n]pyrrole conjugates can be prepared by standard methods, including the coupling of carboxy or amino functionalized cyclo[n]pyrroles with amino or carboxy functionalized ancillary groups containing the subunits in question (e.g., lasalocid, crown ether, guanidinium cations, etc.), for example.

Neutral Molecule Binding. The ability to bind anions via hydrogen bonds, as demonstrated in the solid state structure of cyclo[8]pyrrole 2b, also confers an ability to act as a receptor for a range of neutral substrates, particularly those containing hydrogen bond acceptor subunits (e.g., carbonyl, ether, and carbon-halogen bonds). While the binding interactions are weaker in the case of the neutral substrates, the ability to bind neutral substrates endows the cyclo[8]pyrroles with utility as sensors for the detection of such species, as carriers for their transport, and, after attachment to a solid support, media for their separation and purification via chromatographic or capillary electrophoretic means.

Cation Binding. Large pyrrole-containing macrocycles can act as ligands for cations. They are particularly well suited for stabilizing complexes of large cations, such as those of the lanthanide and actinide series, but also show particular utility for the coordination of more than one cation within the same macrocyclic framework. The use of large pyrrolic macrocycles, containing for the purposes of cation coordination is described inter alia in Burrell, A. K. et al.,*J. Am. Chem. Soc.* 1991, 113, 4690–4692; Weghorn, S. J., et al., *Inorg. Chem.* 1996, 35, 1089–1090; Sessler, J. L. et al., *Chem. Commun.* 1998, 1835–1836; Sessler, J. L. et al., *Angew. Chem.* 2001, 113, 611–614; *Angew. Chem. Int. Ed., Engl.* 2001, 40, 591–594; Sessler, J. L. et al., *Coord. Chem. Rev.* 2001, 216, 411–434; and U.S. Pat. Nos. 4,935,498, 5,252,720, and 5,994,535, incorporated herein by reference. Generally, the complexes are prepared by treating the pyrrolic macrocycle in question, or a reduced form thereof, with an appropriately labile metal salt (e.g. nitrate, acetate, chloride) in an appropriate organic solvent either alone or in the presence of a non-nucleophilic base, or after subjecting the macrocycle to deprotonation by a base prior to treating with metal salt. Depending on the system in question, follow up oxidation will either occur spontaneously or is effected deliberately to produce more stable complexes. In some instances, no follow up oxidation is needed or occurs. Such procedures, which are standard in the art, can be applied to prepare metal complexes of cyclo[n]pyrroles.

The present inventors contemplate that cyclo[n]pyrroles are particularly attractive as metal coordinating ligands. They are larger than other flat pyrrolic macrocycles previously used to coordinate large cations (e.g., isoamethyrin, described in Sessler, J. L. et al., *Angew. Chem.* 2001, 113, 611–614; *Angew. Chem. Int. Ed., Engl.* 2001, 40, 591–594) making them attractive for waste remediation or recovery operations that involve the complexation of various heavy metals (e.g., radioactive actinides, gold, mercury, and the like). Further, they contain six pyrrolic subunits that are potentially subject to deprotonation, meaning they can stabilize complexes wherein the coordinated cations bear a combined charge of +6, they are expected to be superior to other large pyrrolic macrocycles (e.g., amethyrin, described in Weghorn S. J., et al., *Inorg. Chem.* 1996, 35, 1089–1090) for the purposes of forming complexes containing more than one co-bound metal center. Multimetallic species are useful as catalysts and polymetallic complexes of cyclo[n]pyrrroles are expected to have utility as catalysts as well.

Coordination of uranyl(VI) cations with cyclo[6]pyrrole 4. A solution of 0.1 mmol of cyclo[6]pyrrole bis chloride salt in 20 ml dichloromethane is treated in a separatory funnel with 1M NaOH twice. The blueish solution is transferred to a flask. Five drops of triethylamine are added as well as a concentrated methanolic solution of 1 mmol uranyl acetate. After heating and stirring for 12 hours the mixture is subjected to column chromatography (dichloromethane as eluent) and a green-blue band collected in 25% yield. HRMS (CI): m/z 990.5293 (M$^+$), calcd for $C_{48}H_{60}N_6O_2{}^{238}U$ 990.5286; UV-vis (CH$_2$Cl$_2$) $\lambda_{max}$ [nm] ($\epsilon$ in mol$^{-1}$·L$^-$) 386 (204,000), 437 (160,000), 576 (114,000), 641 (155,000).

Figure 2:
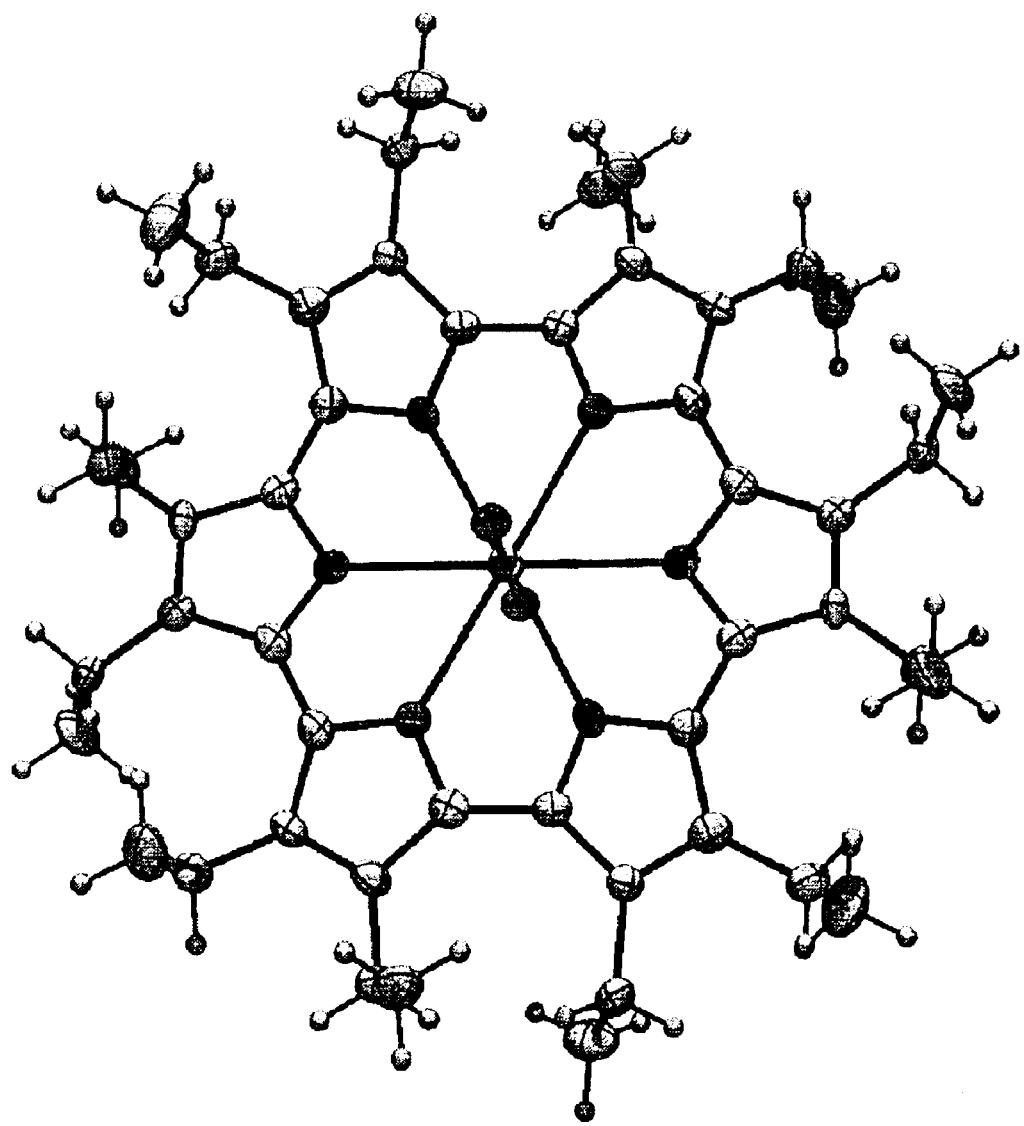
FIG. 2 illustrates an ORTEP-POV-Ray rendered view of the uranyl(UO$_2^{2+}$) complex of cyclo[6]pyrrole.

The X-ray single crystal diffraction analysis shows that the cyclo[6]pyrrole uranyl complex (FIG. 2) is nearly flat. The deviation from planarity of the pyrrolic macrocycle is reflected in the torsion angle of 0.4°. Crystallographic summary: Dark prisms were grown by slow evaporation of CH$_2$Cl$_2$, triclinic, P-1 (No. 2), Z=2 in a cell of dimensions: a=10.5359(2), b=10.7508(2), c=20.5332(3) Å, α=77.995(1), β=77.737(1), γ=84.418(1)°, V=2219.58(7) Å$^3$, $\rho_{calc}$=1.610 g·cm$^{-3}$, F(000)=1080, $\mu$=0.383 mm$^{-1}$. A total of 16548 reflections were measured, 10179 unique (R$_{int}$=0.0510), on a Nonius Kappa CCD using graphite monochromatized Mo Kα radiation ($\lambda$=0.71073 Å) at –120° C. The structure was refined on F$^2$ to an R$_W$=0.1001, with a conventional R=0.0556, 10179 reflections with F$_O$>4[σ (F$_O$)]), and a goodness of fit=1.288 for 545 refined parameters.

Environmental Remediation. Radioactive waste poses a serious problem to the environment. Current technology generates large amounts of secondary solid waste for disposal. Separation and concentration of these wastes is of paramount importance, especially due to long half-lives, and inadequate methods of storage such as sludges or underground tanks of wastewater. Half-life examples for Tc-99, Ni-63, Cs-137, and Sr-90 are 213,000 years, 100 years, 30 years and 28 years, respectively.

Certain of the radioactive metallic wastes exist in an oxidized anionic form and are therefore soluble in aqueous solutions. For example, technetium exists as TcO$_4{}^-$, and nickel, strontium, and cesium can exist in oxidized anionic forms. As shown herein, cyclo[8]pyrrole has demonstrated the ability to bind anions. In a column embodiment, solid-supported cyclo[n]pyrroles could be used to separate out metallic anions from a stream passing through a column. The bound anions could then be eluted from the solid support, and the concentrated eluate is able to be stored in a smaller volume.

In a batch embodiment, solid support-bound cyclo[n]pyrrole could be mixed with a waste solution containing an anion to be removed and the mixture then filtered as a method of extracting the waste anions out of solution. Additionally, a multi-phase extraction system is envisioned where cyclo[n]pyrrole in a first phase extracts anionic waste from another phase, and the waste then is separated for storage or disposal.

Molecules that can be removed from an environmental source are those ions and molecular species that cyclo[n]pyrrole will bind as described herein. In particular, for application to inorganic metal oxoanions; arsenate, tungstenate, pertechnetate, borate, sulfate, or the like, may be removed. Removal of pertechnetate or sulfate from nuclear waste is a particularly preferred application of the present technology. Types of solid supports for attaching cyclo[n]pyrrole include, but are not limited to, those supports provided in the present application in addition to texaphyrin, sapphyrin, or calixpyrrole solid supports.

In one embodiment of the present invention, the cyclo[n]pyrroles are provided to function as highly selective extractants that are capable of removing sulfate anion from nuclear wastes prior to vitrification. Sulfate is a highly problematic contaminant that interferes with nuclear waste remediation because it inhibits the vitrification process. Due to limited solubility in borosilicate glass, sulfate-derived species form a corrosive layer in the melter, thereby requiring high volumes of glass to vitrify sulfate-containing waste. Successful removal of sulfate prior to vitrification thus results in greatly reduced remediation costs. Not only are the glass volumes required for ultimate storage substantially reduced, the lifespan of the melters is expected to be greatly extended in the absence of this corrosion-inducing anion. The result could be millions of dollars in savings. The cyclo[n]pyrroles are stable over a wide range of pH and form complexes with sulfate and/or hydrogen sulfate anion under neutral and acidic conditions. In addition, they release the bound anionic sulfate species at higher pH. Therefore, changes in pH are used to effect release of the anion after extraction. This binding, extraction, and release process may be carried out in a batch manner or in a continuous flow system and may be enhanced via the addition of co-extractants as described herein.

Eutrophication is a serious problem for bodies of water near agricultural lands and urban areas. The accumulation of phosphates and nitrates from fertilizers in lakes, rivers and inland waterways causes toxic algal blooms that poison the water. Algal blooms are also thought to be toxic for humans. Removal of such anions by use of macrocycles of the present invention in a water-treatment plant, for example, would purify the water and provide it for human use and generations of the future.

Purification of domestic water supplies is an increasing necessity in densely populated areas. The macrocycles of the present invention would be useful in filters for attachment to home water supplies for removal of anionic pollutants such as, but not limited to, fluoride, phosphate, sulfate and nitrate.

Further Use in Extraction. Cyclo[n]pyrroles may be bound to or solubilized in traditional membranes such as those derived from phosphatidyl choline, diphosphatidyl glycerol, cholesterol, sphingomyelin, lecithin, or the like, as well as bulk liquid membranes having a hydrophobic phase, i.e, a water immiscible organic solvent, in contact with one or more aqueous phases. Within such membranes, cyclo[n] pyrroles are used to effect the direct extraction of anions, cations, ion pairs, neutral substrates, or zwitterions or to effect through-membrane transfer thereof. The processes of extraction or transport are effected using simple cyclo[n] pyrroles, cyclo[n]pyrrole conjugates, dimers, or multimers such as those described in Example 2. Further, they may be used in combination with a cation coextracting agent or cation exhanger such as detailed below. Extraction would be effected by allowing the cyclo[n]pyrrole-containing membrane or cyclo[n]pyrrole-containing hydrophobic phase to come into contact with one or more aqueous or water-rich phases containing the anion, cation, ion pair, neutral substrate or zwitterion being extracted, whereas transport would be effected by contacting two sides of a cyclo[n]pyrrole-containing membrane with solutions containing different concentrations of the anion, cation, ion pair, neutral substrate or zwitterion being transported. This latter transport can provide a method of effecting extraction. Depending on the desired direction of anion flow and the nature of the species being transported, the transport or extraction process could be effected using either symport or antiport strategies such as provided herein or in, for example, U.S. Pat. No. 5,530,123 or U.S. Pat. No. 5,410,045, which patents are incorporated by reference herein.

Surfactants may also be used to formulate cyclo[n] pyrroles and facilitate their use as extractants and transporting agents. The cyclo[n]pyrroles of this invention may also be incorporated within liposomes and micelles both to generate membranes and hydrophobic phases rich in cyclo [n]pyrroles. Simple cyclo[n]pyrroles and functionalized cyclopyrroles may be employed in this context.

For uses of cyclo[n]pyrroles presented within this application, it is meant that cyclo[n]pyrroles, as well as conjugates, derivatives, or multimers thereof, or solid-supported, membrane incorporated, or liposomal bound cyclo[n]pyrroles may be used, for example. Further, use within a lipophilic bi- or multiphasic system or in the presence of a surfactant is provided. The cyclo[n]pyrroles of this invention may be used by themselves or in conjunction with one or more other coextractants.

EXAMPLE 5

Cyclo[n]pyrroles as Optical Media and for Memory Storage

The present example provides cyclo[n]pyrrole macrocycles where n is 6–12 for use as an optical material.

Figure 5:
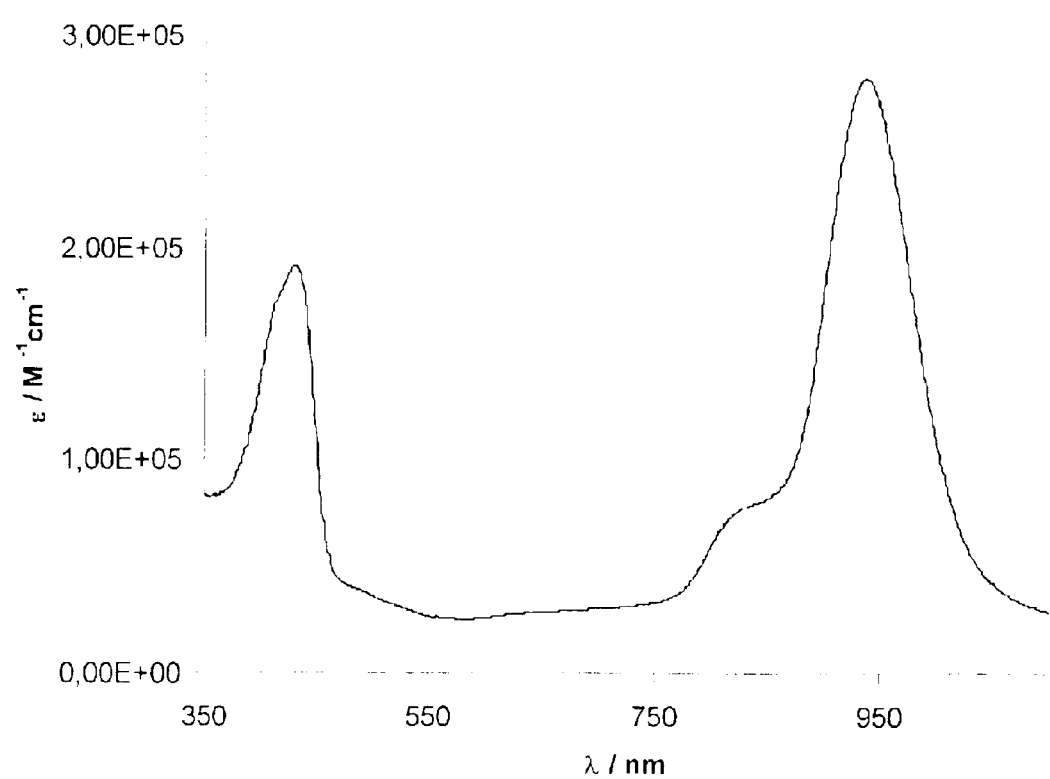
FIG. 5 illustrates the UV-vis spectrum of the bis hydrochloride salt of cyclo[7]pyrrole recorded in dichloromethane.

The UV-vis spectra of the diprotonated cyclo[n]pyrroles 2b, 4 and 5 are shown in FIGS. 3, 5, and 7. The spectra are characterized by strong Soret-type absorbances with extinction coefficients of 80,000 to 265,800 $mol^{-1} \cdot L^{-1}$ and an intense Q-type band that shifts with an increase in the size of the π-system from 792 nm ($\epsilon$=427,500 $mol^{-1} \cdot L^{-1}$) to 1112 nm ($\epsilon$=132,200 $mol^{-1} \cdot L^{-1}$). Both the intensity and the position of the latter bands are remarkable given that Q-type absorption bands in porphyrinoids, including aromatic expanded systems, are generally far less intense than the corresponding Soret transitions and are rarely as far red-shifted as seen in the present instance. Indeed, the present inventors are aware of only two other expanded porphyrin type systems, the doubly cationic hexathiarubyrin of Vogel, (J. L. Sessler et al., in *The Porphyrin Handbook, Vol.* 2 (Eds.: K. M. Kadish et al.), Academic Press, San Diego, 2000, pp. 55–124; and A. Gebauer, Diplomarbeit, University of Cologne, Federal Republic of Germany, 1993) and the octaphyrin(1.1.1.1.1.1.1.1) and nonaphyrin (1.1.1.1.1.1.1.1.1) of Furuta (J.-Y. Shin et al., *J. Am. Chem. Soc.* 2001, 123, 7190) that display Q-type bands at or above 1000 nm. Neither displays anywhere near the intensity of the cyclo[n]pyrroles. E.g. the free-base form of 2b displays weaker transitions at ($\lambda_{max}$ ($\epsilon$ in $mol^{-1} \cdot L^{-1}$)) 349 (36200), 455 (15700) and 857 (26900) nm, that are not as red-shifted as those of the diprotonated form. Nonetheless, these bands are still considerably red-shifted and very intense compared to what is observed for other macrocyclic pyrrole chromophores.

A range of uses, including uses as optical recording and data storage media pigments, nonlinear optical materials, light emitting diodes, electroluminescence devices, liquid crystals, and IR filters based on the surprising structure and unusually strong red-shifted Q-like absorption of the cyclo [n]pyrroles of the present invention are envisioned by the present inventors.

Optical Storage Media. There is considerable commercial activity associated with the development and use of optical recording and data storage media. Compact discs (hereinafter called "CD-Rs") and digital video disks (hereinafter called "DVDs") are typical of such media. Typically such media systems have, at least, a recording layer containing at least a dye and a reflective layer, both on a transparent substrate, and permitting recording and reproduction with a laser beam of a wavelength selected from 620 to 690 nm in the case of CD-Rs and one of a wavelength selected from 770 to 830 nm in the case of DVDs. Many dyes have been used to prepare these kinds of optical media, including phthalocyanine dyes that are the basis for CD-Rs on the market, and numerous other pyrrole-containing dyes, such as metalated tetraarylporphyrins, tetraazaporphyrins, oxo-polysubstituted secoporphyrins, oxoporphyrins, as described in U.S. Pat. No. 5,871,882, incorporated herein by reference, and dicationic tetrapyrrolic expanded porphyrins as disclosed in U.S. Pat. No. 5,658,707, incorporated herein by reference.

The cyclo[n]pyrroles, however, are endowed with a number of novel and chemical properties that the present inventors contemplate to be useful in terms of constructing optical media. For instance, they lack meso positions and are less likely to suffer from photodegradation than other pyrrole-containing pigments when used as the primary recording dye. Further, because certain cyclo[n]pyrroles, such as the diprotonated form of 2b, absorb light at energies that are near or below that of the excitation energy of singlet oxygen (about 1270 nm) but are transparent in the 620 to 690 nm and 770 to 830 nm wavelengths associated with current CD-R and DVD media, they can act as improved photoprotective agents, substances that can be added to optical recording media to improve photostability as described in U.S. Pat. No. 6,319,581, Nov. 20, 2001, herein incorporated by reference. Further, because the absorption spectra of cyclo[n] pyrroles are expected to differ in many instances from all known pyrrole-containing pigments, the present inventors contemplate their use in the construction of multi-layered optical data storage media, wherein two or more recording dye layers, each written and recorded at a different wavelength, are used to achieve high information storage density. Further, possessing optical transitions of lower energy than typical tetrapyrrolic macrocycles, the cyclo[n] pyrroles are expected to function as the energy- or electron-storage subunits in coupled chromophore arrays used for information storage as taught in U.S. Pat. No. 6,324,091, Nov. 27, 2001, herein incorporated by reference.

Nonlinear Optical Materials. In an optical material, when an alternating electric field of visible light wave is incident onto a surface, the heavy nuclei and tightly bound inner electrons of the atoms cannot respond to the rapid changes in the alternating field. However, the loosely bound valence electrons are able to follow the pattern of the field and redistribute according to this pattern, thereby causing a periodical changing polarization. The negative charge density inside the atom corresponds to the oscillating polarization, and thus a weak alternating current is induced at the light frequency. This is termed linear optical behavior and is exhibited by all optical materials.

A nonlinear optical (NLO) material is a material that has optical properties that are modified by light as it passes through the material. The modification of the optical properties may be caused by an induced electronic charge displacement (polarization) that acts as an oscillating dipole. The oscillating dipole may cause the material to emit a photon. When the polarization of the material is linear, the emitted photon has the same frequency as the light incident upon the material. If the polarization is nonlinear, the frequency of the light emerging from the material may be some integer value times the frequency of the incident light. Currently, the ability to translate, amplify, and direct digital traffic depends in part on nonlinear optical (NLO) materials. Thus, materials with nonlinear optical properties are valued as optical switches in fiberoptic communications systems.

The most popular NLO materials have been brittle ceramics, such as $LiNbO_3$. Organic materials that could be poured or molded into a shape, such as polymers, would offer advantages such as exceptional optical qualities, low cost, and ease of fabrication into device structures. Such materials could include molecular fragments displaying NLO activity, or highly colored chromophores, dissolved in or covalently attached to a polymeric host material or incorporated into liquid crystals. A material suitable for widespread industrial use has yet to be synthesized, however.

The use of certain expanded porphyrins, specifically texaphyrin derivatives, as NLO materials has been described (Sun W. F. et al., *Appl. Phys. Lett.* 77 (12): 1759–1761 (2000); Sun W. F. et al., *Appl. Phys. Lett.* 74 (22): 3254–3256 (1999); Sun, W. et al., *Proc. SPIE Vol.* 3472, 127 (1998); Sun, W. et al., *Proc. SPIE Vol.* 3798, 107 (1999)). However, texaphyrins are difficult to synthesize in that they require up to fourteen synthetic steps, and the Q-type absorption band of texaphyrins is not as red-shifted as seen with the present macrocycles.

The cyclo[n]pyrroles, showing strong absorption characteristics in the near IR portion of the electronic spectrum, are thus contemplated by the present inventors as being useful NLO materials. Cyclo[n]pyrroles can be modified structurally and functionally, for example, through the complexation of one or more cations, anion binding, or through the use of different bipyrrolic starting materials in order to fine tune their NLO function as needed.

Liquid Crystals. Abetting their potential utility as NLO materials, is the fact that the cyclo[n]pyrroles possess a structure that renders them amenable for the preparation of liquid crystals. Porphyrin-based liquid crystals are well known and may be obtained by placing long "greasy chain" or appropriately chosen "rod-like" subsituents onto the periphery of the macrocycle as described in Gregg, B. A. et al., *J. Am. Chem. Soc.*, 11:3024–3029 (1989). The present inventors contemplate that replacing the beta-pyrrolic substituents present in, for example, 2b, by long alkyl, alkoxy, ester, polyalkene, polyaryl, or other suitable greasy chain or rod-like substituents would be expected to produce cyclo[8] pyrroles with liquid crystalline properties. Similar methods are expected to prove suitable for preparing liquid crystalline cyclo[n]pyrroles in those instances where n is 7, 9, 10, 11, or 12. The resulting liquid crystals are expected by the present inventors to find use as NLO materials and in a range of applications in which liquid crystals have proved advantageous, including the construction of liquid crystal panel displays, color panel displays, the preparation of photorefractive materials, holographic information storage devices, thermochromic materials, photoconductive films, red-light emitting diodes, and the like.

Cyclo[n]pyrroles, either as liquid crystals themselves, or in forms that are compatible with other liquid crystalline substances, are expected to find uses as colored additives, so-called dopants, rendering other known liquid crystalline materials more beneficial for the applications for which they are normally targeted. Many of these applications have been taught in the case of porphyrins as detailed, for instance, in U.S. Pat. Nos. 5,134,048, 5,231,523, 5,357,357, 5,523,871, 5,718,838, 6,099,750, 6,159,562, 6,265,034, herein incorporated by reference. The cyclo[n]pyrroles of the present invention would offer a number of advantages, including ease of synthesis, red-shifted lowest energy optical properties, and different redox properties.

Photoluminescent light emission is where a substance is excited by external light resulting in the emission of longer-wavelength light. The phenomenon in which a substance is excited by flowing a current through it to emit light, as in an LED, is referred to as electroluminescence. Cyclo[n]pyrroles are contemplated for use in photoluminescent and electroluminescent methods. LEDs wherein a cyclo[n]pyrrole or reduced cyclo[n]pyrrole is doped at various concentrations within a light absorbing host layer are an embodiment of the invention. In particular, replacement of porphyrin or reduced porphyrin in the methods of U.S. Pat. No. 6,339,290, of octaethylporphine in the methods of U.S. Pat. No. 6,303,238 or of phthalocyanine in the methods of U.S. Pat. No. 5,409,783 is contemplated. Said patents are incorporated by reference herein. The red-shifted visible and near IR absorbing properties of the cyclo[n]pyrroles allows them to be used as absorptive species to detect long-wavelength light. When embedded in another absorptive material as a dopant, cyclo[n]pyrroles could enhance the efficacy of the absorptive material allowing devices with improved sensitivity for light in the far visible and near IR to be made. Such devices could prove useful in the construction of near IR cameras, for example.

A further use of cyclo[n]pyrroles of the present invention that takes advantage of the multiple oxidation states possible for these macrocycles is as a dopant for semiconductor materials in photovoltaic cells. Semiconductors must be made separately into positive and negative materials to create an electric field at an interface of the two materials. Silicon is still the most widely used semiconductor material. The process of "doping" introduces either phosphorus or boron into the silicon crystal to provide free electrons or a deficit of electrons, respectively. The electron flow that results from proximity of the materials creates an electric field at the surface where these materials meet, thus making the electrons available for an electrical circuit. A dopant therefore is a material that has an extra electron or is lacking an electron. Other semiconductor materials use the same principle but in different ways, e.g., CuInSe2 and CdTe are made from layers of materials, or CaAs is modified with indium, phosphorus, or aluminum to provide positive and negative materials. In light of the readily accessible charge states of oxidized, neutral, and reduced available for the cyclo[n]pyrroles as provided in the detailed description herein, cyclo[n]pyrroles may be used either as an electron donating dopant or as an electron deficient dopant for use in semiconductors.

Electrochromism is defined as a reversible and visible change in the transmittance and/or reflectance of a material as a result of electrochemical oxidation or reduction. Electrochromism is found in a variety of organic and inorganic materials including conjugated electroactive polymers. The radical changes that occur in the optical absorption spectrum of conducting polymers upon doping allows them to be used as both cathodically and anodically coloring materials in electrochromic devices. Cyclo[n]pyrrole is expected to be useful both as a dopant and as an electrochromic material itself.

Cyclo[n]pyrroles can also be incorporated into other substrates, including polymeric matrices. The optical properties of the resulting systems could render them useful for many of the same applications for which the liquid crystal-based materials described supra are expected to prove advantageous. These applications include, but are not limited to, the preparation of flat panel color displays, photorefractive materials, holographic information storage devices, thermochromic materials, photoconductive films, and red-light emitting diodes.

EXAMPLE 6

Cyclo[n]pyrroles as Infrared Filters or Sensors

As set forth in Examples 4 and 5, the protonated form of cyclo[8]pyrrole has an intense red-shifted Q-type absorption band at 1112 nm ($\epsilon=132,200$ mol$^{-1}\cdot$L$^{-1}$), and the free base form has a red-shifted absorption band at 857 nm. These properties indicate that cyclo[8]pyrrole may be used as an infrared filter, while allowing visible light to pass. The cyclo[8]pyrrole protonated form has an almost 700 nm "gap" between the Soret and Q-like absorption bands, thereby having no significant ground state absorption in the visible portion of the electromagnetic spectrum and light of that wavelength would pass.

Sources of infrared radiation are sunlight and a common infrared light laser, the solid-state neodymium:yttrium-aluminum garnet "Yag" laser that emits infrared light at 1,064 nm. Infrared rays heat up matter. An infrared filter can keep infrared light from heating up surfaces.

A cyclo[n]pyrrole polymer or copolymer may serve as a near infrared filter or near infrared sensor. A near infrared filter or sensor may be in the form of a film or coating on the surface of a transparent substrate or as a freestanding film or sheet. An infrared absorbing substrate or sheet can be used as a filter, such as a band pass filter, an optical filter or a heat-absorbing filter.

Near infrared filters that are cyclo[n]pyrrole-based are useful for protection against near infrared radiation in an application where the filtering out of wavelengths of light of about 800 nm to about 1300 nm is desired. Such applications include the coating of windows, eyewear protection in the form of glasses, goggles, anti-flash goggles, helmets, shields, or outer clothing; coating for greenhouses, for example.

A further use of a cyclo[n]pyrrole-based near infrared filter is as an optical filter in a plasma display panel (PDP) of flat panel displays, for example. The plasma display panel emits infrared rays and remote controls may malfunction while the plasma display panel is used. Therefore, emitted infrared rays from the PDP can be shielded by cyclo[n]pyrrole based film especially since cyclo[n]pyrroles have intense absorption in the infrared region and essentially no absorption in the visible region. In light of the present disclosure, the present inventors expect that the cyclo[n]pyrrole-based films may be used in a manner similar to that of U.S. Pat. No. 5,945,209, Aug. 31, 1999, incorporated by reference herein.

Near infrared sensors that are cyclo[n]pyrrole-based are useful for detecting emitted light in the near infrared range, such as for tracking Yag guided missiles. Such sensor material may provide a decoy for airborne infrared light lasers.

A reflector that is cyclo[n]pyrrole based is useful for reflecting wavelengths of light of about 800 nm to about 1300 nm. The military uses a reflector of electromagnetic radiations to create echoes for confusion purposes such as chaff, rope and corner reflectors. In electronic warfare, a balloon-supported confusion reflector would produce fraudulent echoes. The present inventors contemplate use of cyclo[n]pyrrole based reflective materials for such applications. Such reflective surfaces would obviate the targeting of a "Yag" laser guided missile, for example.

Cyclo[n]pyrroles or polymer thereof may be added to a thermal fixing acceleration type toner. The fixing reaction of the toner can be accelerated by absorbing infrared light. Cyclo[n]pyrroles or a polymer thereof may be used as an infrared absorbing ink or paint. An invisible image can be formed by using the infrared absorbing ink. The infrared absorbing paint can be used as an anti-reflection material for a laser beam.

EXAMPLE 7

Cyclo[n]pyrroles for Biomedical Uses

The properties of cyclo[n]pyrroles allow for a number of useful applications within the biomedical field such as, for example, drug-delivery systems, anion transport through membranes, selective anion channel formation, dialysis, blood filtration, viral inhibition, photodynamic therapy, imaging, chemosensitization, or radiation sensitization.

Anion transport. As demonstrated by the solution phase anion binding studies described in Example 4, the cyclo[n]pyrroles are expected to be at least monoprotonated at physiological pH. As such, they are expected to bind at least one chloride anion per macrocycle via hydrogen bonding interactions. These interactions will be stronger in nonpolar milieus, such as those present in membranes, and weaker in aqueous environments. Thus, as true for other expanded porphyrin and oligopyrrolic systems, including those described in U.S. Pat. Nos. 5,457,195, 5,410,045, 5,530,123, 5,622,945, 5,587,478, and 6,262,257 incorporated herein by reference, cyclo[n]pyrroles are expected to act as efficient carriers for chloride anions. Unless specifically rendered water soluble via the attachment of water solubilizing groups, cyclo[n]pyrroles are hydrophobic species, even when protonated, and will naturally localize within cellular membranes. There, they can facilitate the through-membrane transfer of chloride anions by virtue of their ability to bind chloride anions better at an aqueous-membrane interface where the chloride anion concentration is high, carry it through the membrane as a charge neutralized chloride anion-protonated cyclo[n]pyrrole complex, and release it at a second aqueous-membrane interface where the chloride anion is low. Used in this fashion, cyclo[n]pyrroles could be used to treat cystic fibrosis and other diseases, such a Bartter's syndrome and Dent's disease, that arise as the result of malfunctioning chloride anion channels. Alternatively, an array of cyclo[n]pyrroles could be designed to span a membrane requiring selective chloride transport where anions are transferred by "handing off" the anion to the next cyclo[n]pyrrole. In both cases, cyclo[n]pyrroles would be used to alleviate the problem of chloride transport and ultimately treat the disorder. Since the cyclo[n]pyrroles are easy to make in light of the present disclosure and possess high chemical stability, the cyclo[n]pyrroles would offer an advantage over other oligopyrrolic macrocycles whose potential benefit in this kind of application have been suggested in, e.g., Allen, W. E. and Sessler, J. L. *ChemTech* 1999, 29, 16–24.

Drug delivery. Another application of anion transport is use of the macrocycles of the present invention as a drug delivery system. Many potential anti-viral agents that display activity ex-vivo are phosphorylated nucleosides that are too polar to pass through cell wall membranes. Nucleobase-substituted cyclo[n]pyrroles are expected to transport the nucleobase through membranes. Nucleobase, as used herein, means a purine or pyrimidine base, nucleoside (saccharide derivative), nucleotide (saccharide-poly- or mono-phosphate derivative) or natural or synthetic analogues thereof. Attachment of a nucleobase to the cyclo[n]pyrrole may occur at a functional group of the β-position or a pyrrolic-nitrogen. One nucleobase may be attached, however, any number or diversity of nucleobases is expected to be attached to the cyclo[n]pyrrole. Attachment can occur using methods such as: amide bond formation, Stille coupling, ester formation, or the like. The nucleobase appended cyclo[n]pyrrole will coordinate to both the phosphate group and nucleoside of the anti-viral drug, forming a hydrophobic complex which is expected to pass through cell wall membranes and decomplex, releasing the drug into the interior of the cell.

Dialysis and blood filtration. Kidney failure is a condition that affects a significant portion of the people in the world due to various ailments. Cyclo[n]pyrroles have utility for ex vivo applications such as dialysis or filtration of ex vivo bodily fluids. Current dialysis employs an anion gradient to bring anions across a membrane, thereby establishing an equilibrium. Cyclo[n]pyrroles could be used to bind the anions once they came across the membrane forcing the equilibrium to shift in favor of additional waste anion removal by not allowing an equilibrium to form. The cyclo[n]pyrroles could either be water soluble and partitioned on one side of a membrane or bound to a solid support to prevent diffusion into the blood supply. Phosphates, sulfate, chloride, and other toxins such as drug metabolites (resulting from normal or impaired metabolism of pharmaceutical agents or drug overdoses), anionic wastes or urea contained in the blood or other bodily fluids are expected to be removed by exposure to macrocycles of the present invention. The affinity for sulfate and phosphate anions demonstrated by cyclo[8]pyrrole is expected to make the cyclo[n]pyrroles of particular value for dialysis applications. However, cyclo[n]pyrroles are expected to demonstrate selectivities for other anions. Further, these latter systems and the cyclo[8]pyrroles can be functionalized to render them specific for other anions or to optimize their neutral substrate binding ability; this would render them of use in various ex vivo filtration protocols.

Photodynamic therapy. Photodynamic therapy (PDT) is a treatment technique that uses a photosensitizing dye and non-damaging light corresponding to the sensitizer's absorption profile to produce cytotoxic materials, such as singlet oxygen, from benign precursors when irradiated in the presence of oxygen. Other reactive species such as superoxide, hydroperoxyl, or hydroxyl radicals may be involved in the consequent irreversible damage to biological components. The effectiveness of PDT is predicated on three additional factors: i) The photosensitive dyes used in PDT preferably have the ability to localize at the treatment site as opposed to surrounding tissue. ii) The high reactivity and short lifetime of activated oxygen means that it has a very short range (~0.1 mm) and is unlikely to escape from the region in which it is produced; cytotoxicity is therefore restricted to the precise region of photoactivated drug; iii) Developments in light delivery, such as lasers, light emitting diodes, and fiber optics, allow a beam of intense, non-damaging, light to be delivered accurately to many parts of the body. For a review of photodynamic therapy, see U.S. Pat. No. 5,252,720 incorporated by reference herein.

Photosensitive cyclo[n]pyrroles may be used for photodynamic therapy. A photosensitive cyclo[n]pyrrole may be a free-base cyclo[n]pyrrole, a protonated cyclo[n]pyrrole, or may be metallated. The term "photosensitive", as used herein, means that upon photoirradiation by light associated with the absorption profile of cyclo[n]pyrrole, cyclo[n] pyrrole effects the generation of oxygen products that are cytotoxic. Cytotoxic oxygen products may be singlet oxygen, hydroxyl radicals, superoxide, hydroperoxyl radicals, or the like. For generating singlet oxygen, the cyclo[n]pyrrole may be used in its free, metal-free form, in the form where one or more of the central pyrrolic NH protons are replaced by an alkyl, aryl, silyl, or BOC substituent, or in the form of a metal complex. A preferred metal in a cyclo[n]pyrrole used for photodynamic therapy is a diamagnetic metal. Presently, a preferred diamagnetic metal is Lu(III), La(III), In(III), Zn(II), or Cd(II) and a most preferred diamagnetic metal is Lu(III). A preferred cyclo[n] pyrrole has absorption maxima at wavelengths at or below that associated with the triplet or singlet oxygen absorption band (ca. 1270 m).

For photodynamic therapy methods of the present invention, the co-therapeutic agent is light. After the photosensitizing cyclo[n]pyrrole has been administered, the tissue being treated is irradiated at a wavelength similar to the absorbance of the cyclo[n]pyrrole, usually either about 420 nm or about 1100 nm, for the diprotonated cyclo[8] pyrrole 2b of Example 1, or for the free base form of 2b at about 350, 455, or 860 nm. Due to the strong Soret band at 397 nm and particularly the Q type absorbance at 792 nm ($\epsilon$=427.500 mol$^{-1}\cdot$L$^{-1}$), cyclo[6]pyrrole 4 is provided as one embodiment of an extremely powerful photosensitizer. In the present photodynamic therapy methods, the light source may be a laser, a light-emitting diode, or filtered light from, for example, a xenon lamp or a near IR light source, including a neodymium YAG laser operating at its fundamental wavelength of 1064 nm. Depending on the choice of cyclo[n]pyrrole employed and its specific absorption properties, the light may have a wavelength range of about 390–550 nm or 750–1200 nm, preferably about 400–450 nm, 770–820 nm or 1000–1200 nm in the case of neutral and protonated cyclo[6] and –[8]pyrroles, respectively, and more preferably about 850 nm and 1100 nm in the case of these two forms of cyclo[8]pyrrole, respectively. The light may be administered topically, endoscopically, or interstitially (via, e.g., a fiber optic probe). A wavelength in this near IR range is especially preferred since blood and bodily tissues are relatively transparent at longer wavelengths and, therefore, treatment results in less tissue damage and better light penetration. The fluence and irradiance during the irradiating treatment can vary depending on type of tissue, depth of target tissue, and the amount of overlying fluid or blood. Heat arising from irradiation of the tissues can be a problem, either as the result of direct photoirradiation or as a consequence of poor singlet oxygen production. However, it can also provide a mechanism for inducing a desired cytotoxic reaction.

For example, a cyclo[n]pyrrole bearing water solubilizing substituents is administered in solution containing 2 mg/ml optionally in 5% mannitol, USP. Dosages of about 0.01 or 0.1 mg/kg to about 1.0 or 10.0 mg/kg, preferably 5.0 mg/kg may be employed, up to a maximum tolerated dose that is determined in standard studies. The cyclo[n]pyrrole is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

Dose levels for certain uses may range from about 0.05 $\mu$mol/kg to about 20 $\mu$mol/kg administered in single or multiple doses (e.g. before each fraction of light). The lower dosage range would be preferred for intra-arterial injection or for impregnated stents.

The co-administration of a sedative (e.g., benzodiazapenes) and narcotic analgesic are sometimes recommended prior to light treatment along with topical administration of Emla cream (lidocaine, 2.5% and prilocaine, 2.5%) under an occlusive dressing. Other intradermal, subcutaneous and topical anesthetics may also be employed as necessary to reduce discomfort. Subsequent treatments can be provided. In certain circumstances involving particular sensitivity to light, the treating physician may advise that certain patients avoid bright light for about one week following treatment.

The optimum length of time following cyclo[n]pyrrole administration until light treatment can vary depending on the mode of administration, the form of administration, and the type of target tissue. The cyclo[n]pyrrole is expected to persist for a period of minutes to hours, depending on the cyclo[n]pyrrole, the formulation, the dose, the infusion rate, as well as the type of tissue and tissue size.

After the photosensitizing cyclo[n]pyrrole has been administered, the tissue being treated is photoirradiated at a wavelength similar to the absorbance of the cyclo[n]pyrrole cited in examples supra. The light source may be a laser, a light-emitting diode, or filtered light from, for example, a xenon lamp; and the light may be administered topically, endoscopically, or interstitially (via, e.g., a fiber optic probe). Preferably, the light is administered using a slit-lamp delivery system. The fluence and irradiance during the photoirradiating treatment can vary depending on type of tissue, depth of target tissue, and the amount of overlying fluid or blood. For example, a total light energy of about 100 J/$Cm^2$ can be delivered at a power of 200 mW to 250 mW depending upon the target tissue.

Preferred tissues for photodynamic therapy using cyclo[n]pyrroles include atheroma, tumors, or other neoplastic tissue, neovascular-related diseases, as well as other conditions that are responsive to photodynamic therapy such as restenosis. The neoplastic tissue may be leukemia, lymphoma, carcinoma, or sarcoma, for example.

Imaging. Cyclo[n]pyrroles are expected to absorb and emit light in the near IR where interference from endogenous tissues and pigments is minimal. As such, they may be used for imaging using fluorescent detection, IR absorption spectroscopy, x-ray irradiation, Raman scattering, magnetometry (bioluminiscence) or optical coherence tomography, for example. Further, cyclo[n]pyrroles complexed with a paramagnetic metal cation may be used for magnetic resonance imaging. Disease loci of a subject, such as tumors, restenotic tissue, atheromatous plaque, or unstable or friable plaque are expected to be imaged based on the observation that other, smaller and harder to make expanded porphyrins, such as texaphyrin and sapphyrin, localize to these sites as detailed inter alia in Mody, T. D. et al., in *Progr. Inorg. Chem.*, 2001, 49, 551–598, Karlin, K. D., ed., J. Wiley & Sons, New York; and in U.S. Pat. Nos. 5,252,720, 5,272,142, 5,451,576, 5,543,514, 5,733,903, or 6,022,526, incorporated by reference herein. This biolocalization is expected to be fine-tuned by the choice of beta pyrrolic substitutents, as it is in the case of other oligopyrrolic macrocycles.

Detectable cyclo[n]pyrroles may be imaged in a number of ways, for example, fluorescent cyclo[n]pyrroles may be used for detection. The term "fluorescent", as used herein, means that upon photoirradiation by light associated with the absorption profile of cyclo[n]pyrrole, light is emitted at a longer wavelength by the irradiated cyclo[n]pyrrole. Cyclo[n]pyrroles bearing no central metal cation or complexed with diamagnetic cations such as Y(III), Lu(III), or Cd(II) are presently preferred as fluorescent cyclo[n]pyrroles, for example. Cyclo[n]pyrroles can also be detected by absorption spectroscopy and, in favorable cases, by simple so-called naked-eye visualization. For magnetic resonance imaging, preferred paramagnetic metal cation complexes include Mn(II), Mn(III), Fe(III), or trivalent lanthanide metals other than La(III), Lu(III), and Pm(III). Presently, the more preferred paramagnetic metal is Mn(II), Mn(III), Dy(III), or Gd(III); most preferably, Gd(III). Any of various types of magnetic resonance imaging can be employed in the practice of the invention, including, for example, nuclear magnetic resonance (NMR), and electronic spin resonance (ESR) spectroscopy. Gamma particle detection may be used to image a cyclo[n]pyrrole complexed to a gamma-emitting metal. Chromium-51, gallium-68, technetium-99, or indium-111 are preferred metals for complexing to cyclo[n]pyrroles for gamma particle scanning. Monochromatic X-ray photon sources may be used for imaging also. Tc-99m is a high energy form of technetium used in imaging for the detection of tumors. Tc-99m$O_4^-$ or any other anion containing technetium-99m may be coordinated to a cyclo[n]pyrrole and used as an imaging agent. Preferred imaging techniques include positron emission tomography, scintillation counting, or radiological imaging.

Chemosensitization. Chemosensitizers are chemical agents or maneuvers traditionally employed in cancer treatment, which are not cytotoxic in themselves, but modify the host, the tumor or a chemotherapeutic agent so as to enhance anticancer therapy. Noncancerous conditions that also employ chemosensization include treatment of atheroma, or restenosis as well as inflammatory disease. Cyclo[n]pyrroles are expected to be used as chemosensitizers for enhancing the cytotoxicity of a variety of chemotherapeutic agents having differing mechanisms of action and useful for treating disease. The red-shifted absorption spectrum of cyclo[n]pyrroles means that the gap between the highest occupied and lowest unoccupied molecular orbitals is relatively small in cyclo[n]pyrroles and that cyclo[n]pyrroles are easier to reduce than macrocycles not having such a red-shifted spectrum, such as porphyrins. Further, the choice of the number of pyrroles in the cyclo[n]pyrrole or changing the peripheral substituents is expected to be a way of modulating the redox potential of the macrocycle.

When administered, chemotherapeutic agents are in contact with diseased tissue such as tumors or plaque, for example. Certain currently available chemotherapeutic agents traditionally used in cancer chemotherapy are expected to be effective with cyclo[n]pyrroles in treating disease. For example, bioreductive agents such as 2-nitroimidazoles and intercalating agents, antioxidants such as probucanol, vitamin E, and L-arginine, hyaluronic acid, a cyclodextrin derivative, an angiotensin converting enzyme (ace) inhibitor such as cilazapril, and colchicine, an alkylating agent such as a nitrogen mustard, an ethylenimine or a methylmelamine, an alkyl sulfonate, a nitrosourea, or a triazene; an antimetabolite such as a folic acid analog, a pyrimidine analog, or a purine analog; a natural product such as a vinca alkaloid, an epipodophyllotoxin, an antibiotic, an enzyme, a taxane, or a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog are contemplated as chemotherapeutic agents for use with macrocycles of the present invention. Preferably, the chemotherapeutic agent is a nitrogen mustard, an epipodophyllotoxin, an antibiotic, an anti-oxidant, or a platinum coordination complex. A more preferred chemotherapeutic agent is bleomycin, doxorubicin, paclitaxel, etoposide, 4-OH cyclophosphamide, cisplatinum, or mitomycin-C. A presently preferred chemotherapeutic agent is doxorubicin, bleomycin, taxol, or mitomycin-C.

The mechanism of action of cyclo[n]pyrroles as a chemosensitizer remains to be established definitively. While not wanting to be bound by theory, it is thought that cyclo[n]pyrroles may inhibit repair of cellular damage caused by the chemotherapeutic agent, cyclo[n]pyrroles may compromise the cell's energy stores, or may increase free radical life span.

The use of cyclo[n]pyrroles as a chemosensitizer has an important advantage due to localization of cyclo[n]pyrroles due to their tunable hydrophilicity or hydrophobicity. It may thus be possible to administer less chemotherapeutic agent in the presence of cyclo[n]pyrroles to obtain a desired effect. As a result of being exposed to less chemotherapy, the patient may experience less general toxicity, while regions with a concentration of chemotherapeutic agent experience enhanced cytotoxicity.

Cyclo[n]pyrroles may be administered before, at the same time, or after administration of the chemotherapeutic drug. The cyclo[n]pyrrole may be administered as a single dose, or it may be administered as two or more doses separated by an interval of time. The cyclo[n]pyrrole may be administered from about one minute to about 12 hr following administration of the chemotherapeutic drug, preferably from about 5 min to about 5 hr, more preferably about 4 to 5 hr. The dosing protocol may be repeated, from one to three times, for example. Administration may be intra-arterial injection, intravenous, intraperitoneal, parenteral, intramuscular, subcutaneous, oral, topical, or via a device such as a stent, for example, with parenteral and intra-arterial administration being preferred, and intra-arterial being more preferred.

Administering a cyclo[n]pyrrole and a chemotherapeutic drug to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of cyclo[n]pyrrole and chemotherapeutic drug will be within 6–12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

In one aspect of the invention, a patient having cardiovascular disease is administered a dose of cyclo[n]pyrrole at intervals with each dose of the chemotherapeutic agent. A further step of performing angioplasty on the subject, or placing a stent into the subject is a further aspect of the present invention. The stent may be impregnated with the cyclo[n]pyrrole and the chemotherapeutic agent in yet another embodiment of the invention.

Radiation Sensitization. The red-shifted absorption spectrum of cyclo[n]pyrroles means that the gap between the highest occupied and lowest unoccupied molecular orbitals is relatively small in cyclo[n]pyrroles and that cyclo[n]pyrroles are easier to reduce than macrocycles not having such a red-shifted spectrum, such as porphyrins. Further, the choice of the number of pyrroles in the cyclo[n]pyrrole or changing the peripheral substituents is expected to be a way of modulating the redox potential of the macrocycle. Due to the variety of oxidation states for cyclo[n]pyrroles and the low level of the lowest unoccupied molecular orbital or orbitals, they are expected to "soak up" electrons readily and prevent a reaction between electrons and hydroxyl radicals or other oxidized species that result from radiation. This property enhances the amount of radiation damage incurred at a radiation site since hydroxyl radicals are then free to cause damage. In the absence of a radiation sensitizer, hydroxyl radicals and hydrated electrons recombine and little radiation damage occurs. Furthermore, the trapping of electrons by a radiation sensitizer prevents hydrated electrons from interacting with the hydroxyl radical-induced damage site to repair the damage. Electron trapping by cyclo[n]pyrroles as the result of reduction from endogenous electron rich agents, such as NADPH, glutathione, and ascorbate, could allow for radiation sensitization via so-called redox cycling as taught in D. Magda, et al., *Int. J. Radiat. Biol. Oncol. Phys.* 2001, 51 1025–1036.

Use of a cyclo[n]pyrrole described herein as a radiation sensitizer is expected to allow reduced doses of radiation to be effective in treatment of an individual. Therefore, radiation side effects such as nausea and damage to normal cells may be lessened when treatment includes the use of cyclo [n]pyrroles. An enhancement of radiation damage is expected to be unaffected by the presence of oxygen, therefore, the potential exists to increase damage in both oxic and hypoxic areas.

A cyclo[n]pyrrole bearing water solubilizing substituents for use as a radiation sensitizer may be administered in a solution containing 2 mM optionally in 5% mannitol USP/water (sterile and non-pyrogenic solution). Dosages of 0.1 mg/kg up to as high as about 30 or 50 mg/kg are contemplated, optionally with pre-medication using anti-emetics. The cyclo[n]pyrrole is administered via intravenous injection over about a 5 to 10 minute period, followed by a waiting period of about 2 to 5 hours to facilitate intracellular uptake and clearance from the plasma and extracellular matrix prior to the administration of radiation.

When employing radiation therapy, a palliative course of 30 Gy in ten (10) fractions of radiation are administered over consecutive days excluding weekends and holidays. In the treatment of brain metastases, whole brain megavolt radiation therapy is delivered with $^{60}$Co teletherapy or a $\geq 4$ MV linear accelerator with isocenter distances of at least 80 cm, using isocentric techniques, opposed lateral fields and exclusion of the eyes. A minimum dose rate at the midplane in the brain on the central axis is about 0.5 Gy/minute.

Cyclo[n]pyrroles used as radiation sensitizers may be administered before, or at the same time as, or after administration of the ionizing radiation. The cyclo[n]pyrrole may be administered as a single dose, as an infusion, or it may be administered as two or more doses separated by an interval of time. Where the cyclo[n]pyrrole is administered as two or more doses, the time interval between the cyclo[n]pyrrole administrations may be from about one minute to a number of days, preferably from about 5 min to about 1 day, more preferably about 4 to 5 hr. The dosing protocol may be repeated, from one to ten or more times, for example. Dose levels for radiation sensitization may range from about 0.05 $\mu$mol/kg to about 20 $\mu$mol/kg administered in single or multiple doses (e.g. before each fraction of radiation). A lower dosage range is presently preferred for intra-arterial injection or for impregnated stents. In the case of cyclo[n] pyrroles incorporating or conjugated to a radioisotope, the additional administration of radiation as a co-therapeutic agent is optional.

Administration may be intra-arterial injection, intravenous, intraperitoneal, parenteral, intramuscular, subcutaneous, oral, topical, or via an impregnated or coated device such as a stent, for example, or an artery-inserted cylindrical polymer, with parenteral and intra-arterial administration being preferred, and intra-arterial being more preferred. In one aspect of the invention, a patient having restenosis or at risk for restenosis is administered a dose of cyclo[n]pyrrole at intervals with each dose of radiation.

Administering a cyclo[n]pyrrole to the subject may be prior to, concurrent with, or following vascular intervention, and the intervention is followed by radiation. The method may begin prior to, such as about 24–48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of cyclo[n]pyrrole and radiation will be within 1–24 hours of the vascular intervention, preferably within about 5–24 hours thereafter. Follow-up dosages may be made at weekly, biweekly, or monthly intervals. Design of particular protocols depends on the individual subject, the condition of the subject, the design of dosage levels, and the judgment of the attending practitioner.

For radiation sensitization methods of the present invention, the radiation is in the form of x-rays, internal or external gamma emitting radioisotopes, or ionizing particles such as α or β particles, for example.

EXAMPLE 8

Oxidative Coupling for Synthesis of Macrocycles

The present inventors envision that, starting from readily available dipyrromethanes (8a), it is possible to obtain macrocycles in a single step and in good yield, using a method identical or analogous to the one that was used for the formation of cyclo[n]pyrroles in Example 1. These macrocycles (shown below) were previously available from more tedious syntheses employing β-substituted bipyrrolic precursors. For example, a dipyrromethane derivative 8a may be coupled under said conditions to produce rosarin 8b where n is 1. Alternatively, larger macrocycles can be obtained where n is 2–10.

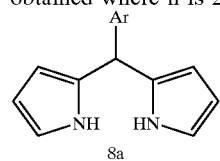
8a

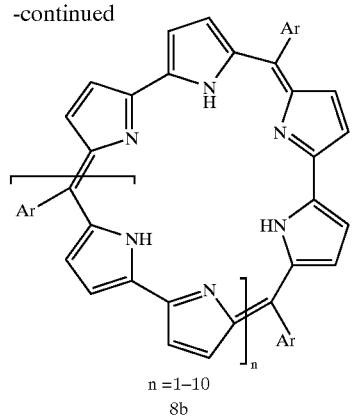
n =1–10
8b

In a further example, starting from readily available tripyrranes such as 8c, oxidative coupling identical or analogous to the one that was used for the formation of cyclo[n] pyrroles in Example 1 may generate rubyrin macrocycles 8d as outlined below.

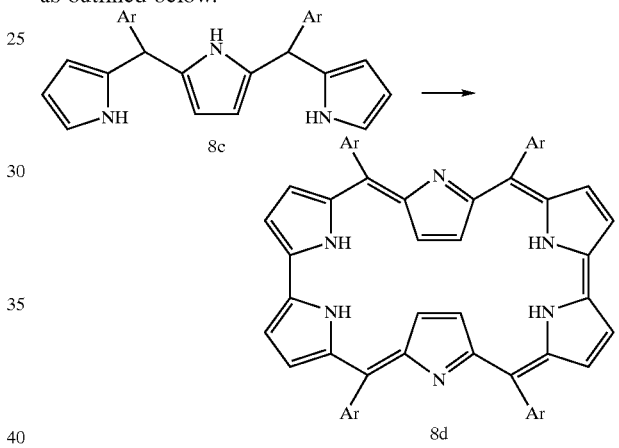
8c
8d

As outlined below, [32]octaphyrin(1.0.0.0.1.0.0.0) 8f as well as analogues bearing other pyrrolic substituents, may be synthesized by oxidative coupling of a bis-bipyrrole 8e employing Cr(VI) in trifluoroacetic acid. Use of the biphasic approach identical or analogous to the one that was used for the formation of cyclo[n]pyrroles in Example 1 would constitute a considerable improvement of the current approach.

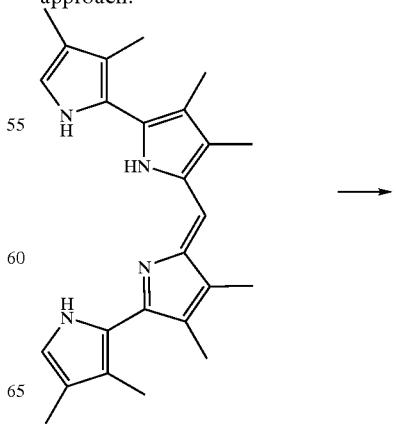

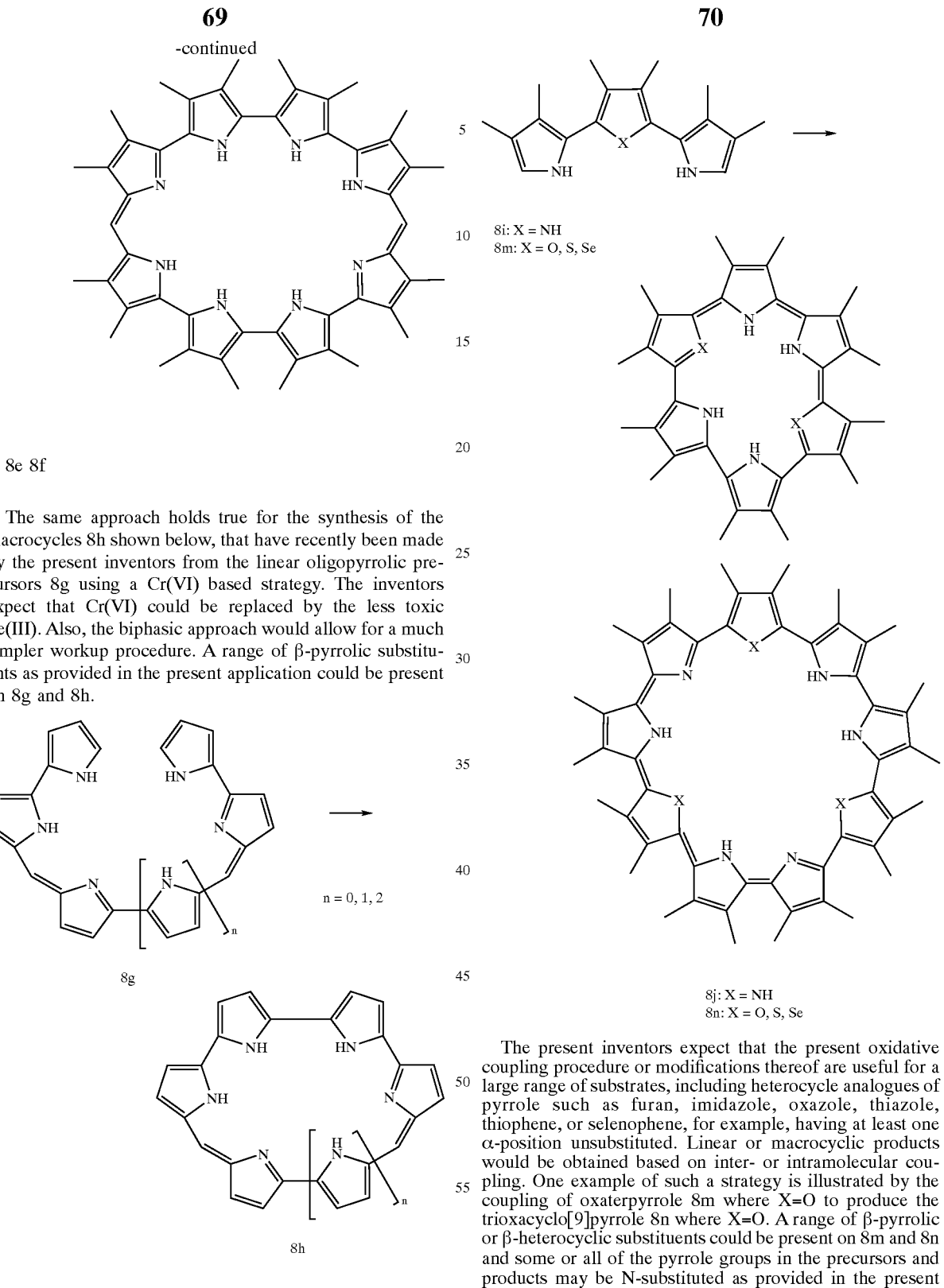

8i: X = NH
8m: X = O, S, Se 8e 8f

The same approach holds true for the synthesis of the macrocycles 8h shown below, that have recently been made by the present inventors from the linear oligopyrrolic precursors 8g using a Cr(VI) based strategy. The inventors expect that Cr(VI) could be replaced by the less toxic Fe(III). Also, the biphasic approach would allow for a much simpler workup procedure. A range of β-pyrrolic substituents as provided in the present application could be present on 8g and 8h.

n = 0, 1, 2

8g

8h

In another example, a cyclo[9]pyrrole such as 8j may be obtained by the oxidative coupling of terpyrrole 8i, employing conditions analogous or similar to those outlined supra. Again, a range of β-pyrrolic substituents as provided in the present application could be present on both the open chain precursors and the macrocyclic cyclo[8] pyrrolic products.

8j: X = NH
8n: X = O, S, Se

The present inventors expect that the present oxidative coupling procedure or modifications thereof are useful for a large range of substrates, including heterocycle analogues of pyrrole such as furan, imidazole, oxazole, thiazole, thiophene, or selenophene, for example, having at least one α-position unsubstituted. Linear or macrocyclic products would be obtained based on inter- or intramolecular coupling. One example of such a strategy is illustrated by the coupling of oxaterpyrrole 8m where X=O to produce the trioxacyclo[9]pyrrole 8n where X=O. A range of β-pyrrolic or β-heterocyclic substituents could be present on 8m and 8n and some or all of the pyrrole groups in the precursors and products may be N-substituted as provided in the present application.

In one embodiment of the invention, the present inventors expect that the heterocyclic analogues may be synthesized exclusively from heterocyclic precursors where the heterocyclic atom is other than nitrogen. Hence, heterocyclic[n] pyrrole macrocycles are provided by the present invention where the heteroatom is other than nitrogen. In a related embodiment, the heterocyclic precursors contain more than one heteroatom (defined as an atom other than carbon or hydrogen), one of which, two of which, or neither of which may be nitrogen. Preferably, these two heteroatoms will be arranged at the 1 and 3 positions of the heterocycle. Thus, cyclo[n]pyrrole analogues are provided by the present invention that contain heteroatoms at what are the beta positions of the cyclo[n]pyrroles taught in Example 1.

The present inventors envision that cyclo[n]pyrrole 8 1 may also be obtained from pyrrole 8k by using oxidative coupling approaches detailed in the present application in addition to those reaction parameters particular to pyrrole, such as solvent, concentration, reaction time, or pH, for example. The use of 3,4-difluoropyrrole or other pyrroles bearing electron withdrawing groups in the beta positions as starting materials is envisioned by the inventors as being particularly advantageous in this context since the stability of the starting material and products is expected to be enhanced. Cyclo[n]pyrroles synthesized in this way may be obtained in lower yields than for the optimized procedures detailed in Example 1, in part because a greater number of new bonds are being formed. However, the greater accessibility of pyrrolic, as opposed to bipyrrolic, precursors could render such an approach advantageous in certain situations. Beta-pyrrolic substitutents, $R^1$ and $R^2$, are as provided in the present application for numbered R substituents. In light of the present disclosure, one of skill in the art would recognize those that are electron withdrawing. Isomeric cyclo[n]pyrroles will be obtained in the event that $R^1 \neq R^2$.

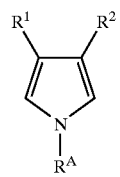

8k

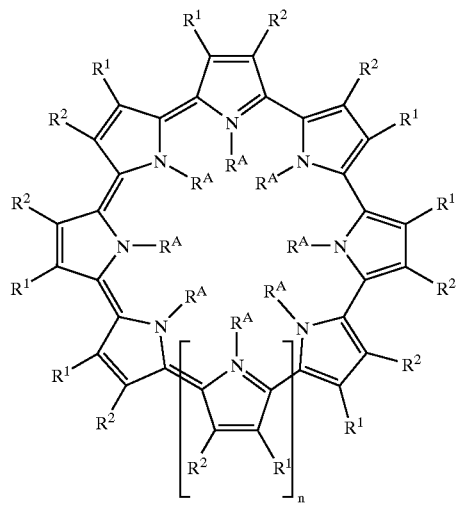

81

What is claimed is:

1. A composition comprising a cyclo[n]pyrrole having no meso carbon atoms where n is 6, 7, 8, 9, 10, 11, or 12.

2. A composition comprising a bridged cyclo[n]pyrrole having no meso carbon atoms where n is 6, 8, 10, or 12.

3. A compound comprising a cyclo[n]pyrrole macrocycle having structure I:

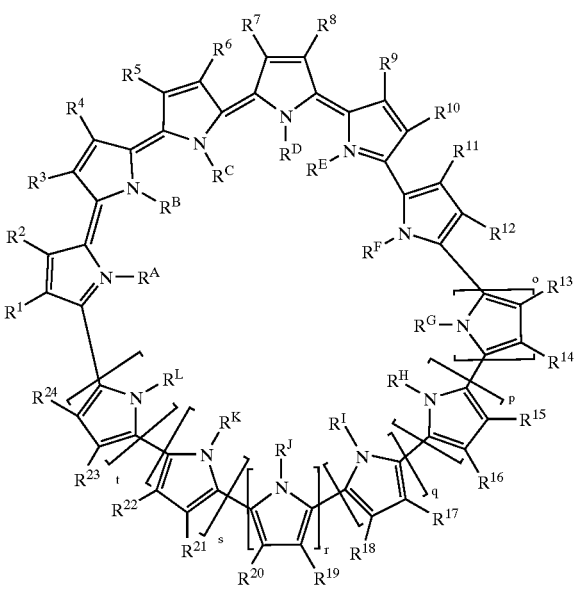

wherein n is 6, 7, 8, 9, 10, 11, or 12; and
when n is 6; o=p=q=r=s=t=0, numbered R substituents are independently as listed in paragraph i) below, $R^A$–$R^F$ are independently substituents as listed in paragraph ii) below;
when n is 7; o=1, p=q=r=s=t=0, numbered R substituents are independently as listed in paragraph i) below, $R^A$–$R^G$ are independently substituents as listed in paragraph ii) below;
when n is 8; o=p=1, q=r=s=t=0, numbered R substituents are independently as listed in paragraph i) below, $R^A$–$R^H$ are independently substituents as listed in paragraph ii) below;
when n is 9; o=p=q=1, r=s=t=0, numbered R substituents are independently as listed in paragraph i) below, $R^A$–$R^I$ are independently substituents as listed in paragraph ii) below;
when n is 10; o=p=q=r=1, s=t=0, numbered R substituents are independently as listed in paragraph i) below, $R^A$–$R^J$ are independently substituents as listed in paragraph ii) below;
when n is 11; o=p=q=r=s=1, t=0, numbered R substituents are independently as listed in paragraph i) below, $R^A$–$R^K$ are independently substituents as listed in paragraph ii) below;
when n is 12; o=p=q=r=s=t=1, numbered R substituents are independently as listed in paragraph i) below, $R^A$–$R^L$ are independently substituents as listed in paragraph ii) below;

i) hydrogen, alkyl, alkenyl, alkynyl, aryl, alkylaryl, formyl, acyl, hydroxyalkyl, hydroxyalkoxy, hydroxyalkenyl, hydroxyalkynyl, saccharide, carboxy, carboxyalkyl, carboxyamide, carboxyamidealkyl, alkyl sulfoxide, alkyl sulfone, alkyl sulfide, tetrahydropyran, tetrahydrothiapyran, thioalkyl, haloalkyl, haloalkenyl, haloalkynyl, alkyl ester, a site-directing molecule, a catalytic group, a reporter group, a binding agent, or a couple that is coupled to a site-directing molecule, to a catalytic group, to a reporter group, or to a binding agent;

ii) a pair of electrons, hydrogen, alkyl, aminoalkyl, alkylsulfone, carboxy alkyl, carboxyamidealkyl, phospho alkyl, alkyl sulfoxide, alkyl sulfone, alkyl sulfide, haloalkyl, aryl, N-oxide, dialkylamino, carbamate, or arylsulfonyl;

or
  at least two substituents are coupled to form a linked structure, and when coupled to form a linked structure, nonlinked substituents are as defined herein in paragraph i) or ii).

4. A compound comprising a bridged cyclo[n]pyrrole macrocycle having structure II:

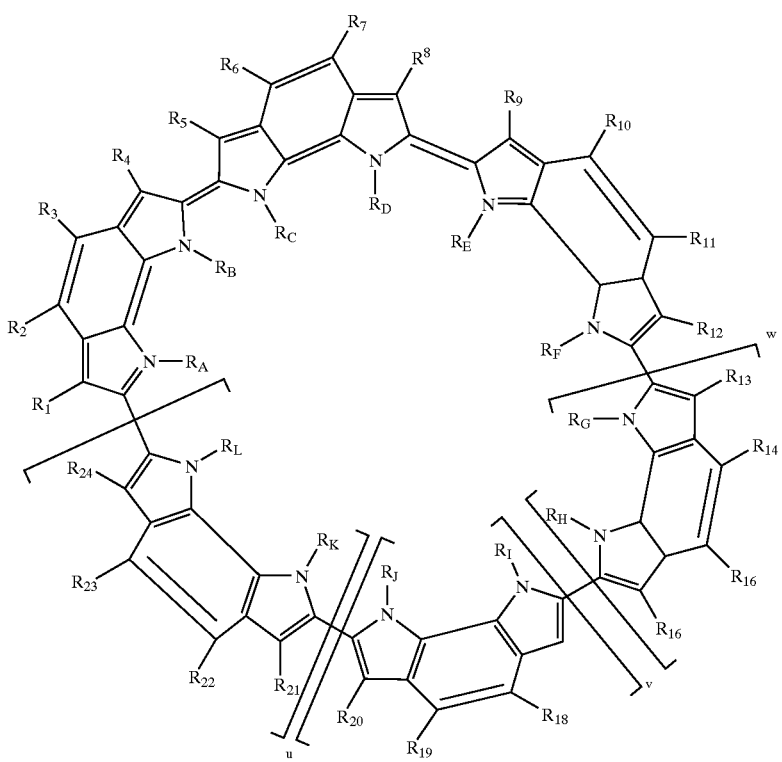

II wherein n is 6, 8, 10, or 12; and
  when n is 6; w=v=u=0, numbered R substituents are independently as listed in paragraph i) below, $R_A$–$R_F$ are independently substituents as listed in paragraph ii) below
  when n is 8; w=1, v=u=0, numbered R substituents are independently as listed in paragraph i) below, $R_A$–$R_H$ are independently substituents as listed in paragraph ii) below;
  when n is 10; w=v=1, u=0, numbered R substituents are independently as listed in paragraph i) below, $R_A$–$R_J$ are independently substituents as listed in paragraph ii) below;
  when n is 12; w=v=u=1, numbered R substituents are independently as listed in paragraph i) below, $R_A$–$R_L$ are independently substituents as listed in paragraph ii) below;
  i) hydrogen, alkyl, alkenyl, alkynyl, aryl, alkylaryl, formyl, acyl, hydroxyalkyl, hydroxyalkoxy, hydroxyalkenyl, hydroxyalkynyl, saccharide, carboxy, carboxyalkyl, carboxyamide, carboxyamidealkyl, alkyl sulfoxide, alkyl sulfone, alkyl sulfide, tetrahydropyran, tetrahydrothiapyran, thioalkyl, haloalkyl, haloalkenyl, haloalkynyl, alkyl ester, a site-directing molecule, a catalytic group, a reporter group, a binding agent, or a couple that is coupled to a site-directing molecule, to a catalytic group, to a reporter group, or to a binding agent;
  ii) a pair of electrons, hydrogen, alkyl, aminoalkyl, alkylsulfone, carboxy alkyl, carboxyamidealkyl, phospho alkyl, alkyl sulfoxide, alkyl sulfone, alkyl sulfide, haloalkyl, aryl, N-oxide, dialkylamino, carbamate, or arylsulfonyl;
  or
    at least two substituents are coupled to form a linked structure, and when coupled to form a linked structure, nonlinked substituents are as defined herein in paragraph i) or ii).

5. A coordination complex comprising a cyclo[n]pyrrole of claim 1 coordinated with a metal cation.

6. A noncovalently-bonded complex comprising a cyclo[n]pyrrole of claim 1 and an ion or a neutral molecule.

7. A nonlinear optical material comprising a cyclo[n]pyrrole of claim 1.

8. An optical storage medium comprising a cyclo[n]pyrrole of claim 1.

9. A laser hardening dye comprising a cyclo[n]pyrrole of claim 1.

10. An infrared filter comprising a cyclo[n]pyrrole of claim 1.

* * * * *